United States Patent
Selsted et al.

(10) Patent No.: US 6,514,727 B1
(45) Date of Patent: Feb. 4, 2003

(54) ANTIMICROBIAL THETA DEFENSINS AND METHODS OF USING SAME

(75) Inventors: Michael E. Selsted, Irvine, CA (US); Yi-Quan Tang, Irvine, CA (US); Jun Yuan, Dove Canyon, CA (US); Andre J. Ouellette, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/967,808

(22) Filed: Sep. 26, 2001

Related U.S. Application Data

(63) Continuation of application No. 09/309,487, filed on May 10, 1999, now Pat. No. 6,335,318.

(51) Int. Cl.$^7$ .................. C12N 15/09; C12N 15/00; C12N 5/00; C07H 21/02; C07H 21/04
(52) U.S. Cl. .................. 435/69.3; 435/320.1; 435/325; 536/23.1; 536/23.7
(58) Field of Search .................. 435/69.3, 320.1, 435/325; 536/23.1, 23.7

(56) References Cited

U.S. PATENT DOCUMENTS

| | | |
|---|---|---|
| 4,543,252 A | 9/1985 | Lehrer et al. |
| 4,659,692 A | 4/1987 | Lehrer et al. |
| 4,705,777 A | 11/1987 | Lehrer et al. |
| 5,242,902 A | 9/1993 | Murphy et al. |
| 5,324,716 A | 6/1994 | Selsted et al. |
| 5,422,424 A | 6/1995 | Selsted et al. |
| 5,459,235 A | 10/1995 | Selsted et al. |
| 5,547,939 A | 8/1996 | Selsted |
| 5,731,149 A | 3/1998 | Selsted et al. |
| 5,804,558 A | 9/1998 | Lehrer et al. |
| 5,821,224 A | 10/1998 | Selsted et al. |
| 5,840,498 A | 11/1998 | Selsted et al. |
| 5,844,072 A | 12/1998 | Selsted et al. |

FOREIGN PATENT DOCUMENTS

| | | |
|---|---|---|
| WO | WO 96/16075 | 5/1996 |
| WO | WO 97/08199 | 3/1997 |
| WO | WO 99/11663 | 3/1999 |
| WO | WO 99/13080 | 3/1999 |

OTHER PUBLICATIONS

Ahmad et al., "Liposomal entrapment of the neutrophil–derived peptide indolicidin endows it with in vivo antifungal activity," *Biochem. Biophys. Acta.*, 1237:109–114 (1995).

Bals et al., "Mouse β–Defensin 1 Is A Salt–Sensitive Antimicrobial Peptide Present in Epithelia of the Lung and Urogenital Tract," *Infect. Immun.*, 66:1225–1232 (1998).

Blond et al., "The cyclic structure of microcin J25, a 21–residue peptide antibiotic form *Escherichia coli*," *Eur. J. Biochem.*, 259:747–755 (1999).

Derua et al., "Analysis of the Disulfide Linkage Pattern in Circulin A and B, HIV–Inhibitory Macrocyclic Peptides," *Biochem. Biophys. Res. Commun.*, 228:632–638 (1996).

Galvez et al., "Purification and Amino Acid Composition of Peptide Antibiotic AS–48 Produced by *Streptococcus (Enterococcus) faecalis* subsp. *liquefaciens* S–48," *Antimicrob. Agents Chemother.*, 33:437–441 (1989).

Goldman et al., "Human β–Defensin–1 Is a Salt–Sensitive Antibiotic in Lung That Is Inactivated in Cyctic Fibrosis," *Cell*, 88:553–560 (1997).

Gustafson et al., "Circulins A and B: Novel HIV–Inhibitory Macrocyclic Peptides from the Tropical Tree *Chassalia parvifolia*," *J. Amer. Chem. Soc.*, 116:9337–9338 (1994).

Lehrer and Ganz, "Antimicrobial peptides in mammalian and insect host defence," *Current Opinion Immunol.* 11:23–27 (1999).

Lehrer et al., "Defensins: Endogenous Antibiotic Peptides of Animal Cells," *Cell*, 64:229–230 (1991).

Smith et al., "Cystic Fibrosis Airway Epithelia Fail to Kill Bacteria Because of Abnormal Airway Surface Fluid," *Cell*, 85:229–236 (1996).

Tang and Selsted, "Characterization of the Disulfide Motif in BNBD–12, and Antimicrobial β–Defensin Peptide from Bovine Neutrophils," *J. Biol. Chem.*, 268:6649–6653 (1993).

Valore et al., "Human β–Defensin–1: An Antimicrobial Peptide of Urogenital Tissues," *J Clin. Invest.*, 101:1633–1642 (1998).

Wade et al., "All–D amino acid–containing channel–forming antibiotic peptides," *Proc. Natl. Acad. Sci. USA*, 87:4761–4765 (1990).

Wu et al., "Protein trans–splicing by a split intein encoded in a split DnaE gene of Synechocystis sp. PCC6803," *Proc. Natl. Acad. Sci. USA*, 95:9226–9231 (1998).

Zanetti et al., "Cathelicidins: a novel protein family with a common proregion and a variable C–terminal antimicrobial domain," *FEBS Lett.*, 347:1–5 (1995).

*Primary Examiner*—Mark Navarro
(74) *Attorney, Agent, or Firm*—Campbell & Flores LLP

(57) ABSTRACT

The present invention relates to an isolated cyclic peptide, theta defensin, having antimicrobial activity, and to theta defensin analogs. A theta defensin can have the amino acid sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa5, wherein Xaa1 to Xaa8 are defined; wherein Xaa1 can be linked through a peptide bond to Xaa8; and wherein crosslinks can be formed between Xaa3 and Xaa3, between Xaa5 and Xaa5, and between Xaa7 and Xaa7. For example, the invention provides a theta defensin having the amino acid sequence Gly-Phe-Cys-Arg-Cys-Leu-Cys-Arg-Arg-Gly-Val-Cys-Arg-Cys-Ile-Cys-Thr-Arg (SEQ ID NO:1), wherein the Gly at position 1 (Gly-1) is linked through a peptide bond to Arg-18, and wherein disulfide bonds are present between Cys-3 and Cys-16, between Cys-5 and Cys-14, and between Cys-7 and Cys-12. The invention also relates to antibodies that specifically bind a theta defensin and to isolated nucleic acid molecules encoding a theta defensin. In addition, the invention relates to methods of using theta defensin or a theta defensin analog to reduce or inhibit microbial growth or survival in an environment capable of sustaining microbial growth or survival by contacting the environment with the theta defensin.

20 Claims, 25 Drawing Sheets

| PEPTIDE | SEQUENCE | MASS (m/z) |
|---|---|---|
| T-2 | $G^1$-F-C(R) | 586.6 (586.7) |
| CT-1 | C-R-C-L | 704.5 (703.9) |
| T-3 | C-L-C-R | 704.6 (703.8) |
| CT-2 | C-R-R-G-V-C | 903.0 (903.1) |
| T-4 | R-G-V-C-R | 694.3 (694.8) |
| CT-3 | R-C-I-C-T-$R^{18}$-$G^1$(F) | 1164.5 (1165.7) |
| T-1 | C-I-C-T-R | 805.4 (805.0) |
| MeOH/HCl | T-$R^{18}$-$G^1$-F-C-R-C-L-C-R-R-G-V-C-R-C-I-C | not analyzed |

$G^1$-F-C-R-C-L-C-R-R-G-V-C-R-C-I-C-T-$R^{18}$

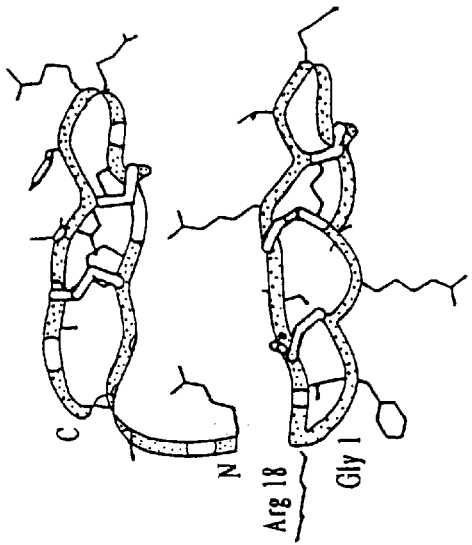
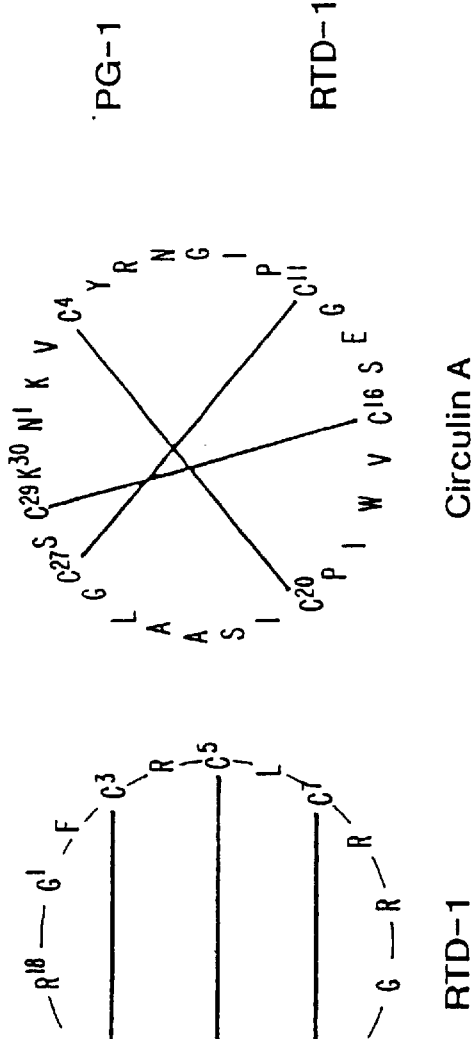
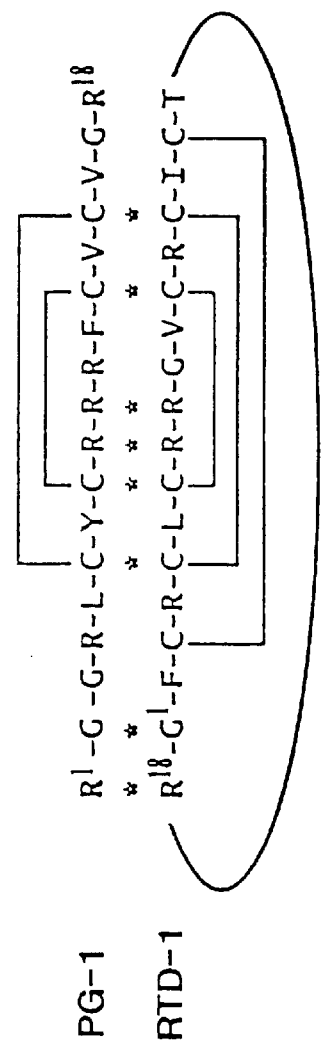
FIG. 4A
FIG. 4B
FIG. 4C

|  |  | Atom Name | Residue Name | Residue Sequence Number | X | Y | Z |  |  |  |
|---|---|---|---|---|---|---|---|---|---|---|
| ATOM | 1 | N | ARG | 1 | 4.445 | 1.973 | 1.040 | 0.00 | 0.00 | N |
| ATOM | 2 | CA | ARG | 1 | 5.522 | 1.436 | 0.144 | 0.00 | 0.00 | C |
| ATOM | 3 | C | ARG | 1 | 4.975 | 0.520 | -1.001 | 0.00 | 0.00 | C |
| ATOM | 4 | C | ARG | 1 | 5.013 | 0.909 | -2.171 | 0.00 | 0.00 | O |
| ATOM | 5 | CB | ARG | 1 | 6.757 | 0.901 | 0.940 | 0.00 | 0.00 | C |
| ATOM | 6 | CG | ARG | 1 | 8.115 | 0.817 | 0.196 | 0.00 | 0.00 | C |
| ATOM | 7 | CD | ARG | 1 | 8.247 | -0.348 | -0.805 | 0.00 | 0.00 | C |
| ATOM | 8 | NE | ARG | 1 | 9.635 | -0.394 | -1.339 | 0.00 | 0.00 | N1+ |
| ATOM | 9 | CZ | ARG | 1 | 10.094 | -1.285 | -2.220 | 0.00 | 0.00 | C |
| ATOM | 10 | NH1 | ARG | 1 | 9.363 | -2.248 | -2.726 | 0.00 | 0.00 | N |
| ATOM | 11 | NH2 | ARG | 1 | 11.336 | -1.194 | -2.598 | 1.00 | 0.00 | N |
| ATOM | 12 | H | ARG | 1 | 4.004 | 2.884 | 0.861 | 0.00 | 0.00 | H |
| ATOM | 13 | HA | ARG | 1 | 5.896 | 2.332 | -0.389 | 0.00 | 0.00 | H |
| ATOM | 14 | 1HB | ARG | 1 | 6.913 | 1.571 | 1.809 | 0.00 | 0.00 | H |
| ATOM | 15 | 2HB | ARG | 1 | 6.517 | -0.076 | 1.403 | 0.00 | 0.00 | H |
| ATOM | 16 | 1HG | ARG | 1 | 8.325 | 1.782 | -0.307 | 0.00 | 0.00 | H |
| ATOM | 17 | 2HG | ARG | 1 | 8.908 | 0.718 | 0.964 | 0.00 | 0.00 | H |
| ATOM | 18 | 1HD | ARG | 1 | 7.985 | -1.303 | -0.303 | 0.00 | 0.00 | H |
| ATOM | 19 | 2HD | ARG | 1 | 7.523 | -0.218 | -1.635 | 0.00 | 0.00 | H |
| ATOM | 20 | HE | ARG | 1 | 10.329 | 0.298 | -1.044 | 1.00 | 0.00 | H |
| ATOM | 21 | 1HH1 | ARG | 1 | 8.398 | -2.263 | -2.391 | 0.00 | 0.00 | H |
| ATOM | 22 | 2HH1 | ARG | 1 | 9.794 | -2.889 | -3.396 | 0.00 | 0.00 | H |
| ATOM | 23 | 1HH2 | ARG | 1 | 11.891 | -0.439 | -2.191 | 0.00 | 0.00 | H |
| ATOM | 24 | 2HH2 | ARG | 1 | 11.669 | -1.886 | -3.272 | 0.00 | 0.00 | H |
| ATOM | 25 | N | GLY | 2 | 4.471 | -0.678 | -0.668 | 0.00 | 0.00 | C |
| ATOM | 26 | CA | GLY | 2 | 3.645 | -1.487 | -1.607 | 0.00 | 0.00 | C |
| ATOM | 27 | C | GLY | 2 | 2.571 | -2.369 | -0.935 | 0.00 | 0.00 | O |
| ATOM | 28 | O | GLY | 2 | 2.483 | -3.558 | -1.244 | 0.00 | 0.00 | H |
| ATOM | 29 | H | GLY | 2 | 4.420 | -0.799 | 0.356 | 0.00 | 0.00 | H |
| ATOM | 30 | 1HA | GLY | 2 | 3.133 | -0.847 | -2.352 | 0.00 | 0.00 | H |
| ATOM | 31 | 2HA | GLY | 2 | 4.311 | -2.140 | -2.202 | 0.00 | 0.00 | N |
| ATOM | 32 | N | PHE | 3 | 1.744 | -1.787 | -0.048 | 1.00 | 0.00 | C |
| ATOM | 33 | CA | PHE | 3 | 0.707 | -2.540 | 0.716 | 1.00 | 0.00 | C |
| ATOM | 34 | C | PHE | 3 | -0.574 | -1.652 | 0.805 | 1.00 | 0.00 | O |
| ATOM | 35 | O | PHE | 3 | -0.719 | -0.840 | 1.725 | 1.00 | 0.00 | C |
| ATOM | 36 | CB | PHE | 3 | 1.236 | -2.949 | 2.125 | 1.00 | 0.00 | C |
| ATOM | 37 | CG | PHE | 3 | 2.397 | -3.960 | 2.159 | 1.00 | 0.00 | C |
| ATOM | 38 | CD1 | PHE | 3 | 3.705 | -3.524 | 2.398 | 1.00 | 0.00 | C |
| ATOM | 39 | CD2 | PHE | 3 | 2.159 | -5.321 | 1.934 | 1.00 | 0.00 | C |
| ATOM | 40 | CE1 | PHE | 3 | 4.760 | -4.433 | 2.407 | 1.00 | 0.00 | C |
| ATOM | 41 | CE2 | PHE | 3 | 3.215 | -6.230 | 1.945 | 1.00 | 0.00 | C |
| ATOM | 42 | CZ | PHE | 3 | 4.514 | -5.786 | 2.179 | 1.00 | 0.00 | C |
| ATOM | 43 | H | PHE | 3 | 1.994 | -0.817 | 0.174 | 1.00 | 0.00 | H |
| ATOM | 44 | HA | PHE | 3 | 0.434 | -3.475 | 0.183 | 1.00 | 0.00 | H |
| ATOM | 45 | 1HB | PHE | 3 | 1.516 | -2.038 | 2.686 | 1.00 | 0.00 | H |
| ATOM | 46 | 2HB | PHE | 3 | 0.399 | -3.371 | 2.714 | 1.00 | 0.00 | H |
| ATOM | 47 | HD1 | PHE | 3 | 3.909 | -2.478 | 2.569 | 1.00 | 0.00 | H |
| ATOM | 48 | HD2 | PHE | 3 | 1.157 | -5.676 | 1.741 | 1.00 | 0.00 | H |
| ATOM | 49 | HE1 | PHE | 3 | 5.768 | -4.090 | 2.587 | 1.00 | 0.00 | H |
| ATOM | 50 | HE2 | PHE | 3 | 3.027 | -7.279 | 1.768 | 1.00 | 0.00 | H |

FIG. 5A

| | | Atom Name | Resi-due Name | Residue Sequence Number | X | Y | Z | | | |
|---|---|---|---|---|---|---|---|---|---|---|
| ATOM | 51 | HZ | PHE | 3 | 5.333 | -6.491 | 2.183 | 1.00 | 0.00 | H |
| ATOM | 52 | N | CYS | 4 | -1.485 | -1.783 | -0.178 | 1.00 | 0.00 | N |
| ATOM | 53 | CA | CYS | 4 | -2.676 | -0.902 | -0.303 | 1.00 | 0.00 | C |
| ATOM | 54 | C | CYS | 4 | -3.883 | -1.384 | 0.565 | 1.00 | 0.00 | C |
| ATOM | 55 | O | CYS | 4 | -4.495 | -2.417 | 0.278 | 1.00 | 0.00 | O |
| ATOM | 56 | CB | CYS | 4 | -3.015 | -0.813 | -1.807 | 1.00 | 0.00 | V |
| ATOM | 57 | SG | CYS | 4 | -1.735 | 0.014 | -2.797 | 1.00 | 0.00 | D |
| ATOM | 58 | H | CYS | 4 | -1.244 | -2.461 | -0.908 | 1.00 | 0.00 | H |
| ATOM | 59 | HA | CYS | 4 | -2.421 | 0.128 | 0.002 | 1.00 | 0.00 | H |
| ATOM | 60 | HB | CYS | 4 | -3.217 | -1.814 | -2.236 | 1.00 | 0.00 | H |
| ATOM | 61 | 2HB | CYS | 4 | -3.953 | -0.243 | -1.946 | 1.00 | 0.00 | H |
| ATOM | 62 | N | ARG | 5 | -4.225 | -0.622 | 1.622 | 1.00 | 0.00 | N |
| ATOM | 63 | CA | ARG | 5 | -5.375 | -0.934 | 2.515 | 1.00 | 0.00 | C |
| ATOM | 64 | C | ARG | 5 | -6.403 | 0.241 | 2.508 | 1.00 | 0.00 | C |
| ATOM | 65 | O | ARG | 5 | -6.065 | 1.381 | 2.846 | 1.00 | 0.00 | O |
| ATOM | 66 | CB | ARG | 5 | -4.827 | -1.238 | 3.937 | 1.00 | 0.00 | C |
| ATOM | 67 | CG | ARG | 5 | -5.877 | -1.865 | 4.888 | 1.00 | 0.00 | C |
| ATOM | 68 | CD | ARG | 5 | -5.313 | -2.174 | 6.285 | 1.00 | 0.00 | C |
| ATOM | 69 | NE | ARG | 5 | -6.356 | -2.883 | 7.076 | 1.00 | 0.00 | N1+ |
| ATOM | 70 | CZ | ARG | 5 | -6.158 | -3.497 | 8.243 | 1.00 | 0.00 | C |
| ATOM | 71 | NH1 | ARG | 5 | -5.016 | -3.482 | 8.886 | 1.00 | 0.00 | N |
| ATOM | 72 | NH2 | ARG | 5 | -7.153 | -4.148 | 8.774 | 1.00 | 0.00 | N |
| ATOM | 73 | H | ARG | 5 | -3.631 | 0.210 | 1.776 | 1.00 | 0.00 | H |
| ATOM | 74 | HA | ARG | 5 | -5.883 | -1.856 | 2.164 | 1.00 | 0.00 | H |
| ATOM | 75 | 1HB | ARG | 5 | -3.968 | -1.934 | 3.853 | 1.00 | 0.00 | H |
| ATOM | 76 | 2HB | ARG | 5 | -4.404 | -0.313 | 4.380 | 1.00 | 0.00 | H |
| ATOM | 77 | 1HG | ARG | 5 | -6.752 | -1.190 | 4.979 | 1.00 | 0.00 | H |
| ATOM | 78 | 2HG | ARG | 5 | -6.263 | -2.796 | 4.425 | 1.00 | 0.00 | H |
| ATOM | 79 | 1HD | ARG | 5 | -4.398 | -2.793 | 6.184 | 1.00 | 0.00 | H |
| ATOM | 80 | 2HD | ARG | 5 | -5.007 | -1.233 | 6.787 | 1.00 | 0.00 | H |
| ATOM | 81 | HE | ARG | 5 | -7.304 | -2.991 | 6.704 | 1.00 | 0.00 | H |
| ATOM | 82 | 1HH1 | ARG | 5 | -4.945 | -3.988 | 9.771 | 1.00 | 0.00 | H |
| ATOM | 83 | 2HH1 | ARG | 5 | -4.279 | -2.952 | 8.417 | 1.00 | 0.00 | H |
| ATOM | 84 | 1HH2 | ARG | 5 | -8.031 | -4.162 | 8.252 | 1.00 | 0.00 | H |
| ATOM | 85 | 2HH2 | ARG | 5 | -6.978 | -4.625 | 9.661 | 1.00 | 0.00 | H |
| ATOM | 86 | N | CYS | 6 | -7.669 | -0.051 | 2.153 | 0.00 | 0.00 | H |
| ATOM | 87 | CA | CYS | 6 | -8.750 | 0.970 | 2.109 | 0.00 | 0.00 | C |
| ATOM | 88 | C | CYS | 6 | -9.798 | 0.729 | 3.238 | 0.00 | 0.00 | C |
| ATOM | 89 | O | CYS | 6 | -10.685 | -0.120 | 3.112 | 0.00 | 0.00 | O |
| ATOM | 90 | CB | CYS | 6 | -9.307 | 1.004 | 0.667 | 0.00 | 0.00 | C |
| ATOM | 91 | SG | CYS | 6 | -9.911 | 2.662 | 0.297 | 0.00 | 0.00 | S |
| ATOM | 92 | H | CYS | 6 | -7.825 | -1.007 | 1.819 | 0.00 | 0.00 | H |
| ATOM | 93 | HA | CYS | 6 | -8.329 | 1.972 | 2.283 | 0.00 | 0.00 | H |
| ATOM | 94 | 1HB | CYS | 6 | -8.529 | 0.778 | -0.088 | 0.00 | 0.00 | H |
| ATOM | 95 | 2HB | CYS | 6 | -10.109 | 0.258 | 0.513 | 0.00 | 0.00 | H |
| ATOM | 96 | N | LEU | 7 | -9.654 | 1.449 | 4.368 | 1.00 | 0.00 | N |
| ATOM | 97 | CA | LEU | 7 | -10.388 | 1.150 | 5.633 | 1.00 | 0.00 | C |
| ATOM | 98 | C | LEU | 7 | -11.434 | 2.249 | 6.009 | 1.00 | 0.00 | C |
| ATOM | 99 | O | LEU | 7 | -11.151 | 3.452 | 5.967 | 1.00 | 0.00 | O |
| ATOM | 100 | CB | LEU | 7 | -9.374 | 0.760 | 6.757 | 1.00 | 0.00 | C |

FIG. 5B

|  | | Atom Name | Residue Name | Residue Sequence Number | X | Y | Z | | | |
|---|---|---|---|---|---|---|---|---|---|---|
| ATOM | 101 | CG | LEU | 7 | -8.386 | 1.757 | 7.435 | 1.00 | 0.00 | C |
| ATOM | 102 | CD1 | LEU | 7 | -7.508 | 2.568 | 6.467 | 1.00 | 0.00 | C |
| ATOM | 103 | CD2 | LEU | 7 | -9.054 | 2.697 | 8.452 | 1.00 | 0.00 | C |
| ATOM | 104 | H | LEU | 7 | -8.903 | 2.151 | 4.337 | 1.00 | 0.00 | H |
| ATOM | 105 | HA | LEU | 7 | -10.966 | 0.215 | 5.476 | 1.00 | 0.00 | H |
| ATOM | 106 | 1HB | LEU | 7 | -9.954 | 0.273 | 7.565 | 1.00 | 0.00 | H |
| ATOM | 107 | 2HB | LEU | 7 | -8.762 | -0.073 | 6.359 | 1.00 | 0.00 | H |
| ATOM | 108 | HG | LEU | 7 | -7.689 | 1.128 | 8.025 | 1.00 | 0.00 | H |
| ATOM | 109 | 1HD1 | LEU | 7 | -6.711 | 3.120 | 6.998 | 1.00 | 0.00 | H |
| ATOM | 110 | 2HD1 | LEU | 7 | -7.007 | 1.923 | 5.722 | 1.00 | 0.00 | H |
| ATOM | 111 | 3HD1 | LEU | 7 | -8.097 | 3.320 | 5.909 | 1.00 | 0.00 | H |
| ATOM | 112 | 1HD2 | LEU | 7 | -8.302 | 3.262 | 9.032 | 1.00 | 0.00 | H |
| ATOM | 113 | 2HD2 | LEU | 7 | -9.705 | 3.447 | 7.967 | 1.00 | 0.00 | H |
| ATOM | 114 | 3HD2 | LEU | 7 | -9.676 | 2.141 | 9.177 | 1.00 | 0.00 | H |
| ATOM | 115 | N | CYS | 8 | -12.667 | 1.827 | 6.355 | 0.00 | 0.00 | N |
| ATOM | 116 | CA | CYS | 8 | -13.782 | 2.747 | 6.706 | 0.00 | 0.00 | C |
| ATOM | 117 | C | CYS | 8 | -13.756 | 3.194 | 8.202 | 0.00 | 0.00 | C |
| ATOM | 118 | O | CYS | 8 | -13.835 | 2.372 | 9.120 | 0.00 | 0.00 | O |
| ATOM | 119 | CB | CYS | 8 | -15.112 | 2.052 | 6.334 | 0.00 | 0.00 | C |
| ATOM | 120 | SG | CYS | 8 | -15.536 | 2.183 | 4.573 | 0.00 | 0.00 | S |
| ATOM | 121 | H | CYS | 8 | -12.799 | 0.811 | 6.359 | 0.00 | 0.00 | H |
| ATOM | 122 | HA | CYS | 8 | -13.732 | 3.653 | 6.080 | 0.00 | 0.00 | H |
| ATOM | 123 | 1HB | CYS | 8 | -15.135 | 0.991 | 6.649 | 0.00 | 0.00 | H |
| ATOM | 124 | 2HB | CYS | 8 | -15.953 | 2.528 | 6.873 | 0.00 | 0.00 | H |
| ATOM | 125 | N | ARG | 9 | -13.685 | 4.516 | 8.431 | 0.00 | 0.00 | N |
| ATOM | 126 | CA | ARG | 9 | -13.874 | 5.123 | 9.780 | 0.00 | 0.00 | C |
| ATOM | 127 | C | ARG | 9 | -15.143 | 6.030 | 9.740 | 0.00 | 0.00 | C |
| ATOM | 128 | O | ARG | 9 | -15.171 | 7.045 | 9.036 | 0.00 | 0.00 | O |
| ATOM | 129 | CB | ARG | 9 | -12.598 | 5.905 | 10.199 | 0.00 | 0.00 | C |
| ATOM | 130 | CG | ARG | 9 | -11.403 | 5.004 | 10.601 | 0.00 | 0.00 | C |
| ATOM | 131 | CD | ARG | 9 | -10.168 | 5.811 | 11.037 | 0.00 | 0.00 | C |
| ATOM | 132 | NE | ARG | 9 | -9.107 | 4.873 | 11.498 | 0.00 | 0.00 | N1+ |
| ATOM | 133 | CZ | ARG | 9 | -7.962 | 5.228 | 12.082 | 0.00 | 0.00 | C |
| ATOM | 134 | NH1 | ARG | 9 | -7.612 | 6.472 | 12.300 | 0.00 | 0.00 | N |
| ATOM | 135 | NH2 | ARG | 9 | -7.145 | 4.287 | 12.460 | 0.00 | 0.00 | N |
| ATOM | 136 | H | ARG | 9 | -13.622 | 5.093 | 7.583 | 0.00 | 0.00 | H |
| ATOM | 137 | HA | ARG | 9 | -14.035 | 4.337 | 10.547 | 0.00 | 0.00 | H |
| ATOM | 138 | 1HB | ARG | 9 | -12.303 | 6.603 | 9.389 | 0.00 | 0.00 | H |
| ATOM | 139 | 2HB | ARG | 9 | -12.846 | 6.559 | 11.059 | 0.00 | 0.00 | H |
| ATOM | 140 | 1HG | ARG | 9 | -11.723 | 4.325 | 11.418 | 0.00 | 0.00 | H |
| ATOM | 141 | 2HG | ARG | 9 | -11.146 | 4.340 | 9.752 | 0.00 | 0.00 | H |
| ATOM | 142 | 1HD | ARG | 9 | -9.805 | 6.431 | 10.192 | 0.00 | 0.00 | H |
| ATOM | 143 | 2HD | ARG | 9 | -10.454 | 6.513 | 11.848 | 0.00 | 0.00 | H |
| ATOM | 144 | HE | ARG | 9 | -9.235 | 3.861 | 11.406 | 0.00 | 0.00 | H |
| ATOM | 145 | 1HH1 | ARG | 9 | -8.298 | 7.161 | 11.984 | 0.00 | 0.00 | H |
| ATOM | 146 | 2HH1 | ARG | 9 | -6.722 | 6.657 | 12.767 | 0.00 | 0.00 | H |
| ATOM | 147 | 1HH2 | ARG | 9 | -7.438 | 3.323 | 12.293 | 0.00 | 0.00 | H |
| ATOM | 148 | 2HH2 | ARG | 9 | -6.278 | 4.578 | 12.915 | 0.00 | 0.00 | H |
| ATOM | 149 | N | ARG | 10 | -16.215 | 5.637 | 10.462 | 0.00 | 0.00 | N |
| ATOM | 150 | CA | ARG | 10 | -17.558 | 6.306 | 10.411 | 0.00 | 0.00 | C |

FIG. 5C

|      | Atom Name | Resi-due Name | Residue Sequence Number | X | Y | Z | | | |
|------|------|------|------|---------|--------|--------|------|------|-----|
| ATOM | 151 | C    | ARG | 10 -18.386 | 6.033 | 9.106 | 0.00 | 0.00 | C |
| ATOM | 152 | O    | ARG | 10 -19.548 | 5.622 | 9.208 | 0.00 | 0.00 | O |
| ATOM | 153 | CB   | ARG | 10 -17.530 | 7.803 | 10.875 | 0.00 | 0.00 | C |
| ATOM | 154 | CG   | ARG | 10 -18.722 | 8.328 | 11.730 | 0.00 | 0.00 | C |
| ATOM | 155 | CD   | ARG | 10 -19.968 | 8.899 | 11.012 | 0.00 | 0.00 | C |
| ATOM | 156 | NE   | ARG | 10 -20.779 | 7.815 | 10.397 | 0.00 | 0.00 | N1+ |
| ATOM | 157 | CZ   | ARG | 10 -22.072 | 7.865 | 10.088 | 0.00 | 0.00 | C |
| ATOM | 158 | NH1  | ARG | 10 -22.840 | 8.904 | 10.304 | 0.00 | 0.00 | N |
| ATOM | 159 | NH2  | ARG | 10 -22.596 | 6.811 | 9.533 | 0.00 | 0.00 | N |
| ATOM | 160 | H    | ARG | 10 -16.078 | 4.751 | 10.960 | 0.00 | 0.00 | H |
| ATOM | 161 | HA   | ARG | 10 -18.128 | 5.773 | 11.197 | 0.00 | 0.00 | H |
| ATOM | 162 | 1HB  | ARG | 10 -16.626 | 7.944 | 11.500 | 0.00 | 0.00 | H |
| ATOM | 163 | 2HB  | ARG | 10 -17.343 | 8.470 | 10.010 | 0.00 | 0.00 | H |
| ATOM | 164 | 1HG  | ARG | 10 -19.024 | 7.571 | 12.481 | 0.00 | 0.00 | H |
| ATOM | 165 | 2HG  | ARG | 10 -18.324 | 9.134 | 12.353 | 0.00 | 0.00 | H |
| ATOM | 166 | 1HD  | ARG | 10 -20.560 | 9.461 | 11.764 | 0.00 | 0.00 | H |
| ATOM | 167 | 2HD  | ARG | 10 -19.665 | 9.645 | 10.248 | 0.00 | 0.00 | H |
| ATOM | 168 | HE   | ARG | 10 -20.325 | 6.941 | 10.030 | 1.00 | 0.00 | H |
| ATOM | 169 | 1HH1 | ARG | 10 -22.362 | 9.705 | 10.720 | 0.00 | 0.00 | H |
| ATOM | 170 | 2HH1 | ARG | 10 -23.822 | 8.848 | 10.030 | 0.00 | 0.00 | H |
| ATOM | 171 | 1HH2 | ARG | 10 -21.958 | 6.023 | 9.378 | 0.00 | 0.00 | H |
| ATOM | 172 | 2HH2 | ARG | 10 -23.590 | 6.840 | 9.301 | 0.00 | 0.00 | H |
| ATOM | 173 | N    | GLY | 11 -17.826 | 6.288 | 7.910 | 1.00 | 0.00 | N |
| ATOM | 174 | CA   | GLY | 11 -18.511 | 6.016 | 6.617 | 1.00 | 0.00 | C |
| ATOM | 175 | C    | GLY | 11 -17.565 | 5.667 | 5.451 | 1.00 | 0.00 | C |
| ATOM | 176 | O    | GLY | 11 -17.541 | 4.520 | 5.003 | 1.00 | 0.00 | O |
| ATOM | 177 | H    | GLY | 11 -16.840 | 6.585 | 7.986 | 1.00 | 0.00 | H |
| ATOM | 178 | 1HA  | GLY | 11 -19.226 | 5.175 | 6.720 | 1.00 | 0.00 | H |
| ATOM | 179 | 2HA  | GLY | 11 -19.136 | 6.884 | 6.335 | 1.00 | 0.00 | H |
| ATOM | 180 | N    | VAL | 12 -16.817 | 6.655 | 4.932 | 1.00 | 0.00 | N |
| ATOM | 181 | CA   | VAL | 12 -15.952 | 6.477 | 3.722 | 1.00 | 0.00 | C |
| ATOM | 182 | C    | VAL | 12 -14.651 | 5.637 | 3.988 | 1.00 | 0.00 | C |
| ATOM | 183 | O    | VAL | 12 -13.950 | 5.844 | 4.985 | 1.00 | 0.00 | O |
| ATOM | 184 | CB   | VAL | 12 -15.688 | 7.880 | 3.064 | 1.00 | 0.00 | C |
| ATOM | 185 | CG1  | VAL | 12 -14.756 | 8.829 | 3.857 | 1.00 | 0.00 | C |
| ATOM | 186 | CG2  | VAL | 12 -15.155 | 7.773 | 1.617 | 1.00 | 0.00 | C |
| ATOM | 187 | H    | VAL | 12 -16.891 | 7.553 | 5.419 | 1.00 | 0.00 | H |
| ATOM | 188 | HA   | VAL | 12 -16.566 | 5.916 | 2.987 | 1.00 | 0.00 | H |
| ATOM | 189 | HB   | VAL | 12 -16.669 | 8.392 | 2.979 | 1.00 | 0.00 | H |
| ATOM | 190 | 1HG1 | VAL | 12 -13.729 | 8.426 | 3.491 | 1.00 | 0.00 | H |
| ATOM | 191 | 2HG1 | VAL | 12 -14.677 | 9.824 | 3.382 | 1.00 | 0.00 | H |
| ATOM | 192 | 3HG1 | VAL | 12 -15.118 | 8.997 | 4.887 | 1.00 | 0.00 | H |
| ATOM | 193 | 1HG2 | VAL | 12 -14.141 | 7.330 | 1.573 | 1.00 | 0.00 | H |
| ATOM | 194 | 2HG2 | VAL | 12 -15.809 | 7.151 | 0.978 | 1.00 | 0.00 | H |
| ATOM | 195 | 3HG3 | VAL | 12 -15.093 | 8.764 | 1.127 | 1.00 | 0.00 | N |
| ATOM | 196 | N    | CYS | 13 -14.317 | 4.713 | 3.063 | 0.00 | 0.00 | N |
| ATOM | 197 | CA   | CYS | 13 -13.052 | 3.937 | 3.118 | 0.00 | 0.00 | C |
| ATOM | 198 | C    | CYS | 13 -11.828 | 4.755 | 2.598 | 0.00 | 0.00 | C |
| ATOM | 199 | O    | CYS | 13 -11.730 | 5.076 | 1.409 | 0.00 | 0.00 | O |
| ATOM | 200 | CB   | CYS | 13 -13.246 | 2.600 | 2.374 | 0.00 | 0.00 | C |

FIG. 5D

| | Atom Name | Residue Name | Residue Sequence Number | X | Y | Z | | | |
|---|---|---|---|---|---|---|---|---|---|
| ATOM | 201 | SG | CYS | 13 | -14.168 | 1.373 | 3.345 | 0.00 | 0.00 | S |
| ATOM | 202 | H | CYS | 13 | -14.951 | 4.647 | 2.261 | 0.00 | 0.00 | H |
| ATOM | 203 | HA | CYS | 13 | -12.854 | 3.655 | 4.139 | 0.00 | 0.00 | H |
| ATOM | 204 | 1HB | CYS | 13 | -13.735 | 2.743 | 1.392 | 0.00 | 0.00 | H |
| ATOM | 205 | 2HB | CYS | 13 | -12.268 | 2.139 | 2.143 | 0.00 | 0.00 | H |
| ATOM | 206 | N | ARG | 14 | -10.889 | 5.085 | 3.504 | 1.00 | 0.00 | N |
| ATOM | 207 | CA | ARG | 14 | -9.666 | 5.853 | 3.152 | 1.00 | 0.00 | C |
| ATOM | 208 | C | ARG | 14 | -8.532 | 4.905 | 2.651 | 1.00 | 0.00 | C |
| ATOM | 209 | O | ARG | 14 | -7.977 | 4.113 | 3.420 | 1.00 | 0.00 | O |
| ATOM | 210 | CB | ARG | 14 | -9.264 | 6.723 | 4.379 | 1.00 | 0.00 | C |
| ATOM | 211 | CG | ARG | 14 | -7.945 | 7.536 | 4.266 | 1.00 | 0.00 | C |
| ATOM | 212 | CD | ARG | 14 | -7.860 | 8.519 | 3.077 | 1.00 | 0.00 | C |
| ATOM | 213 | NE | ARG | 14 | -6.479 | 9.065 | 2.938 | 1.00 | 0.00 | N1+ |
| ATOM | 214 | CZ | ARG | 14 | -6.046 | 10.234 | 3.413 | 1.00 | 0.00 | C |
| ATOM | 215 | NH1 | ARG | 14 | -6.786 | 11.050 | 4.122 | 1.00 | 0.00 | N |
| ATOM | 216 | NH2 | ARG | 14 | -4.818 | 10.584 | 3.160 | 1.00 | 0.00 | N |
| ATOM | 217 | H | ARG | 14 | -11.032 | 4.677 | 4.441 | 1.00 | 0.00 | H |
| ATOM | 218 | HA | ARG | 14 | -9.924 | 6.571 | 2.346 | 1.00 | 0.00 | H |
| ATOM | 219 | 1HB | ARG | 14 | -10.097 | 7.412 | 4.620 | 1.00 | 0.00 | H |
| ATOM | 220 | 2HB | ARG | 14 | -9.181 | 6.068 | 5.270 | 1.00 | 0.00 | H |
| ATOM | 221 | 1HG | ARG | 14 | -7.777 | 8.084 | 5.213 | 1.00 | 0.00 | H |
| ATOM | 222 | 2HG | ARG | 14 | -7.104 | 6.818 | 4.213 | 1.00 | 0.00 | H |
| ATOM | 223 | 1HD | ARG | 14 | -8.098 | 7.987 | 2.134 | 1.00 | 0.00 | H |
| ATOM | 224 | 2HD | ARG | 14 | -8.640 | 9.304 | 3.144 | 1.00 | 0.00 | H |
| ATOM | 225 | HE | ARG | 14 | -5.774 | 8.543 | 2.406 | 1.00 | 0.00 | H |
| ATOM | 226 | 1HH1 | ARG | 14 | -6.381 | 11.933 | 4.437 | 1.00 | 0.00 | H |
| ATOM | 227 | 2HH1 | ARG | 14 | -7.735 | 10.711 | 4.288 | 1.00 | 0.00 | H |
| ATOM | 228 | 1HH2 | ARG | 14 | -4.259 | 9.941 | 2.597 | 1.00 | 0.00 | H |
| ATOM | 229 | 2HH2 | ARG | 14 | -4.506 | 11.486 | 3.525 | 1.00 | 0.00 | H |
| ATOM | 230 | N | CYS | 15 | -8.170 | 5.034 | 1.363 | 0.00 | 0.00 | N |
| ATOM | 231 | CA | CYS | 15 | -7.079 | 4.245 | 0.743 | 0.00 | 0.00 | C |
| ATOM | 232 | C | CYS | 15 | -5.655 | 4.759 | 1.143 | 0.00 | 0.00 | C |
| ATOM | 233 | O | CYS | 15 | -5.259 | 5.883 | 0.814 | 0.00 | 0.00 | O |
| ATOM | 234 | CB | CYS | 15 | -7.334 | 4.257 | -0.778 | 0.00 | 0.00 | C |
| ATOM | 235 | SG | CYS | 15 | -8.884 | 3.429 | -1.256 | 0.00 | 0.00 | S |
| ATOM | 236 | H | CYS | 15 | -8.792 | 5.616 | 0.794 | 0.00 | 0.00 | H |
| ATOM | 237 | HA | CYS | 15 | -7.164 | 3.186 | 1.042 | 0.00 | 0.00 | H |
| ATOM | 238 | 1HB | CYS | 15 | -7.333 | 5.288 | -1.182 | 0.00 | 0.00 | H |
| ATOM | 239 | 2HB | CYS | 15 | -6.511 | 3.736 | -1.303 | 0.00 | 0.00 | H |
| ATOM | 240 | N | ILE | 16 | -4.902 | 3.917 | 1.872 | 1.00 | 0.00 | N |
| ATOM | 241 | CA | ILE | 16 | -3.499 | 4.208 | 2.301 | 1.00 | 0.00 | C |
| ATOM | 242 | C | ILE | 16 | -2.563 | 3.058 | 1.802 | 1.00 | 0.00 | C |
| ATOM | 243 | O | ILE | 16 | -2.787 | 1.881 | 2.109 | 1.00 | 0.00 | O |
| ATOM | 244 | CB | ILE | 16 | -3.362 | 4.466 | 3.848 | 1.00 | 0.00 | C |
| ATOM | 245 | CG1 | ILE | 16 | -3.997 | 3.381 | 4.774 | 1.00 | 0.00 | C |
| ATOM | 246 | CG2 | ILE | 16 | -3.880 | 5.877 | 4.225 | 1.00 | 0.00 | C |
| ATOM | 247 | CD1 | ILE | 16 | -3.464 | 3.357 | 6.218 | 1.00 | 0.00 | C |
| ATOM | 248 | H | ILE | 16 | -5.380 | 3.056 | 2.182 | 1.00 | 0.00 | H |
| ATOM | 249 | HA | ILE | 16 | -3.153 | 5.136 | 1.802 | 1.00 | 0.00 | H |
| ATOM | 250 | HB | ILE | 16 | -2.274 | 4.477 | 4.063 | 1.00 | 0.00 | H |

FIG. 5E

| | | Atom Name | Resi-due Name | Residue Sequence Number | X | Y | Z | | | |
|---|---|---|---|---|---|---|---|---|---|---|
| ATOM | 251 | 1HG1 | ILE | 16 | -5.099 | 3.490 | 4.779 | 1.00 | 0.00 | H |
| ATOM | 252 | 2HG1 | ILE | 16 | -3.827 | 2.376 | 4.343 | 1.00 | 0.00 | H |
| ATOM | 253 | 1HG2 | ILE | 16 | -3.687 | 6.125 | 5.285 | 1.00 | 0.00 | H |
| ATOM | 254 | 2HG2 | ILE | 16 | -3.394 | 6.668 | 3.624 | 1.00 | 0.00 | H |
| ATOM | 255 | 3HG2 | ILE | 16 | -4.969 | 5.964 | 4.060 | 1.00 | 0.00 | H |
| ATOM | 256 | 1HD1 | ILE | 16 | -3.945 | 2.557 | 6.809 | 1.00 | 0.00 | H |
| ATOM | 257 | 2HD1 | ILE | 16 | -2.373 | 3.171 | 6.247 | 1.00 | 0.00 | H |
| ATOM | 258 | 3HD1 | ILE | 16 | -3.652 | 4.308 | 6.749 | 1.00 | 0.00 | H |
| ATOM | 259 | N | CYS | 17 | -1.511 | 3.396 | 1.030 | 1.00 | 0.00 | N |
| ATOM | 260 | CA | CYS | 17 | -0.568 | 2.392 | 0.470 | 1.00 | 0.00 | C |
| ATOM | 261 | C | CYS | 17 | 0.877 | 2.602 | 1.011 | 1.00 | 0.00 | C |
| ATOM | 262 | O | CYS | 17 | 1.608 | 3.490 | 0.562 | 1.00 | 0.00 | O |
| ATOM | 263 | CB | CYS | 17 | -0.695 | 2.398 | -1.069 | 1.00 | 0.00 | C |
| ATOM | 264 | SG | CYS | 17 | -0.233 | 0.772 | -1.695 | 1.00 | 0.00 | S |
| ATOM | 265 | H | CYS | 17 | -1.430 | 4.391 | 0.798 | 1.00 | 0.00 | H |
| ATOM | 266 | HA | CYS | 17 | -0.878 | 1.380 | 0.777 | 1.00 | 0.00 | H |
| ATOM | 267 | 1HB | CYS | 17 | -1.734 | 2.590 | -1.399 | 1.00 | 0.00 | H |
| ATOM | 268 | 2HB | CYS | 17 | -0.072 | 3.185 | -1.536 | 1.00 | 0.00 | H |
| ATOM | 269 | N | THRC | 18 | 1.286 | 1.785 | 2.001 | 1.00 | 0.00 | N |
| ATOM | 270 | CA | THRC | 18 | 2.596 | 1.951 | 2.701 | 1.00 | 0.00 | C |
| ATOM | 271 | C | THRC | 18 | 3.762 | 1.236 | 1.943 | 1.00 | 0.00 | C |
| ATOM | 272 | OXT | THRC | 18 | 4.027 | 0.047 | 2.147 | 1.00 | 0.00 | O |
| ATOM | 273 | CB | THRC | 18 | 2.448 | 1.596 | 4.214 | 1.00 | 0.00 | C |
| ATOM | 274 | OG1 | THRC | 18 | 3.682 | 1.831 | 4.877 | 1.00 | 0.00 | O |
| ATOM | 275 | CG2 | THRC | 18 | 2.017 | 0.167 | 4.594 | 1.00 | 0.00 | C |
| ATOM | 276 | HN | THRC | 18 | 0.597 | 1.079 | 2.289 | 1.00 | 0.00 | H |
| ATOM | 277 | HA | THRC | 18 | 2.845 | 3.033 | 2.723 | 1.00 | 0.00 | H |
| ATOM | 278 | HB | THRC | 18 | 1.702 | 2.293 | 4.648 | 1.00 | 0.00 | H |
| ATOM | 279 | HG1 | THRC | 18 | 4.200 | 1.031 | 4.751 | 1.00 | 0.00 | H |
| ATOM | 280 | 1HG2 | THRC | 18 | 1.934 | 0.057 | 5.692 | 1.00 | 0.00 | H |
| ATOM | 281 | 2HG2 | THRC | 18 | 1.027 | -0.090 | 4.175 | 1.00 | 0.00 | H |
| ATOM | 282 | 3HG2 | THRC | 18 | 2.733 | -0.599 | 4.244 | 1.00 | 0.00 | H |
| TER. | | | | | | | | | | |

FIG. 5F

RTD1a

```
GACGGCTGCTGTTGCTACAGGAGACCCAGGACAGAGGACTGCTGTCTGCACTCTCTCTTC     60

ACTCTGCCTAACTTGAGGATCTGTCACTCCAGCCATGAGGACCTTCGCCCTCCTCACCGC    120
                                  M   R   T   F   A   L   L   T   A
CATGCTTCTCCTGGTGGCCCTGCACGCTCAGGCAGAGGCACGTCAGGCAAGAGCTGATGA    180
  M   L   L   V   A   L   H   A   Q   A   E   A   R   Q   A   R   A   D   E
AGCTGCCGCCCAGCAGCAGCCTGGAACAGATGATCAGGGAATGGCTCATTCCTTTACATG    240
  A   A   A   Q   Q   Q   P   G   T   D   D   Q   G   M   A   H   S   F   T   W
GCCTGAAAACGCCGCTCTTCCACTTTCAGAGTCAGCGAAAGGCTTGAGGTGCATTTGCAC    300
  P   E   N   A   A   L   P   L   S   E   S   A   K   G   L   R¹³ C¹⁴ L¹⁵ C¹⁶ T¹⁷
ACGAGGATTCTGCCGTTTGTTATAATGTCACCTTGGGTCCTGCGCTTTTCGTGGTTGACT    360
  R¹⁸ G¹ F² C³  R   L   L   stop
CCACCGGATCTGCTGCCGCTGAGCTTCCAGAATCAAGAAAAATATGCTCAGAAGTTACTT    420

TGAGAGTTAAAAGAAATTCTTGCTACTGCTGTACCTTCTCCTCAGTTTCCTTTTCTCATC    480

CCAAATAAATACCTTATCGC                                            500
```

FIG. 12A

RTD1b

```
GACCGCTGCTCTTGCTACAGGAGACCCGGGACAGAGGACTGCTGTCTGCCCTCTCTCTTC     60

ACTCTGCCTAACTTGAGGATCTGCCAGCCATGAGGACCTTCGCCCTCCTCACCGCCATGC    120
                                M   R   T   F   A   L   L   T   A   M   L
TTCTCCTGGTGGCCCTGCACGCTCAGGCAGAGGCACGTCAGGCAAGAGCTGATGAAGCTG    180
  L   L   V   A   L   H   A   Q   A   E   A   R   Q   A   R   A   D   E   A   A
CCGCCCAGCAGCAGCCTGGAGCAGATGATCAGGGAATGGCTCATTCCTTTACACGGCCTG    240
  A   Q   Q   Q   P   G   A   D   D   Q   G   M   A   H   S   F   T   R   P   E
AAAACGCCGCTCTTCCGCTTTCAGAGTCAGCGAGAGGCTTGAGGTGCCTTTGCAGACGAG    300
  N   A   A   L   P   L   S   E   S   A   R   G   L   R⁴ C⁵ L⁶ C⁷ R⁸ R⁹ G¹⁰
GAGTTTGCCAACTGTTATAAAGGCGTTTGGGGTCCTGCGCTTTTCGTGGTTGACTCTGCC    360
  V¹¹ C¹² Q   L   L   stop
GGATCTGCTGCCGCTGAGCTTCCAGAATCAAGAAAAATACGCTCAGAAGTTACTTTGAGA    420

GTTGAAAGAAATTCCTGTTACTCCTGTACCTTGTCCTCAATTTCCTTTTCTCATCCCAAA    480

TAAATACCTTCTCGC                                                 495
```

FIG. 12B

RTD1.1

```
GACGGCTGCTGTTGCTACAGGAGACCCAGGACAGAGGACTGCTGTCTGCACTCTCTCTTC        60
ACTCTGCCTAACTTGAGGATCTgtaagtaacacaaaacttaaacttttcctgtcgaggttt      120
gaacattgaagctgtgcccctaatctgacctgtgactcctgggccaccccagagagacct      180
agtgggtgaatcccctgctgtgcatttctgtctgaacctctgggggctgctgggagcatt      240
ggctaccagctcaattaatagagaaactcaaggaatttccttctaattacatgtgtccta      300
cttgacacatccaacagagacaacaatagctccttaaaacacccttttgtttggagagaa      360
gccaatccagatcctcggcctgttttcaatcaggttatttgttatttactattgagttg       420
tttgactgccttatgtatttagatatttacccttctaccacttaggatttgcaactatc      480
gtctttcattttctgggttgcttttcactcagttgattatttgtttgttggtttttga       540
cgtgcagatgctttagaggtcagtgcagccccacttgcctcttttcccatttattgcctg      600
tgtctttggtgtcatagcaaagatatcattaccaacatcaatgtcaaagcgtcatcttca      660
tatattcctctcgtcgttttatggtttcaggtctatgtttgggtcttcaatccatttgag      720
ttgatttgtgtatatagatatgataaggccacatgtatcaaacatcaaatcctaaggtgc      780
agacagagatatataccatttaatcttattcacatctctatagagctggaaacaaattt      840
ttggctgtagatgaacttttacctcgatatgtcagtgttcatttcacctatcatatgat       900
agggtcattgttctcttcacactggccctacaggaggctactcacccatgccttcggg       960
agtgtggtcaagcccttgatgcctcaataaatgactctttacttgataggaaatcatac     1020
ctgctgccagagtgtagacctacagagagtagtagggccatctgcaggaagagacatttg     1080
tcgcctgacctcattgaataaaatcactgctgttatcctttgctagaagagttaaaagta     1140
aatatttcgtaaagtgagaaacaggaatcctcatcatcatcctcatcaaaccagcacaga     1200
cactaaacatagagattcaaactagagtgaaagctgggagaccaaaagaagaaaacatgg     1260
acattgagaccaatgggatcccacacaatctccagtgaaatgcacacctcctctctctga     1320
gaaggttcaaggtttcctgtctctgagcctcctctctgcagacatagaaatccagactaa     1380
ctcctctctcccgacttgtccgctcctgctctgcctcttccagGTCACTCCAGCCATGAG     1440
GACCTTCGCCCTCCTCACCGCCATGCTTCTCCTGGTGGCCCTGCACGCTCAGGCAGAGGC     1500
ACGTCAGGCAAGAGCTGATGAAGCTGCCGCCCAGCAGCAGCCTGGAACAGATGATCAGGG     1560
AATGGCTCATTCCTTTACATGGCCTGAAAACGCCGCTCTTCCACTTTCAGgtgagacagg     1620
ccggcatgcagagctgcagggtctagagggatggatgggagacagagtcgggaatcgagt     1680
ctcagtggtccttgtcacctagatggcttcatttagcatctctgggccttggttttctca     1740
tctataaattgaatacagaaccaaataaatctagcaggtttctgtctataaagacttgag     1800
gcagctctgcctggagagtaaccattcttttattcctttacttccttaacgatccttca     1860
ctttagaaaatcaataaaattaaaaaataagacttgaaatcaacatatgtctgtgaaatt     1920
cagtaggtttaagatatgaagaaacagtctgctagttctttctggattcaaacaagtcat     1980
cttcattacatggataatatttgactgtatctatacaaccgtttctaagagtagagacaa     2040
gcctaagagtgcgttcaggtgtgtgtctgatggggcagaagcacaaaaatgaaagcaaat     2100
gagaataagtctcaaatcctgtatgaccagcactgctctgtgtatttattcttaatgact     2160
gaagttgttcatgctaccggccctaatgcagccgacatcactcattagctagcacatgac     2220
ttctccaggattcccttgccacccactgctgaccttctgatccatttacgatgctctct     2280
ctgtgttcccagAGTCAGCGAAAGGCTTGAGGTGCATTTGCACACGAGGATTCTGCCGTT     2340
TGTTATAATGTCACCTTGGGTCCTGCGCTTTTCGTGGTTGACTCCACCGGATCTGCTGCC     2400
GCTGAGCTTCCAGAATCAAGAAAAATATGCTCAGAAGTTACTTTGAGAGTTAAAAGAAAT     2460
TCTTGCTACTGCTGTACCTTCTCCTCAGTTTCCTTTTCTCATCCCAAATAAATACCTTCT     2520
CGC                                                            2523
```

FIG. 14A

RTD1.2

```
GACCGCTGCTCTTGCTACAGGAGACCCGGGACAGAGGACTGCTGTCTGCCCTCTCTCTTC      60
ACTCTGCCTAACTTGAGGATCTgtaagtaacacaaaacttaaacttttcctgtcgaggttt    120
gaacattgaagctgtgcacccaatctgacctgtgactcctgggccacccagagggacct     180
agtgggtgaatcccctgctgtgcatttctgtctgaacctctgggggctgctgggagcatt    240
ggctaccagctcaattaatagagaaactcaagaaattccttctacttacacgtgtccta    300
cttgacacgtccaacagagacaacaatagctccttaaaacacccttttatttggagagaa   360
gccgatcctgctcctcggcctatttttcaatcaggttatttcttatttgctactgagttg   420
tttgattgccttatgcatttagatgttcacccttctaccacttagggtttgcaactatt    480
gtctttcattttctgagttgcttttttcactcagttgattatttatttgttggtttggttt  540
tttgacgtgcatttgctttagaggtcagtgcagccccacttgtctcttttcccgtttatt   600
gcctgtgtctttggtgtcatagcaaagatatcattaccaacatcaatgtcaaagcattat   660
cttcatatgttcctctcgtcgtttacggtttcaggactatgtttgggtcttcaatccatt   720
ttgagttggtttgtgaaatagatatgataaagaccacatgtatcaaacatcaaatcctaa   780
ggtggagtacagtagatatataccattttcattcttattcatatctctatagagctgga    840
aatgaattttcagtgtagatgaaattttgaccttgatatcactgtgttcatttcccta     900
tcgcatgatagggtcattgtcctcttcacattggccctacaggaggctacacacctcat    960
gccttcatgagagtgatcatgcctatgatgcctgcaacaaatcactcttcacttgacagg   1020
aaattcatgcctgctgccagagtgtagacccatagagagtcgtggggccatctgaagaa    1080
aggagacatttgtatcctgaacttactgaacaaagcactgctgttatcctttggtagaac   1140
agtaaaaagtaaatatgtaatgaagtgagaaacaggagaaagatgccaggttcctcatct    1200
tcaccatcctctccatcagcacagacactaaacatagagattcaaactagagtgaaagct   1260
gggagagcaaaagaagaaaacatggacattgagaccaatgggatcccatacaatctccag   1320
tgaaatgcacagctcctctctctgagaaggttcaagatttcctgtctctgagcctttctct  1380
ctgcagacatagaaatccagactaactcctctctcccgacttgtctgctcctgctcttcc   1440
tcctccagGCCAGCCATGAGGACCTTCGCCCTCCTCACCGCCATGCTTCTCCTGGTGGCC    1500
CTGCACGCTCAGGCAGAGGCACGTCAGGCAAGAGCTGATGAAGCTGCCGCCCAGCAGCAG    1560
CCTGGAGCAGATGATCAGGGAATGGCTCATTCCTTTACACGGCCTGAAAACGCCGCTCTT    1620
CCGCTTTCAGgtgagacaggccggcatgcagagctacagggtctagagggatggatggga   1680
gacagagtcgggaatcgagtctcagtggtccatgtcacctagatggcttcatttagcatc   1740
tctgggccttggttttctcatctataaattgaatagagagccaaagaagtctaacaggtt   1800
ttctgtctataaagatttgaggcagctctgcctggagagtaaccattcttttattcccctt  1860
acttccttaatgatcccttcactttagagaatcaataaaattaaaaaataaaacttgaaa   1920
tcaagatatgtctgtgaaattcaagtaggtttaagacatgaagagacagtctgactagtt   1980
ctttctggattcaaacaagtcatcttcattacacggagaatatttgactgtatctataca   2040
accgtttctaagagtagagacaagcctaagagtgcattcaggtgtttgtgtttgatgggg   2100
cacaggcacaaaaatgagagcaaatgagaataagtctcaaatcctgtgtgaccagcacta   2160
ctctgtgtatttattcctactgactgaggttgttcatgctaccggcccgaatgcagctga   2220
catccctcattagctagcacatgacttctccaggattccctttgtcactcactgcagacc   2280
ttctgatccatttatgatgctttctctgtgtcccagAGTCAGCGAGAGGCTTGAGGTGC    2340
CTTTGCAGACGAGGAGTTTGCCAACTGTTATAAAGGCGTTTGGGGTCCTGCGCTTTTCGT    2400
GGTTGACTCTGCCGGATCTGCTGCCGCTGAGCTTCCAGAATCAAGAAAAATACGCTCAGA    2460
AGTTACTTTGAGAGTTGAAAGAAATTCCTGTTACTCCTGTACCTTGTCCTCAATTTCCTT    2520
TTCTCATCCCAAATAAATACCTTCTCGC                                    2548
```

FIG. 14B

```
CCTGGAACAGATGATCAGGGAATGGCTCATTCCTTTACATGGCCTGAAAACGCCGCTCTT    60
GGACCTTGTCTACTAGTCCCTTACCGAGTAAGGAAATGTACCGGACTTTTGCGGCGAGAA

CCACTTTCAGAGTCAGCGAAAGGCTTGAGGTGCATTTGCACACGAGGATTCTGCCGTTTG    120
GGTGAAAGTCTCAGTCGCTTTCCGAACTCCACGTAAACGTGTGCTCCTAAGACGGCAAAC

TTATAATGTCAC                                                    132
AATATTACAGTG
```

FIG. 15A

```
CCTGGAGCAGATGATCAGGGAATGGCTCATTCCTTTACACGGCCTGAAAACGCCGCTCTT    60
GGACCTCGTCTACTAGTCCCTTACCGAGTAAGGAAATGTGCCGGACTTTTGCGGCGAGAA

CCGCTTTCAGAGTCAGCGAGAGGCTTGAGGTGCCTTTGCAGACGAGGAGTTTGCCAACTG    120
GGCGAAAGTCTCAGTCGCTCTCCGAACTCCACGGAAACGTCTGCTCCTCAAACGGTTGAC

TTATAAGGCGT                                                     132
AATATTCCGCA
```

FIG. 15B

```
CCAGCCATGAGGACCTTCGCCCTCCTCACCGCCATGCTTCTCCTGGTGGCCCTGCACGCT    60
   M  R  T  F  A  L  L  T  A  M  L  L  L  V  A  L  H  A
CAGGCAGAGGCACGTCAGGCAAGAGCTGATGAAGCTGCCCAGCAGCCTGGAGCA          120
 Q  A  E  A  R  Q  A  R  A  D  E  A  A  A  Q  Q  P  G  A
GATGATCAGGGAATGGCTCATTCCTTTACATGGCCTGAAAACGCCCTCTTCCACTTTCA    180
 D  D  Q  G  M  A  H  S  F  T  W  P  E  N  A  L  P  L  S
GAGTCAGGCGAAAGGCTTGAGGTGCATTTGCACACGAGGATTCTGCCGTATGTTATAACGT 240
 E  S  Q  A  K  G  L  R  C  I  C  T  R  G  F  C  R  M  L  end
CGC                                                            243
```

ANTIMICROBIAL THETA DEFENSINS AND METHODS OF USING SAME

This application is a continuation of application Ser. No. 09/309,487, filed May 10, 1999, now U.S. Pat. No. 6,335,318.

This invention was made with government support under grant number AI22931 awarded by the National Institutes of Health. The government has certain rights in the invention.

BACKGROUND OF THE INVENTION

1. Field of the Invention

The present invention relates generally to antimicrobial agents and, more specifically, to cyclic theta defensin peptides and methods of using a theta defensin to reduce or inhibit microbial growth or survival.

2. Background Information

Infections by microorganisms, including bacteria, viruses and fungi, are a major cause of human morbidity and mortality. Although anyone can be a victim of such infection, the sick and elderly are particularly susceptible. For example, hospitalized patients frequently acquire secondary infections due to a combination of their weakened condition and the prevalence of microorganisms in a hospital setting. Such opportunistic infections result in increased suffering of the patient, increased length of hospitalization and, consequently, increased costs to the patient and the health care system. Similarly, the elderly, particularly those living in nursing homes or retirement communities, are susceptible to infections because of their close living arrangement and the impaired responsiveness of their immune systems.

Numerous drugs are available for treating infections by certain microorganisms. In particular, various bacterial infections have been amenable to treatment by antibiotics. However, the prolonged use of antibiotics since their discovery has resulted in the selection of bacteria that are relatively resistant to these drugs. Furthermore, few if any drugs are effective against microorganisms such as viruses. As a result, continuing efforts are being made to identify new and effective agents for treating infections by a variety of microorganisms.

The identification of naturally occurring compounds that act as antimicrobial agents has provided novel and effective drugs. Many organisms protect themselves by producing natural products that are toxic to other organisms. Frogs, for example, produce a class of peptides, magainins, which provide a defense mechanism for the frog against potential predators. Magainins have been purified and shown to have antimicrobial activity, thus providing a natural product useful for reducing or inhibiting microbial infections.

Natural products useful as antimicrobial agents also have been purified from mammalian organisms, including humans. For example, the defensins are a class of peptides that have been purified from mammalian neutrophils and demonstrated to have antimicrobial activity. Similarly, indolicidin is a peptide that has been isolated from bovine neutrophils and has antimicrobial activity, including activity against viruses, bacteria, fungi and protozoan parasites. Thus, naturally occurring compounds provide a source of drugs that are potentially useful for treating microbial infections.

Upon identifying naturally occurring peptides useful as antimicrobial agents, efforts began to chemically modify the peptides to obtain analogs having improved properties. Such efforts have resulted, for example, in the identification of indolicidin analogs which, when administered to an individual, have increased selectivity against the infecting microorganisms as compared to the individuals own cells. Thus, the availability of naturally occurring antimicrobial agents has provided new drugs for treating microbial infections and has provided a starting material to identify analogs of the naturally occurring molecule that have desirable characteristics.

Although such natural products and their analogs have provided new agents for treating microbial infections, it is well known that microorganisms can become resistant to drugs. Thus, a need exists to identify agents that effectively reduce or inhibit the growth or survival of microorganisms. Th e present invention satisfies this need and provides additional advantages.

SUMMARY OF THE INVENTION

The present invention relates to an isolated cyclic theta defensin peptide, which exhibits broad spectrum antimicrobial activity, and to theta defensin analogs. In general, a theta defensin or theta defensin analog has the amino acid sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8, wherein Xaa1 independently is Gly, Ile, Leu, Val or Ala; Xaa2 is Phe, Trp or Tyr; Xaa3 is Cys or Trp; Xaa4 independently is Arg or Lys; Xaa5 is Cys or Trp; Xaa6 is Cys or Trp; Xaa7 is Thr or Ser; and Xaa8 is Arg or Lys. Xaa1 can be linked through a peptide bond to Xaa8. Furthermore, crosslinks can be formed between Xaa3 and Xaa3, between Xaa5 and Xaa5, and between Xaa7 and Xaa7. For example, the invention provides theta defensin having the amino acid sequence Gly-Phe-Cys-Arg-Cys-Leu-Cys-Arg-Arg-Gly-Val-Cys-Arg-Cys-Ile-Cys-Thr-Arg (SEQ ID NO:1), wherein the Gly at position 1 (Gly-1) is linked through a peptide bond to Arg-18, and wherein disulfide bonds are present between Cys-3 and Cys-16, Cys-5 and Cys-14, and Cys-7 and Cys-12.

The invention also relates to methods of using a theta defensin or an analog thereof to reduce or inhibit microbial growth or survival in an environment capable of sustaining microbial growth or survival by contacting the environment with theta defensin. As such, the invention provides methods of reducing or inhibiting microbial growth or survival on a solid surface, for example, surgical instruments, hospital surfaces, and the like.

The invention further relates to methods for reducing or inhibiting microbial growth or survival in an individual, particularly a mammal such as a human. Thus, the invention provides methods of treating an individual suffering from a pathology characterized, at least in part, by microbial infection, by administering theta defensin or an analog thereof to the individual, thereby reducing the severity of the pathologic condition.

BRIEF DESCRIPTION OF THE DRAWINGS

FIG. 1A shows reverse phase HPLC (RP-HPLC) of peripheral blood leukocyte extracts. An α-defensin-enriched extract of 6×10⁶ leukocytes (91% PMNs) was fractionated by RP-HPLC on a 0.46×25 cm C-18 column equilibrated in 0.1% aqueous TFA and developed with a linear acetonitrile gradient (dotted line). RTD-1 eluted in the peak marked with an arrow. FIG. 1B shows analytical RP-HPLC of purified RTD-1. The purity of RTD-1 was assessed by RP-HPLC of RTD-1 obtained from the peak marked by an arrow in FIG.

1A on an analytical C-18 column developed with acetonitrile at 0.5% per min. FIG. 1C shows acid-urea polyacrylamide gel electrophoresis (PAGE). Samples analyzed were 30% acetic acid extracts, $2\times10^6$ cell equivalents, lane 1; methanol/water extracted phase, $1\times10^6$ cell equivalents lane 2; and 1 μg of RTD-1, lane 3. Samples were resolved on a 12.5% acid-urea polyacrylamide gel and stained with formalin-Coomassie blue.

FIG. 2A shows the amino acid sequence of the peptide chain, determined by Edman sequencing. The corresponding MALDI-TOF MS analysis of purified proteolytic fragments is also shown. Residues in parentheses were assigned based on MALDI-TOF MS data. Calculated MALDI-TOF MS values are in parentheses. The peptides shown in FIG. 2A (top to bottom) correspond to SEQ ID NOS:2–9, respectively. FIG. 2B shows a schematic of RTD-1 cyclized peptide backbone.

FIGS. 4A, 4B and 4C show the structure of RTD-1. FIG. 4A shows a schematic of the covalent structure of RTD-1 compared with that of circulin A, an antiviral peptide isolated from the plant *Chassalia parvifolia*. FIG. 4B shows a theoretical model of RTD-1 obtained by molecular dynamics and energy minimization in water. The model shows a high degree of structural similarity to porcine protegrin 1 (PG-1) for those residues defined in the PG-1 solution structure. FIG. 4C shows the alignment of the PG-1 and RTD-1 sequences and disulfide motifs.

FIGS. 5A–5F show the coordinates used to generate the molecular model shown in FIG. 4B.

FIG. 6A shows the scheme for solid phase peptide synthesis and cyclization entailed chain assembly, cleavage/deprotection, purification of the reduced linear chain, oxidation and cyclization. FIG. 6B shows co-elution of synthetic and natural RTD-1 on RP-HPLC and comigration on acid-urea PAGE (inset). FIG. 6C shows circular dichroic spectra of synthetic and natural RTD-1 determined in water, 10 mM sodium phosphate buffer, and methanol at a peptide concentration of 111 μg/ml (53.3 μM).

FIG. 9A shows incubation of *S. aureus* 502a with increasing concentrations of natural or synthetic peptide. Killing was quantified by colony counts. FIGS. 9B–9D show incubation of the indicated organisms with RTD-1 peptide: *Listeria monocytogenes* and *Staphylococcus aureus* (FIG. 9B); *Salmonella typhimurium* and *Escherichia coli* (FIG. 9C); and *Cryptococcus neoformans* and *Candida albicans* (FIG. 9D). The limit of detection (1 colony per plate) was equal to $1\times10^3$ colony forming units in the incubation mixture. FIG. 9E shows killing of *S. aureus* 502a with natural or synthetic RTD-1 supplemented with increasing concentrations of NaCl.

FIG. 11A shows cytospin preparations of peripheral blood buffy coat cells, fixed with 4% paraformaldehyde, incubated with anti-RTD-1 antiserum. Antibody was visualized as a glucose oxidase complex with nitroblue tetrazolium. Cells were counterstained with Nuclear Fast Red. FIG. 11B shows negative control incubation of buffy coat cells using anti-RTD-1 antiserum that was preabsorbed with synthetic acyclic RTD-1.

FIGS. 12A and 12B show RTD1a and RTD1b cDNAs. FIG. 12A shows full length cDNA sequence of RTD1a (SEQ ID NO:13) with the deduced amino acid sequence (SEQ ID NO:14). FIG. 12B shows full length cDNA sequence of RTD1b (SEQ ID NO:15) with the deduced amino acid sequence (SEQ ID NO:16). Underlined amino acids are found in RTD-1, and superscript numbers correspond to the residue numbering of RTD-1 shown in FIG. 2. The underlined sequences in FIG. 12A correspond to nucleotides 287 to 313 (SEQ ID NO:17) and amino acids 65 to 73 (SEQ ID NO:18) of RTD1a. The underlined sequences in FIG. 12B correspond to nucleotides 282 to 308 (SEQ ID NO:19) and amino acids 65 to 73 (SEQ ID NO:20) of RTD1b. ATG of the initiation methionines are in bold, as are the polyadenlation sites at the 3' ends of the sequences.

FIG. 13A shows covalent structures of mature RTD-1 (SEQ ID NO:1) and HNP-4 (SEQ ID NO:12). FIG. 13B shows amino acid sequences of precursors of RTD1a (SEQ ID NO:21), RTD1b (SEQ ID NO:22) and HNP-4 (SEQ ID NO:23). Identical amino acids are indicated with a period. In-frame stops in the coding sequence are indicated as "*". Hyphens are inserted to maximize sequence alignments. Shading is used to demarcate signal, pro-segment, mature peptide and untranslated regions.

FIGS. 14A and 14B show genomic sequences of RTD1a (FIG. 14A; SEQ ID NO:24) and RTD1b (FIG. 14B; SEQ ID NO:25). Exon sequences are in uppercase, intron sequences in lower case.

FIGS. 15A and 15B shows the DNA probes used for specific hybridization of RTD1a (FIG. 15A; top stand, SEQ ID NO:26; bottom strand, SEQ ID NO:30) and RTD1b (FIG. 15B; top strand, SEQ ID NO:27; bottom strand, SEQ ID NO:31).

FIG. 16 shows human theta defensin cDNA. The nucleotide sequence (SEQ ID NO:28) and deduced amino acid sequence (SEQ ID NO:29) are shown.

DETAILED DESCRIPTION OF THE INVENTION

Figure 1A:
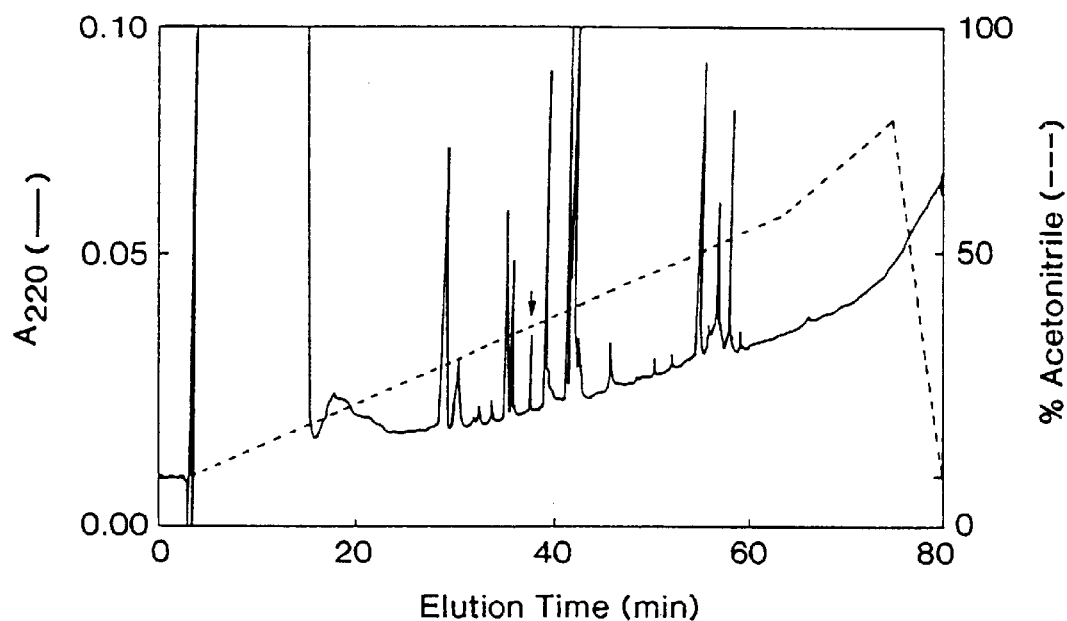
FIGS. 1A and 1B and 1C show purification of RTD-1.

The invention provides theta defensin peptides, or a functional fragment thereof, having antimicrobial activity.

The theta defensin peptides of the invention include theta defensin and theta defensin analogs, having the amino acid sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa5, wherein Xaa1 independently is an aliphatic amino acid; Xaa2 is and aromatic amino acid; Xaa3 is Cys or Trp; Xaa4 independently is Arg or Lys; Xaa5 is Cys or Trp; Xaa6 is Cys or Trp; Xaa7 is Thr or Ser; and Xaa8 is Arg or Lys. For example, Xaa1 can be an aliphatic amino acid such as Gly, Ile, Leu, Val or Ala and Xaa2 can be an aromatic amino acid such as Phe, Trp or Tyr. In general, a theta defensin is a cyclic peptide, wherein Xaa1 is linked through a peptide bond to Xaa8, and contains three intrachain crosslinks, which are formed between Xaa3 and Xaa3, between Xaa5 and Xaa5, and between Xaa7 and Xaa7. However, as disclosed herein, the invention also encompasses linear theta defensin precursors as well as peptide portions of a theta defensin.

As used herein, the term "independently," when used in reference to the selection of an amino acid at a position in the generic structure of a theta defensin, means that the selection of one amino acid at a position, for example, Xaa1 at position 1 of the theta defensin sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa5, has no influence on the selection, for example, of Xaa1 at position 6 or 10 or the like. For example, Xaa1 in can be Gly at position 1 and can be Leu at position 6.

A composition of the invention is exemplified by an isolated cyclic theta defensin, which lacks free amino and carboxyl termini and, therefore, is resistant to exopeptidases and is thus relatively stable to proteolytic degradation. The theta defensins of the invention exhibit broad spectrum antimicrobial activity. The exemplified theta defensin is an 18 amino acid cyclic peptide having the amino acid sequence Gly-Phe-Cys-Arg-Cys-Leu-Cys-Arg-Arg-Gly-Val-Cys-Arg-Cys-Ile-Cys-Thr-Arg (SEQ ID NO:1), wherein the Gly at position 1 (Gly-1) is linked through a peptide bond to Arg-18, and wherein three intrachain crosslinks are present due to disulfide bonds between Cys-3 and Cys-16, between Cys-5 and Cys-14, and between Cys-7 and Cys-12.

As used herein, the term "isolated," when used in reference to theta defensin, means that the peptide is relatively free of proteins, lipids, nucleic acids or other molecules it normally is associated with in a cell. In general, an isolated theta defensin peptide constitutes at least about 75% by weight of a sample containing the theta defensin, and usually constitutes about 90% of a sample, particularly about 95% of the sample or 99% or more. An isolated theta defensin can be obtained by isolation from a cell expressing the theta defensin (see Example I), can be chemically synthesized (see Example II), or can be expressed from a recombinant nucleic acid molecule (see Example V). Following chemical synthesis or recombinant expression, the theta defensin precursor peptide generally is linear and, therefore, can be further subjected to appropriate conditions for cyclizing the peptide and forming the intrachain crosslinks (see Example II).

The theta defensin peptide shown as SEQ ID NO:1 constitutes the first member of a new class of defensins and is the basis for constructing theta defensin analogs as disclosed herein. Previously described defensins are cationic, arginine-rich peptides having 29 to 42 amino acids and containing three disulfide bonds (see Lehrer et al., *Cell* 64:229–230 (1991); Lehrer and Ganz, *Current Opin. Immunol.* 11:23–27 (1999)). The β defensins, for example, contain 38 to 42 amino acids and have a net charge of +4 to +10 (see U.S. Pat. No. 5,459,235, issued Oct. 17, 1995, which is incorporated herein by reference). The disulfide bonds in β defensins are formed in a characteristic pattern between the first and fifth Cys residues, the second and fourth Cys residues, and the third and sixth Cys residues. In addition, some β defensins contain a pyroglutamate residue at the amino terminus (U.S. Pat. No. 5,459,235, supra, 1995).

Defensins and defensin-like peptides are endogenously expressed in various organisms. In mammals, defensins generally are expressed in neutrophils, macrophages and intestinal cells (see Lehrer et al., supra, 1991; Lehrer and Ganz, supra, 1999). Defensins can exhibit potent antimicrobial activity against a broad spectrum of microorganisms, including gram negative and gram positive bacteria, fungi, protozoans such as Acanthamoeba and Giardia, enveloped viruses such as herpes simplex viruses and human immunodeficiency viruses, and helminths. Defensins also have other properties, including chemotactic activity for human monocytes and the ability to interfere with adrenocorticotropin binding to its receptor (see Lehrer et al., supra, 1991).

A new class of defensins, termed theta defensins, is disclosed herein. Theta defensins have been classified as members of the defensin family of peptides based on their cationicity, arginine-rich composition and the presence of three intrapeptide disulfide bonds, as well as their broad spectrum antimicrobial activity. However, theta defensins are distinguishable from previously described defensins in that theta defensins are cyclic peptides, which lack a free amino or carboxyl terminus, and are shorter than previously described defensins.

The theta defensins are exemplified by the peptide shown as SEQ ID NO:1, which contains 18 amino acids, wherein the amino terminus of the first amino acid (Gly) is linked to the carboxyl terminus of the last amino acid (Arg) through a peptide bond, and wherein disulfide bonds are formed between Cys-3 and Cys-16, Cys-5 and Cys-14, and Cys-7 and Cys-12. For convenience of discussion, reference to an amino acid position in a theta defensin, or an analog thereof, is made with respect to the amino acid position in the linear form of theta defensin shown as SEQ ID NO:1 or of the theta defensin sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa5. As such, the amino acids are referred to as positions 1 through 18, starting with the Gly residue in (position 1; SEQ ID NO:1) and ending with Arg (position 18).

A theta defensin having the amino acid sequence of SEQ ID NO:1 can be obtained by purification of the native peptide from a natural source (see Example I). A theta defensin having the amino acid sequence of SEQ ID NO:1, or of the theta defensin sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa5, also can be chemically synthesized using routine methods of solid phase synthesis (see Example II) or can be expressed from a recombinant nucleic acid molecule encoding the theta defensin (see Example V).

In general, a precursor theta defensin is obtained following chemical synthesis of the peptide, since the newly synthesized peptide is not cyclized and does not contain the appropriate intrachain crosslinking. Similarly, expression of a recombinant nucleic acid molecule encoding a theta defensin generally results in the production of a precursor theta defensin peptide, unless the peptide is expressed in a cell that can effect formation of the appropriate bonds. Accordingly, the term "precursor," when used in reference to a theta defensin peptide, means a form of the peptide that lacks a peptide bond between the amino terminal and carboxyl terminal amino acids or lacks at least one of the three disulfide bonds characteristic of a theta defensin. Such precursor peptides can be converted into a mature cyclic theta defensin containing, for example, one, two or three disulfide bonds by exposing the precursor peptide to the appropriate conditions for effecting formation of the intrapeptide crosslinks, for example, the conditions disclosed in Example II. However, as disclosed herein, precursor theta defensins also are contemplated within the present invention.

A theta defensin or theta defensin analog can be prepared by solid phase methods (Example II). Theta defensin analogs, which are encompassed within SEQ ID NO:5, are synthesized based on SEQ ID NO:1, but substituting one or more amino acids of SEQ ID NO:1 as desired, particularly by incorporating conservative amino acid substitutions. Such conservative amino acid substitutions are well known and include, for example, the substitution of an amino acid having a small hydrophobic side chain with another such amino acid (for example, Ala for Gly) or the substitution of one basic residue with another basic residue (for example, Lys for Arg). Similar conservative amino acid substitutions in other antimicrobial peptides such as indolicidin resulted in the production of indolicidin analogs that maintained their broad spectrum antimicrobial activity (see U.S. Pat. No. 5,547,939, issued Aug. 20, 1996, which is incorporated herein by reference). Thus, a theta defensin analog having, for example, a substitution of Leu-6 with a Val, Ile or Ala residue, or a substitution of Arg-8 or Arg-9 or Arg-13 or Arg-18 with a Lys residue similarly can be expected to maintain broad spectrum antimicrobial activity.

A theta defensin analog also can have substitutions of the cysteine residues involved in a disulfide bond, with amino acids that can form an intrachain crosslink, for example, with tryptophan residues, which can form a di-tryptophan crosslink. Similarly to naturally occurring indolicidin, which is a linear antimicrobial peptide, indolicidin analogs having an intrachain di-tryptophan crosslink also have antimicrobial activity. Furthermore, substitution of the Trp residues involved in the di-tryptophan crosslink in an indolicidin analog with Cys residues results in an indolicidin analog that has an intrachain disulfide crosslink and exhibits broad spectrum antimicrobial activity. By analogy to such indolicidin analogs, a theta defensin analog can contain, in place of one or more of the characteristic disulfide bonds, one or more corresponding di-tryptophan, lactam or lanthionine crosslinks. For example, a crosslink in a theta defensin analog can be formed, for example, between two Trp residues, which form a di-tryptophan crosslink. In addition, a crosslink can be a monosulfide bond formed by a lanthionine residue. A crosslink also can be formed between other amino acid side chains, for example, a lactam crosslink formed by a transamidation reaction between the side chains of an acidic amino acid and a basic amino acid, such as between the γ-carboxyl group of Glu (or β-carboxyl group of Asp) and the ε-amino group of Lys; or can be a lactone produced, for example, by a crosslink between the hydroxy group of Ser and the γ-carboxyl group of Glu (or β-carboxyl group of Asp); or a covalent bond formed, for example, between two amino acids, one or both of which have a modified side chain.

The invention additionally provides a theta defensin peptide, or a functional fragment thereof, having the amino acid sequence Xaa1-Xaa2-Xaa9-Xaa4-Xaa10-Xaa1-Xaa11-Xaa4-Xaa4-Xaa1-Xaa1-Xaa12-Xaa4-Xaa13-Xaa1-Xaa14-Xaa7-Xaa8, wherein Xaa1 independently is an liphatic amino acid such as Gly, Ile, Leu, Val or Ala; Xaa2 is an aromatic amino acid such as Phe, Trp or Tyr; Xaa4 independently is Arg or Lys; Xaa7 is Thr or Ser; Xaa8 is Arg or Lys; Xaa9 is Glu, Asp, Lys or Ser; Xaa10 is Glu, Asp, Lys or Ser; Xaa11 is Glu, Asp, Lys or Ser; Xaa12 is Glu, Asp, Lys or Ser; Xaa13 is Glu, Asp, Lys or Ser; Xaa14 is Glu, Asp, Lys or Ser. In such a theta defensin peptide, an intrachain crosslink can be formed between two amino acids, Xaa9 and Xaa14; Xaa10 and Xaa13; or Xaa11 and Xaa12, which correspond to the same position as disulfide crosslinks in natural theta defensin. The intrachain crosslink can be, for example, a lactam or lactone.

In theta defensin peptides having less than three crosslinks, as found in native theta defensin, the amino acids at the positions corresponding to the native crosslinks, amino acids Xaa3, Xaa5 and Xaa6 in SEQ ID NO:1, can be modified. For example if positions Xaa3 are disulfide crosslinked, the amino acids at position Xaa5 and Xaa6 can be non cysteine residues, for example, a hydrophobic amino acid such as Tyr, Val, Ile, Leu, Met, Phe or Trp; a small amino acid such as Gly, Ser, Ala, or Thr; or a large polar amino acid such as Asn or Gln.

If desired, a theta defensin analog of the invention can have one or more amino acid deletions or additions as compared to SEQ ID NO:1, again, by analogy to indolicidin analogs, which can have a carboxyl terminal amino acid deletion or as many as five amino terminal amino acid deletions, yet still maintain broad spectrum antimicrobial activity. Thus, it can be expected that theta defensin analogs having one or a few deletions or additions at selected positions in the theta defensin sequence also will maintain broad spectrum antimicrobial activity and, as such, are considered functional fragments of a theta defensin. As used herein, a "functional fragment" when used in reference to a theta defensin is a portion of a theta defensin that still retains some or all of the antimicrobial activity of a theta defensin. The antimicrobial activity of a theta defensin analog, or a functional fragment thereof, containing one or more amino acid substitutions, deletions or additions as compared to SEQ ID NO:1 can be confirmed using assays as disclosed herein (Example III) or otherwise known in the art.

As used herein, the term "amino acid" is used in its broadest sense to mean the naturally occurring amino acids as well as non-naturally occurring amino acids, inc luding amino acid analogs. Thus, reference herein to an amino acid includes, for example, naturally occurring proteogenic (L)-amino acids, as well as (D)-amino acids, chemically modified amino acids such as amino acid analogs, naturally occurri ng non-proteogenic amino acids such as norleucine, and chemically synthesized compounds having properties known in the art to be characteristic of an amino acid. As used herein, the term "proteogenic" indicates that the amino acid can be incorporated into a p rotein in a cell through a metabolic pathway.

Theta defensin having the a mino acid sequence of SEQ ID NO:1 was chemically synthesized as a linear precursor peptide using solid phase Fmoc chemistry (see Example II). The linear peptide was subjected to reducing conditions, then oxidized to allow formation of the disulfide bonds, and treated with ethylenediaminecarbodiimide to cyclize the peptide. The synthesized cyclic theta defensin was characterized by reverse phase-high performance liquid chromatography (RP-HPLC), MALDI-TOF mass spectrometry and circular dichroism (CD) and comigrated with native theta defensin by acid-urea PAGE (Example II). The synthetic cyclic theta defensin also demonstrated broad spectrum antimicrobial activity (see Example III).

The invention additionally provides a method of preparing theta defensin. The method of synthesis includes the steps of synthesizing a linear peptide of an amino acid sequence corresponding to the amino acid sequence of theta defensin, forming one or more crosslink bonds within the linear peptide, and cyclizing the peptide by linking the carboxyl and amino termini to form a cyclic peptide. The crosslink formed can be a disulfide, lanthionine, lactam or lactone. The cysteine residues used in the linear peptide can be in a pre-formed activated ester form. If a disulfide crosslink is formed between two cysteines, the crosslink can be formed by oxidation. The formation of a peptide bond between the amino and carboxyl termini can be advantageously mediated by placing the carboxyl terminus and amino terminus of the linear peptide each approximately the same number of amino acids from the nearest cysteine.

The cyclization step can be performed with ethylenediaminecarbodiimide and N-hydroxybenzotriazole, for example, 60 equivalents and 20 equivalents, respectively, in a solvent. The synthesis can be performed in dimethylsulfoxide as the solvent.

Cyclized versions of the theta defensin peptides of the invention are resistant to exo-peptidases such as aminopeptidases and carboxypeptidases because there is no amino or carboxyl terminus to serve as a substrate for the exopeptidases. The invention further provides a method of enhancing protease resistance of a peptide by synthesizing a peptide, wherein the amino-terminal amino acid and carboxyl-terminal amino acid of the peptide are positioned by intrachain crosslinks and whereby a peptide bond is formed between the amino-terminal and carboxyl-terminal amino acids.

An advantage of using chemical synthesis to prepare a theta defensin is that (D)-amino acids can be substituted for (L)-amino acids, if desired. The incorporation of one or more (D)-amino acids into a theta defensin analog can confer, for example, additional stability of the peptide in vitro or, particularly, in vivo, since endogenous endoproteases generally are ineffective against peptides containing (D)-amino acids. Naturally occurring antimicrobial peptides that have been chemically synthesized to contain (D)-amino acids maintain their antimicrobial activity (Wade et al., *Proc. Natl. Acad. Sci. USA* 87:4761–4765 (1990), which is incorporated herein by reference).

If desired, the reactive side group of one or more amino acids in a theta defensin can be modified or amino acid derivatives can be incorporated into the peptide (see, for example, *Protein Engineering: A practical approach* (IRL Press 1992); Bodanszky, *Principles of Peptide Synthesis* (Springer-Verlag 1984), each of which is incorporated herein by reference). Selective modification of a reactive group, other than those involved in formation of the three intrachain crosslinks characteristic of a defensin, can impart desirable characteristics upon a theta defensin analog, although modifications that allow the formation of intrachain crosslinks at the appropriate positions also an be effected. The choice of including such a modification is determined, in part, by the characteristics required of the peptide. Such modifications can result, for example, in theta defensin analogs having greater antimicrobial selectivity or potency than naturally occurring theta defensin (SEQ ID NO:1).

The theta defensins of the invention are polypeptides having antimicrobial activity. As used herein, the term "polypeptide" when used in reference to a theta defensin is intended to refer to a peptide or polypeptide of two or more amino acids. The term is similarly intended to refer to derivatives, analogues and functional mimetics thereof. For example, derivatives can include chemical modifications of the polypeptide such as alkylation, acylation, carbamylation, iodination, or any modification which derivatives the polypeptide. Analogues can include modified amino acids, for example, hydroxyproline or carboxyglutamate, and can include amino acids that are not linked by peptide bonds. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide the antimicrobial function of a theta defensin, are included within the meaning of a theta defensin derivative. All of these modifications are included within the term "polypeptide" so long as the polypeptide retains its antimicrobial function.

A theta defensin can incorporate polypeptide derivatives. Peptide derivatives are well known in the art (see, for example, U.S. Pat. No. 5,804,558, issued Sep. 8, 1998). For example, certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har).

In peptides of the invention, one or more amide linkages (—CO—NH—) can be replaced with another linkage which is an isostere such as —CH$_2$NH—, —CH$_2$S—, —CH$_2$CH$_2$, —CH═CH— (cis and trans), —COCH$_2$—, —CH(OH) CH$_2$— and —CH$_2$SO—. This replacement can be made by methods known in the art (see, for example, Spatola, *Vega Data* Vol. 1, Issue 3, (1983); Spatola, in *Chemistry and Biochemistry of Amino Acids Peptides and Proteins,* Weinstein, ed., Marcel Dekker, New York, p. 267 (1983); Morley, J. S., *Trends Pharm. Sci.* pp. 463–468 (1980); Hudson et al., *Int. J. Pept. Prot. Res.* 14:177–185 (1979); Spatola et al., *Life Sci.* 38:1243–1249 (1986); Hann, *J. Chem. Soc. Perkin Trans. I* 307–314 (1982); Almquist et al., *J. Med. Chem.* 23:1392–1398 (1980); Jennings-White et al., *Tetrahedron Lett.* 23:2533 (1982); Szelke et al., EP 45665 (1982); Holladay et al., *Tetrahedron Lett.* 24:4401–4404 (1983); and Hruby, *Life Sci.* 31:189–199 (1982)).

In addition to polypeptide derivatives of a theta defensin, the invention additionally provides a chemical mimetic of a theta defensin peptide. As described above, mimetics contain chemical functional groups that mimic the function of a theta defensin. Such a mimetic chemical can orient functional groups on a theta defensin peptide sufficient for antimicrobial activity. A mimetic places the functional chemical moieties in a spatial orientation and constrained structure so that the chemical function is maintained in three-dimensional space. Thus, a mimetic orients chemical functional groups that provide the theta defensin function of antimicrobial activity in an orientation that mimics the structure of a theta defensin.

As disclosed herein, a molecular model of a theta defensin has been determined (Example III). Using the molecular model of theta defensin, one skilled in the art can identify a chemical such as a peptidomimetic. As used herein, the term "peptidomimetic" is used broadly to mean a peptide-like molecule that has a similar structure and activity as a theta defensin. With respect to the theta defensin peptides of the invention, peptidomimetics, which include chemically modified peptides, peptide-like molecules containing non-naturally occurring amino acids, peptoids and the like, have the antimicrobial activity upon which the peptidomimetic is derived (see, for example, "Burger's Medicinal Chemistry and Drug Discovery" 5th ed., vols. 1 to 3 (ed. M. E. Wolff; Wiley Interscience 1995)). Peptidomimetics provide various advantages over a peptide, including that a peptidomimetic can be more stable during passage through the digestive tract and, therefore, useful for oral administration.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a theta defensin peptide. Another database, the Available Chemicals Directory (Molecular Design Limited, Information Systems; San Leandro Calif.), contains about 100,000 compounds that are commercially available and also can be searched to identify potential peptidomimetics of a theta defensin peptide.

As used herein, the term "antimicrobial selectivity" refers to the relative amount of antimicrobial activity of theta defensin, or a theta defensin analog, against a microorganism as compared to its activity against the environment to which it is administered, particularly its activity against normal cells in a treated individual. For example, a theta defensin analog that is characterized by having antimicrobial activity that is equivalent to native theta defensin, but having decreased hemolytic activity as compared to native theta defensin, is considered to have greater antimicrobial selectivity than native theta defensin.

As disclosed herein, theta defensin (SEQ ID NO:1) and analogs thereof have broad spectrum antimicrobial activity (see Example III). As used herein, the term "broad spectrum," when used in reference to the antimicrobial activity of theta defensin or an analog thereof, refers to the ability of the peptide to reduce or inhibit the survival or proliferative ability of various viruses, prokaryotic and eukaryotic microorganisms. For example, theta defensin (SEQ ID NO:1) and analogs thereof can exhibit antimicrobial activity against protozoans such as Giardia lamblia, Chlamydia sp. and Acanthamoeba sp.; viruses, particularly enveloped viruses such as herpes simplex virus and HIV-1; fungi such as Cryptococcus and Candida; various genera of gram negative and gram positive bacteria, including Escherichia, Salmonella and Staphylococcus and Listeria; and parasitic helminths such as liver flukes. Antimicrobial activity can occur through "microbicidal inhibition," which refers to the ability of a theta defensin to reduce or inhibit the survival of a microorganism by killing or irreversibly damaging it, or through "microbistatic inhibition," which refers to the ability of the theta defensin to reduce or inhibit the growth or proliferative ability of a target microorganism without necessarily killing it.

A precursor theta defensin or theta defensin analog can be expressed from a recombinant nucleic acid molecule encoding the peptide. Thus, the invention also provides isolated nucleic acid molecules encoding a theta defensin or theta defensin analog having the sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa5. For example, the invention provides an isolated nucleic acid molecule encoding the linear form of SEQ ID NO:1, which is a precursor of the cyclic theta defensin peptide.

As used herein, the term "isolated," when used in reference to a nucleic acid molecule, means the nucleic acid molecule is relatively free of proteins, lipids, nucleic acids or other molecules it normally is associated with in a cell. In general, an isolated nucleic acid molecule encoding a theta defensin constitutes at least about 75% by weight of a sample containing the nucleic acid molecule, and usually constitutes about 90% of a sample, particularly about 95% of the sample or more. It is recognized, however, that an isolated nucleic acid molecule encoding a theta defensin can be contained in a vector. For purposes of the present definition of "isolated," vector DNA is not considered to be part of a sample when determining the degree of isolation of the nucleic acid molecule encoding the theta defensin, since the encoding nucleic acid molecule generally can be readily purified from the vector. An isolated nucleic acid molecule encoding a theta defensin can be chemically synthesized or can be cloned from a cell that contains a theta defensin gene or encodes a theta defensin mRNA, which can be converted to a cDNA.

An isolated nucleic acid molecule of the invention, which encodes a precursor theta defensin, can be prepared by chemical synthesis, based on the disclosed theta defensin amino acid sequence and knowledge in the art of codons encoding each amino acid. Thus, a nucleic acid molecule encoding SEQ ID NO:1, for example, can be synthesized by the steps of 1) selecting one of the four codons for Gly, 2) linking to the Gly encoding triplet one of the two codons for Phe, 3) linking to the Gly-Phe encoding hexamer one of the two codons for Cys, and so forth until a complete coding sequence has been synthesized. Since a nucleic acid sequence encoding SEQ ID NO:1 only is about 54 nucleotides in length (60 nucleotides if an initiator methionine and a STOP codon are included), synthesis of the sequence readily can be prepared using routine methods and, if desired, can be purchased from a commercial source. Similarly, nucleic acid molecules encoding theta defensin analogs can be synthesized based on the amino acid sequence of the analog.

Theta defensin cDNA was cloned from rhesus macaque bone marrow mRNA using 3' RACE with degenerate primers (see Example V). RTD1 is encoded by two similar cDNAs, termed RTD1a (SEQ ID NO:13) and RTD1b (SEQ ID NO:15), each of which contains 9 of the 18 amino acid residues in the mature RTD-1 peptide (see Example V and FIG. 12). The cDNAs encode separate peptides, which become cyclized by formation of peptide bonds that join the two peptides. The use of two genes to encode separate prepropeptides that are processed to form a cyclized peptide has not been previously described.

The invention additionally provides a nucleic acid molecule encoding the genomic DNA for rhesus macaque theta defensin RTD1a (SEQ ID NO:24) and RTD1b (SEQ ID NO:25) (see Example V and FIG. 14). The invention further provides a nucleic acid molecule encoding a human theta defensin (SEQ ID NO:28), which corresponds to a human theta defensin cDNA (FIG. 16). The human theta defensin peptide region corresponds to amino acid residues 65 to 73 in the precursor (amino acids RCICTRGFC; SEQ ID NO:18). In addition, the invention provides highly specific probes for RTD1a (SEQ ID NO:26) and RTD1b (SEQ ID NO:27).

Additional nucleic acid molecules encoding theta defensin can also be cloned from other mammalian cells. For example, degenerate oligonucleotide probes can be prepared based on the amino acid sequence of theta defensin (SEQ ID NO:1) and used to screen a cDNA or genomic DNA library to obtain cloned nucleic acid molecules encoding the theta defensin, as described in Example V. The peptide of SEQ ID NO:1 originally was isolated from leukocytes of Rhesus macaques. Thus, a DNA library prepared from leukocytes from other organisms can be screened to identify and clone a nucleic acid molecule encoding the theta defensin. Previously described defensins from various species share substantial amino acid sequence homology (see Lehrer et al., supra, 1991), and theta defensins also are likely to be relatively highly conserved. As disclosed herein, theta defensins of rhesus macaque and human are very similar (see Example V). Accordingly, a DNA library, which can be a genomic library or a cDNA library, prepared from cells of any mammal, for example, from leukocytes, can be screened using degenerate oligonucleotide probes to obtain a nucleic acid molecule encoding a theta defensin.

The skilled artisan will recognize that, in order to effectively screen a DNA library using oligonucleotide probes based on SEQ ID NO:1, the oligonucleotides should reflect a relatively conserved portion of the encoded peptide and should comprise the least degenerate codons. Thus, for screening a human nucleic acid library, for example, the artisan will recognize that oligonucleotide probes preferably are prepared based on a region of the monkey theta defensin sequence that likely is conserved among species, for example, a probe based on Arg-4 to Arg-9 or Arg-4 to Cys-12 of SEQ ID NO:1 (numbering according to FIG. 4A). Hybridization conditions such as those described, for example, in Example V can be used to obtain nucleic acid molecules encoding theta defensins from other species.

Oligonucleotide probes can be used to screen a DNA library using hybridization methods, including the polymerase chain reaction. Hybridization conditions are selected based, for example, on the length and nucleotide composition of the probes (or PCR primers) and can be determined empirically or estimated using formulas for calculating such conditions (see, for example, Sambrook et al., *Molecular Cloning: A laboratory manual* (Cold Spring Harbor Laboratory Press 1989), which is incorporated herein by reference; see chapter 11). Thus, the invention further provides oligonucleotide sequences comprising a portion of the coding sequence of a theta defensin, particularly of SEQ ID NO:1.

A nucleic acid molecule encoding a precursor theta defensin or analog thereof can be cloned into an appropriate vector, particularly an expression vector, and the encoded peptide can be expressed in a host cell or using an in vitro transcription/translation reaction, thereby providing a means to obtain large amounts of the theta defensin. Thus, the invention provides vectors containing a nucleic acid molecule encoding a theta defensin precursor, as well as host cells that can maintain the vectors and, if desired, allow expression of the theta defensin encoded by the nucleic acid molecule contained in the vector. Vector and host cell systems are well known in the art and commercially available.

The invention also provides antibodies that specifically bind a theta defensin. As used herein, the term "antibody" is used in its broadest sense to include polyclonal and monoclonal antibodies, as well as antigen binding fragments of such antibodies. With regard to an anti-theta defensin antibody of the invention, the term "antigen" means a native or synthesized theta defensin, including a peptide portion of the theta defensin, that can, but need not, be cyclized or contain intrachain crosslinks. An anti-theta defensin antibody, or antigen binding fragment of such an antibody, is characterized by having specific binding activity for a theta defensin or a peptide portion thereof of at least about $1 \times 10^5$ $M^{-1}$. Thus, Fab, F(ab')$_2$, Fd and Fv fragments of an anti-theta defensin antibody, which retain specific binding activity for a theta defensin, are included within the definition of an antibody.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering,* 2d ed. (Oxford University Press 1995); each of which is incorporated herein by reference).

Anti-theta defensin antibodies specific for theta defensin have been generated by conjugating acyclic theta defensin, which was oxidized but not cyclized, to ovalbumin (see Example IV). Additional anti-theta defensin antibodies can be raised using a theta defensin immunogen such as an isolated theta defensin having the amino acid sequence of SEQ ID NO:1, which can be prepared from natural sources or produced recombinantly, or a peptide portion of the theta defensin. A non-immunogenic theta defensin peptide or portion thereof can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane (supra, 1988).

An anti-theta defensin antibody is useful, for example, for determining the presence or level of a theta defensin in a tissue sample, which can be a lysate or a histological section, or for cloning a nucleic acid molecule encoding a theta defensin from an appropriate expression library. An anti-theta defensin antibody also can be used to substantially purify theta defensin from a sample, for example, following expression of the theta defensin from a recombinant nucleic acid molecule. In addition, an anti-theta defensin antibody raised against a linear form of the theta defensin or against a peptide portion of the theta defensin can be used to screen an expression library, for example, a lambda gt11 library, to identify a clone containing a cDNA encoding the theta defensin.

A theta defensin peptide or an anti-theta defensin antibody can be labeled so as to be detectable using methods well known in the art (Hermanson, "Bioconjugate Techniques" (Academic Press 1996), which is incorporated herein by reference; Harlow and Lane, 1988; chap. 9). For example, the peptide or antibody can be labeled with various detectable moieties including a radiolabel, an enzyme, biotin or a fluorochrome. Reagents for labeling a peptide or antibody can be included in a kit containing the peptide or antibody or can be purchased separately from a commercial source. Thus, the invention further provides a kit, which contains a theta defensin or an anti-theta defensin antibody or both. Such a kit also can contain a reaction cocktail that provides the proper conditions for performing an assay, for example, an ELISA or other immunoassay for determining the level of expression of a theta defensin in a sample, and can contain control samples that contain known amounts of a theta defensin and, if desired, a second antibody specific for the anti-theta defensin antibody. Where the kit is to be used for an immunoassay, it can include a simple method for detecting the presence or amount of a theta defensin in a sample that is bound to the antibody.

Methods for raising polyclonal antibodies, for example, in a rabbit, goat, mouse or other mammal, are well known in the art. In addition, monoclonal antibodies can be obtained using methods that are well known and routine in the art (Harlow and Lane, supra, 1988). Essentially, spleen cells from a mouse immunized, for example, with theta defensin having the amino acid sequence of SEQ ID NO:1 can be fused to an appropriate myeloma cell line such as SP/02 myeloma cells to produce hybridoma cells. Cloned hybridoma cell lines can be screened using labeled theta defensin to identify clones that secrete anti-theta defensin monoclonal antibodies. Hybridomas expressing anti-theta defensin monoclonal antibodies having a desirable specificity and affinity can be isolated and utilized as a continuous source of the antibodies, which are useful, for example, for preparing standardized kits as described above. Similarly, a recombinant phage that expresses, for example, a single chain anti-theta defensin antibody also provides a monoclonal antibody that can used for preparing standardized kits.

A theta defensin or analog thereof having antimicrobial activity can be applied to an environment capable of sustaining the survival or growth of a microorganism or to an environment at risk of supporting such survival or growth, thus providing a means for reducing or inhibiting microbial growth or survival. Accordingly, the invention relates to methods of using a theta defensin or a theta defensin analog to reduce or inhibit microbial growth by contacting an environment capable of sustaining microbial growth or survival with the antimicrobial peptide.

As used herein, reference to "an environment capable of sustaining survival or growth of a microorganism" means a gaseous, liquid or solid material, including a living organism, in or upon which a microorganism can live or propagate. In view of the broad range of environments that allow the survival or growth of microorganisms as diverse, for example, as viruses, bacteria, fungi, protozoans and helminths, and further in view of the disclosed effectiveness of a theta defensin against a broad spectrum of such microorganisms, the range of such environments that can be treated using a method of the invention necessarily is broad and includes, for example, a tissue or bodily fluid of an organism such as a human; a liquid such as water or an aqueous solution such as contact lens solution or eyewash solution; a food such as a food crop, a food product or a food extract; and an object such as the surface of an instrument used, for example, to prepare food or to perform surgery; and a gas such as that used for anesthetization in preparation for surgery.

A method of the invention encompasses administering to the environment an effective amount of a theta defensin or analog thereof such that the antimicrobial peptide can contact a microorganism in the environment, thereby reducing or inhibiting the ability of the microorganism to grow or survive. A theta defensin can be used in a variety of procedures for reducing or inhibiting the survival or growth of microorganisms, including the microbicidal inhibition of survival of a microorganism as well as the microbistatic inhibition of growth. As such, a theta defensin can be used, for example, as a therapeutic agent, a food preservative, a disinfectant or a medicament.

A cyclic theta defensin can be particularly useful as a therapeutic agent for treating a patient suffering from a bacterial, viral, fungal or other infection due to a microorganism susceptible to the antimicrobial activity of the theta defensin, since a cyclic theta defensin is particularly resistant to the activity of endogenous proteases and peptidases. The resistance of a theta defensin or analog thereof is due, in part, to the cyclization of the peptide, such that it lacks a free amino terminus and a free carboxyl terminus. Thus, the invention provides methods of treating an individual suffering from a pathology caused, at least in part, by microbial infection, by administering a theta defensin to the individual under conditions that allow the theta defensin to contact the infecting microorganisms, thereby reducing or inhibiting the survival or growth of the microorganism and alleviating the severity of the infection.

For use as a therapeutic agent, the theta defensin can be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can contain physiologically acceptable compounds that act, for example, to stabilize or increase the absorption of the theta defensin. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; or other stabilizers or excipients. One skilled in the art would know that the choice of a pharmaceutically acceptable carrier, including a physiologically acceptable compound, depends, for example, on the route of administration of the composition.

A pharmaceutical composition containing a theta defensin can be administered to an individual by various routes, including by intravenous, subcutaneous, intramuscular, intrathecal or intraperitoneal injection; orally, as an aerosol spray; or by intubation. If desired, the theta defensin can be incorporated into a liposome, a non-liposome lipid complex, or other polymer matrix, which further can have incorporated therein, for example, a second drug useful for treating the individual. Use, for example, of an antimicrobial indolicidin peptide incorporated into liposomes has been demonstrated to have antifungal activity in vivo (Ahmad et al., *Biochem. Biophys. Acta* 1237:109–114 (1995), which is incorporated herein by reference). Liposomes, which consist of phospholipids or other lipids, are nontoxic, physiologically acceptable and metabolizable carriers that are relatively simple to make and administer (Gregoriadis, *Liposome Technology*, Vol. 1 (CRC Press, Boca Raton Fla., 1984), which is incorporated herein by reference). The skilled artisan will select a particular route and method of administration based, for example, on the location of a microorganism in a subject, the particular characteristics of the microorganism, and the specific theta defensin or theta defensin analog that is administered.

Food and food products also can be treated with a theta defensin for the purpose of preserving the food or eliminating or preventing infection by microorganisms. For example, shellfish and poultry products routinely harbor enteric pathogenic microorganisms. The growth or survival of such microorganisms can be reduced or inhibited by contacting the product with the theta defensin. Food crops such as fruits, vegetables and grains can be treated with a theta defensin in order to reduce or inhibit post-harvest spoilage caused by microorganisms, for example, by administering the analog topically using an aerosolized form of the analog. In addition, transgenic plants or animals useful in the food industry can be produced by introducing a nucleic acid molecule encoding a precursor of a theta defensin into the germline cells of such organisms. Methods for producing transgenic plants and animals are well known and routine in the art. Stable transgenic expression as well as transient transgene expression can be used (see, for example, the GENEWARE system; Biosource Technologies; Vacaville Calif.).

A theta defensin also can be used as a disinfectant to reduce or inhibit the survival or growth of microorganisms on an object or in a solution. A theta defensin can be used to treat essentially any object or solution that can sustain microbial growth, where the survival or growth of the microorganisms is undesirable. In particular, an object or solution that comes into contact with a mammal such as a human, for example, baby wipes, diapers, band-aids, towelettes, make-up products and eyewash and contact lens solutions can be treated with a theta defensin or analog thereof. In such methods, the theta defensin can be applied topically to the object or can be added to the solution or can be in an aerosolized form in a gas.

In order to exhibit antimicrobial activity in an environment, an effective amount of a theta defensin is administered to the environment. As used herein, the term "effective amount" refers to the amount of a theta defensin that reduces or inhibits the survival or growth of a microorganism in an environment. In particular, an effective amount of a theta defensin produces only minimal effects against the environment, although the level of an acceptable deleterious effect is weighed against the benefit caused by the antimicrobial effect.

A theta defensin or analog thereof can be administered to a subject such as a human systemically at a dose ranging from 1 to 100 mg/kg body weight, for example, at a dose of about 10 to 80 mg/kg, particularly about 10 to 50 mg/kg. A theta defensin also can be incorporated into liposomes, if desired, in which case the total amount administered to a subject generally can be reduced. Furthermore, a theta defensin can be administered orally to a subject at a dose ranging from about 1 to 100 mg/kg body weight, for example at a dose of about 10 to 200 mg/kg, in particular about 20 to 100 mg/kg. In addition, a theta defensin can be administered topically to an environment, which can be a human subject, or can be placed in a solution, at a concentration of about 0.1 to 10 mg/ml, for example, at a concentration of about 0.5 to 5 mg/ml. Although theta defensins generally are effective in microgram per ml amounts, an effective amount for administration to a particular environment will depend, in part, on the environment. For example, when administered to a mammal such as a human, a theta defensin, in addition to having antimicrobial activity, can have an undesirable side effect. The skilled artisan will recognize that the level of such side effects must be considered in prescribing a treatment and must be monitored during the treatment period, and will adjust the amount of the theta defensin that is administered accordingly.

An effective amount of a theta defensin also will vary depending, for example, on the characteristics of the target microorganism, the extent of prior infection or growth and the specific theta defensin or analog thereof that is administered. In addition, an effective amount depends on the form in which the theta defensin is administered. For example, incorporation of another antimicrobial peptide, indolicidin, into liposomes allowed administration of a higher amount of the peptide than "free" indolicidin, without producing unacceptable side effects, such that fungal infection in mice could be cured (Ahmad et al., supra, 1995).

The invention additionally provides a method of reducing or inhibiting growth or survival of a microorganism in an individual by administering a molecule, wherein the molecule increases expression of a theta defensin. Theta defensins are polypeptides expressed in leukocytes of mammals, in particular primates, including humans. Thus, theta defensins function as part of the endogenous defense system for a mammal to combat microbial infections. Since theta defensins are expressed in mammals, methods to increase expression of theta defensin in the organism can be used to reduce or inhibit microbial growth in the organism. Using the genomic clones described herein, one skilled in the art can readily determine regulatory molecules that can alter transcription of a theta defensin gene and screen for those molecules that effect an increase in theta defensin expression. Cytokines, for example, monocyte chemoattractant protein 1 (MCP-1), interleukin 8 (IL8) or other cytokines, that activate granulocytes can be tested for stimulatory activity of theta defensin expression. Cytokines, or other compounds, can be screened for stimulatory activity. Compounds having stimulatory activity can be used to increase expression of a theta defensin in an organism to reduce or inhibit growth or survival of a microorganism in an individual.

The following examples are intended to illustrate but not limit the present invention.

EXAMPLE I

Preparation and Characterization of Theta Defensin

This example provides methods for purifying and characterizing a cyclic theta defensin.

Native theta defensin was purified from Rhesus macaque peripheral leukocytes. Briefly, leukocytes were obtained from anticoagulated whole blood of adult rhesus macaques after erythrocytes were depleted by dextran sedimentation. The cell pellet ($6 \times 10^6$ cells; 91% neutrophils, 5% mononuclear cells, 4% eosinophils) was snap frozen, suspended in 0.5 ml ice cold 30% acetic acid and stirred on melting ice for 18 h. The suspension was clarified by centrifugation at 4° C., the supernatant was lyophilized, and then dissolved in 0.5 ml methanol-water (80:20). After 6–8 h of stirring at 8° C., the sample was clarified by centrifugation and the supernatant was lyophilized. The dry powder was dissolved in 0.5 ml 5% acetic acid prior to RP-HPLC.

Rhesus theta defensin-1 (RTD-1) was isolated during studies to characterize defensins of rhesus macaque neutrophils. Peripheral blood neutrophils (>90% PMN) were subjected to sequential acetic acid and water/methanol extraction steps as described above, and the extract was fractionated by reversed phase HPLC (FIG. 1A). An α-defensin-enriched extract of 6×10⁶ leukocytes (91% PMNs) was fractionated by RP-HPLC on a 0.46×25 cm C-18 column equilibrated in 0.1% aqueous trifluoroacetic acid (TFA) and developed with a linear acetonitrile gradient. RTD-1 eluted in the arrow-marked peak.

Figure 1B:
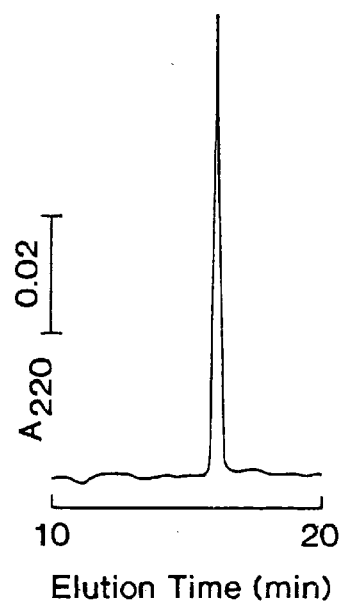
Figure 1C:
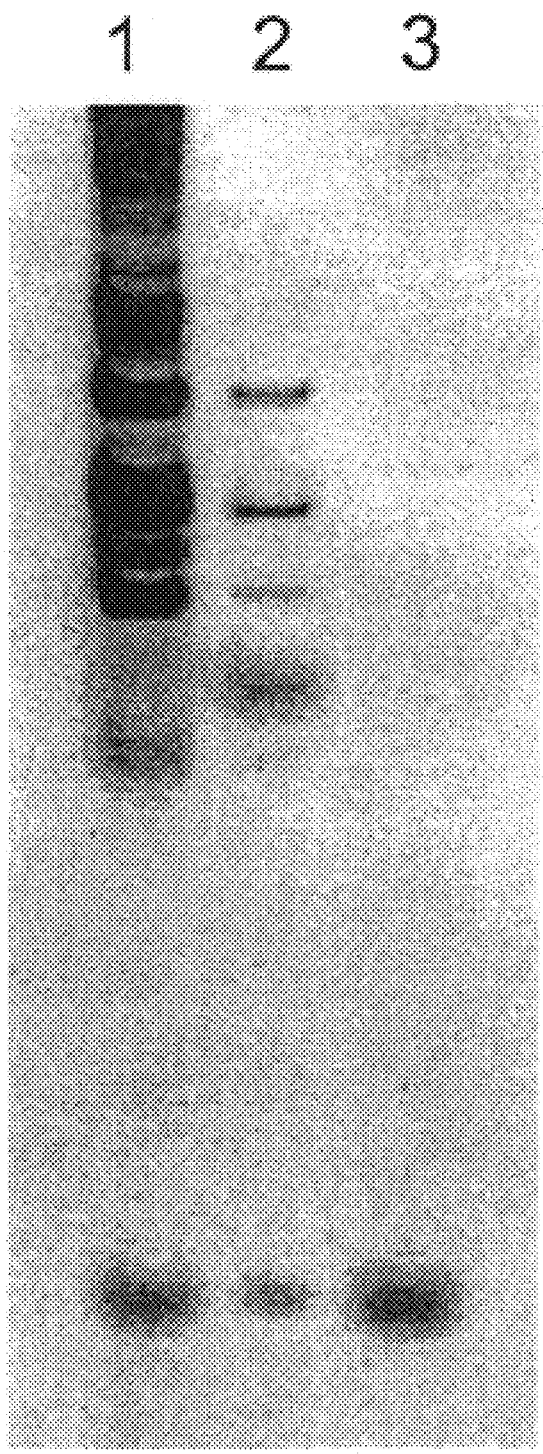

Chromatographic peaks eluting between 20 and 50 minutes were purified to homogeneity. Analytical RP-HPLC of purified RTD-1 is shown in FIG. 1B. The purity of RTD-1 was assessed by RP-HPLC of RTD-1 obtained from the peak (arrow) in FIG. 1A on an analytical C-18 column developed with acetonitrile at 0.5% per min. Acid-urea polyacrylamide gel electrophoresis (PAGE) was also used to analyze purified peptides (see FIG. 1C). Samples of 30% acetic acid extract (2×10⁶ cell equivalents; lane 1), methanol/water extracted phase (1×10⁷ cell equivalents; lane 2) and 1 µg of RTD-1 were resolved on a 12.5% acid-urea polyacrylamide gel and stained with formalin-Coomassie blue.

The purified chromatographic peaks were screened for antibacterial activity against *Escherichia coli* ML35 and *Staphylococcus aureus* 502a. Briefly, antibacterial activity was screened with an agar diffusion assay using lyophilized samples of HPLC fractions dissolved in 5 µl of 0.01% acetic acid as described by Lehrer et al., *J. Immunol. Methods* 137:167–173 (1991)). RTD-1 was found to have the greatest activity of any of the peptides isolated. Microbicidal peptides were characterized by amino acid analysis (ACCUTAG; Waters; Milford Mass.) and automated Edman degradation. Sequence analysis was performed by automated Edman degradation with on-line PTH amino acid analysis. Seven of the eight active peptides were found to be α-defensins that were similar to previously characterized human peptides. RTD-1 (arrow in FIG. 1A), was relatively abundant (FIGS. 1A and 1C) and possessed the greatest antibacterial activity of any of the peptides isolated. The yield of RTD-1 was approximately 100 µg per 10⁹ neutrophils.

Amino acid analysis revealed that RTD-1 contained 18 amino acids: 1 Thr, 1 Val, 1 Leu, 1 Phe, 1 Ile, 2 Gly, 5 Arg, and 6 Cys. RTD-1 was also analyzed by mass spectroscopy, performed by matrix-assisted laser desorption ionization/time of flight (MALDI-TOF) on a PerSeptive Biosystems Voyager RP mass spectrometer (PerSeptive; Framingham MA). Samples (1–10 pmol) were dissolved in water-acetonitrile (1:1) containing 0.1% TFA. MALDI-TOF mass spectroscopy analysis of the native peptide (2082.0) and S-pyridylethylated peptide (2720.3)(Henschen, *Advanced Methods in Protein Microsequence Analysis*, Wittmann-Liebold et al., eds., Springer-Verlag, Berlin, p. 244 (1996)) demonstrated that the six cysteines exist as three intramolecular disulfides.

Figures 2A, 2B:
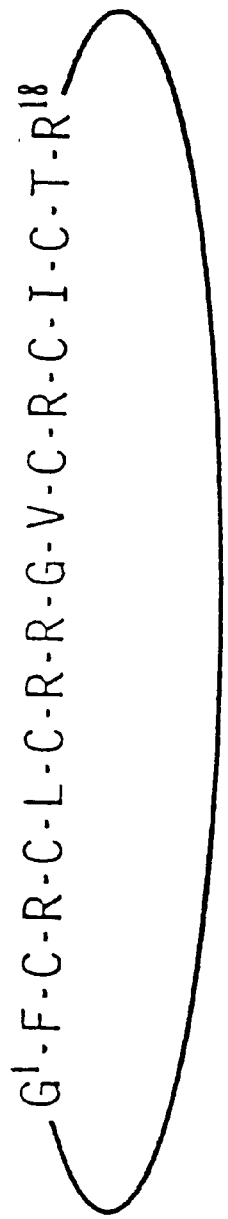
FIGS. 2A and 2B show the peptide backbone structure of RTD-1.

Attempts to sequence RTD-1 failed, indicating blockage of the amino terminus. Therefore, the primary structure of RTD-1 was determined by sequencing overlapping chymotryptic and tryptic fragments. Briefly, RTD-1 disulfides were reduced with dithiothreitol (DTT) and alkylated with 4-vinyl pyridine so that cysteine was analyzed as the S-pyridylethyl derivative. S-pyridylethylated peptide (2 nmol) was digested at 37° C. for 10 min with 0.4 µg TPCK trypsin or TLCK α-chymotrypsin in 50 µl 1% ammonium bicarbonate, pH 8.0. Peptide fragments were purified by C-18 RP-HPLC and characterized by amino acid analysis, MALDI-TOF MS, and automated sequencing. FIG. 2A shows the amino acid sequence of the peptide chain as determined by Edman sequencing and MALDI-TOF MS of purified fragments produced by partial acid hydrolysis (methanol/HCl) and digestion with trypsin (T) and chymotrypsin (CT). The sequence analysis revealed that the peptide is entirely cyclized through peptide bonds (see FIG. 2B). The cyclization of the backbone accounts for the 18 atomic mass number (a.m.u.) difference between the measured mass (2082.0 obtained; 2081.7 calculated) of RTD-1 and the theoretical mass of a linear peptide (2099.7) of the same composition.

The disulfide structure of RTD-1 was determined by characterizing protease digestion fragments produced by sequential incubation of native peptide with trypsin and thermolysin. Briefly, 2.5 nmol of RTD-1 was digested at 37° C. for 16 h with 0.5 µg TPCK trypsin in 50 µl of 0.1 M pyridine acetate, pH 6.4. The digest, when fractionated by RP-HPLC, gave one predominant peak. Analysis by MALDI-TOF MS demonstrated that trypsin cleavage occurred at all five arginines, releasing a 17-residue, four stranded oligopeptide connected by three disulfides (see FIG. 3). 50 pmol of the tryptic 17-residue oligopeptide was digested with 10 ng of thermolysin in 5 µl of 0.1% TFA, adjusted to pH 7 with 0.1 M ammonium bicarbonate supplemented with 10 mM CaCl₂, for 2 h at 37° C. To the reaction mixture was added 5 µl 0.1% TFA-acetonitrile (1:1). One µl aliquots were analyzed by MALDI-TOF MS as described above. Alternatively, about 3 nmol of the 17-mer were digested with thermolysin under similar conditions, and the thermolytic fragments were isolated by HPLC. MALDI-TOF MS analysis of individual peaks confirmed the fragment pattern obtained by analysis of the unfractionated digestion mixture.

Figure 3:
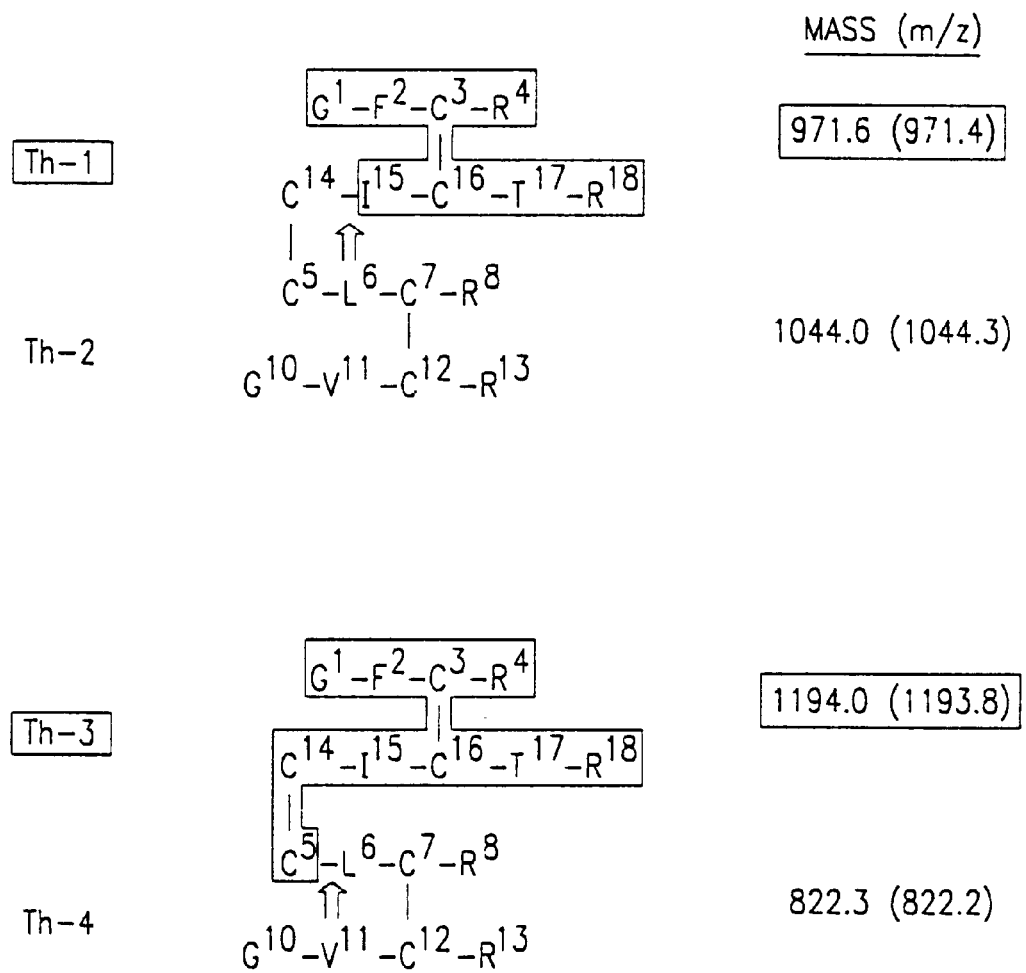
FIG. 3 shows disulfide analysis of RTD-1. A tridisulfide-containing 17-residue oligopeptide generated by trypsin digestion was purified by RP-HPLC and further digested with thermolysin. MS analysis (calculated values in parentheses) of the digest or of HPLC-purified fragments disclosed thermolytic cleavage at Cys-14/Ile-15 and at Cys-5/Leu-6 (arrows), producing four major thermolytic fragments (Th-1 to Th-4). The masses of all fragments were consistent with the disulfide assignments shown.

Cleavage by trypsin generated a major product that was purified by HPLC, the mass of which was determined to be 1998.1. Comparison of the mass and amino acid analysis of this peptide revealed that it was produced by cleavage at the carboxyl side of all 5 arginines, thus generating a 17-residue oligopeptide composed of 4 substituent chains linked by three disulfides (calculated mass=1997.5)(FIG. 3). To distinguish between the 8 possible disulfide pairings in the 17-mer, the oligopeptide was digested with thermolysin and the resulting fragments were analyzed by MALDI-TOF MS as described above. MS analysis (FIG. 3; calculated values in parentheses) of the digest or of HPLC-purified fragments disclosed thermolytic cleavage at Cys-14/Ile-15 and at Cys-5/Leu-6 (arrows), producing four major thermolytic fragments, indicated as Th-1 to Th-4 in FIG. 3. The masses of all fragments were consistent with the disulfide assignments shown in FIG. 3.

The m/z values of the thermolysin fragments were consistent with only one cystine motif, which is shown in FIG. 3, revealing that the cyclic chain is stabilized by 3 disulfides in a picket fence-like array that stabilizes two hypothetical β-strands connected by turns at both ends (see FIG. 4). Schematically, RTD-1 resembles the Greek letter theta (FIG. 4), hence the selection of "theta" defensin to describe this molecular motif.

RTD-1 is the first example of a macrocyclic peptide or protein in animals. It is highly cationic, possessing a net charge of +5 at pH 7 (calculated pI>12), and its dense cystine motif in RTD-1 is distinct from that determined for α or β defensins (Tang and Selsted, *J. Biol. Chem.* 268:6649–6653 (1993)). The cyclic structure of RTD-1 reveals that primate cells possess a post-translational processing pathway capable of producing a head-to-tail ligated peptide chain. Analogous macrocyclic peptides have been isolated from plants of the Rubiaceae family and, like RTD-1, these molecules possess three intramolecular disulfides (Derua et al., *Biochem. Biophys. Res. Commun.* 228:632–638 (1996)). Two of these peptides are reported to have antiviral activity against HIV-1 (Gustafson et al., *J. Amer. Chem. Soc.* 116:9337 (1994)). The plant peptides differ from RTD-1 in their size (29–31 amino acids) and their cystine motif, which is characterized by "overlapping" disulfides (see FIG. 4). Thus far, the genes encoding these plant peptides have not been characterized, nor have mechanisms been proposed for the formation of the cyclic backbone. The only other known macrocyclic peptides are cysteine-free peptides. One, AS-48, is a plasmid-encoded peptide expressed by *Enterococcus faecalis* (Galvez et al., *Antimicrob. Agents Chemother.* 33:437 (1989)). The second is J25, a microcin from *E. coli* (Blond et al, *Eur. J. Biochem.* 259:747–755 (1999)).

Searches for amino acid sequence similarity to RTD-1 were carried out using all 18 possible linearized peptides as query sequences (Altschul et al., *Nucleic Acids Res.* 25:3389–3402 (1997)). Taking into consideration the linear cysteine spacing and disulfide connectivities of RTD-1, the most similar protein sequence identified was that of the porcine antimicrobial peptide protegrin 3 (PG-3)(see FIG. 4). Protegrins are 17–18 amino acid, di-disulfide containing peptides that are members of the cathelicidin family of antimicrobial peptides (Zanetti et al., *FEBS Lett.* 374:1–5 (1995)). Cathelicidins share a high degree of sequence similarity in the prepro-regions of their precursors, but the carboxyl termini, containing the antimicrobial peptide segments, vary markedly. Like protegrins, RTD-1 is predicted to be predominantly composed of two disulfide stabilized β strands connected by turns.

A model of RTD-1 was constructed by energy minimization of the covalent structure. Briefly, the RTD-1 backbone and disulfides were constructed using the Insight II program. Energy minimization was used to allow the structure to relax in vacuo, and the molecule was then placed into a 25.0 Å radius sphere of water. With the peptide fixed, water molecules were first energy minimized, and the energy of the entire complex was then minimized. Molecular dynamics simulations were then carried out at 300 K. After 5 psec, the total energy did not show fluctuations greater than 183 atom units, and the structure appeared stable. Further energy minimization resulted in the peptide structure shown in FIG. 4. The consistent valence force field (cvff) was used in all molecular mechanics and molecular dynamics calculations. FIG. 5 shows the coordinates used to generate the molecular model shown in FIG. 4.

As shown in FIG. 4, RTD-1 is remarkably similar to the solution structure of protegrin 1. This similarity suggested the possibility that RTD-1 is a member of the cathelicidin family. However, subsequent studies demonstrated that RTD-1 is not a cathelicidin, but rather the product of two α-defensin-related genes (see Example V).

These results demonstrate that theta defensin isolated from macaque neutrophils, RTD-1, is a macrocyclic peptide linked head-to-tail and containing three intramolecular disulfide bonds.

EXAMPLE II

Solid Phase Synthesis of Theta Defensin

This example describes chemical synthesis of theta defensin.

Figure 6A:
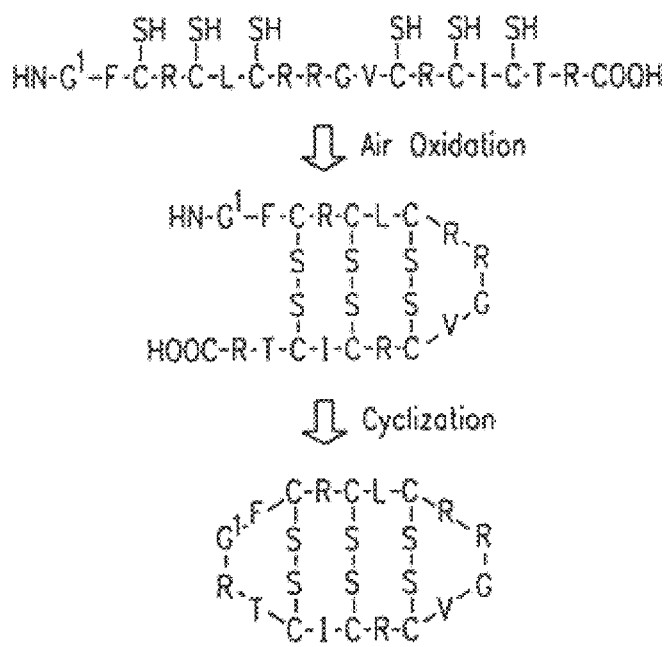
FIGS. 6A, 6B and 6C show synthesis and characterization of RTD-1.

A synthetic version of RTD-1 was produced by solid phase synthesis. Inspection of the theta defensin disulfide motif suggested that assembly of a linear 18-mer in which $Gly^1$ was placed at the amino terminus (see FIG. 4) would both facilitate disulfide-bond formation and proximate positioning of the amino and carboxyl termini for cyclization. A linear version of RTD-1 was assembled using Fmoc chemistry, cleaved, deprotected, and the reduced peptide was purified by RP-HPLC at pH 2.1. A schematic of the synthesis is shown in FIG. 6A.

The linear peptide chain of the monkey peptide was assembled on PEG-PS resin at 0.2 mmol scale on a Millipore 9050 Plus continuous-flow peptide synthesizer (Millipore; Bedford Mass.). Fmoc-chemistry was utilized and the following protecting groups were employed: Arg(Pbf) (2,2,4, 6,7-pentamethyldihydrobenzofuran-5-sulfonyl); Cys(Trt) (trityl or triphenylmethyl); and Thr(tBu) (tert-butyl). All amino acids except cysteine were coupled by O-(7-azabenzotriazol-1-yl)-1,1,3,3-tetramethyluronium hexafluorophosphate/N,N-diisopropylethylamine (HATU/DIEA) activation. Cysteine was coupled as the preformed pentafluorophenyl ester. Ile, Leu and Thr were double-coupled. The protecting groups were removed and the peptide was cleaved from the resin by 5 hour treatment with 100 ml of Reagent-K, containing TFA-phenol-water-thioanisole-1,2-ethanedithiol (82.5:5:5:5:2.5), at room temperature with agitation. The crude peptide was separated from the resin by glass fiber filtration. The resin was rinsed consecutively with 5 ml of Reagent-K, 50 ml of 30% acetic acid/water and 50 ml of methylene chloride, and the washes were added to the initial filtrate. After vigorous mixing and phase-separation, the peptide-containing aqueous phase was extracted twice with methylene chloride (2×50 ml) and lyophilized, giving 225 mg (54% yield) of crude product obtained as a white powder.

A 25 mg sample of lyophilized crude material was dissolved in 6 M guanidine HCl, 0.2 M Tris-HCl, 0.2 mM EDTA, and reduced with an excess of dithiothreitol at 50° C. for 4 hrs under nitrogen. The reaction mixture was acidified by addition of acetic acid to a 5% v/v final concentration, and the reduced product was isolated by RP-HPLC purification on a C-18 column using 0.1% TFA/acetonitrile-water solvent system. The reduced peptide was diluted to 0.1 mg/ml in 0.1% acetic acid, and the pH was adjusted to 7.5 with ammonium hydroxide. Oxidation was carried out by stirring in an open vessel at room temperature for 18 hr, after which time the solution was found to be negative for free sulfhydryls based on a negative reaction with Ellman's reagent, and HPLC analysis showed quantitative conversion of the reduced peptide to the oxidized form.

The oxidized peptide was purified by RP-HPLC on a semi-preparative C-18 column using a 0.1% HCl/acetonitrile-water solvent system yielding 9.0 mg of peptide. MALDI-TOF MS measurements were consistent with the acyclic form of RTD-1 shown in FIG. 6A. The peptide was air oxidized, repurified by HPLC, and converted to the hydrochloride salt by RP-HPLC in solvents containing 0.1% HCl as described above.

The oxidized peptide was then cyclized by activating the carboxyl group (FIG. 6A). The oxidized acyclic synthetic peptide was cyclized to form an amide bond between the amino group of Gly-1 and the carboxyl group of Arg-18. After 3.0 mg of acyclic oxidized RTD-1 was repeatedly lyophilized to remove volatile components, cyclization was carried out in 3.0 ml of dimethylsulfoxide containing 60 and 20 equivalents of ethylenediaminecarbodiimide and 1-hydroxybenzotriazole (HOBt), respectively, for 18 hours at room temperature. The resulting solution was lyophilized and purified by RP-HPLC.

The cyclization reaction mixture gave a major peak that coeluted with natural RTD-1. MALDI-TOF mass spectroscopy demonstrated that the product (1.7 mg, 56.6% yield) had the expected mass of the cyclic peptide. In addition, the material in this peak coeluted with natural RTD-1 on analytical RP-HPLC, co-electrophoresed with natural RTD-1 on acid-urea PAGE, and had identical CD spectra in water, methanol, and 10 mM sodium phosphate, pH 7.4.

Figure 6B:
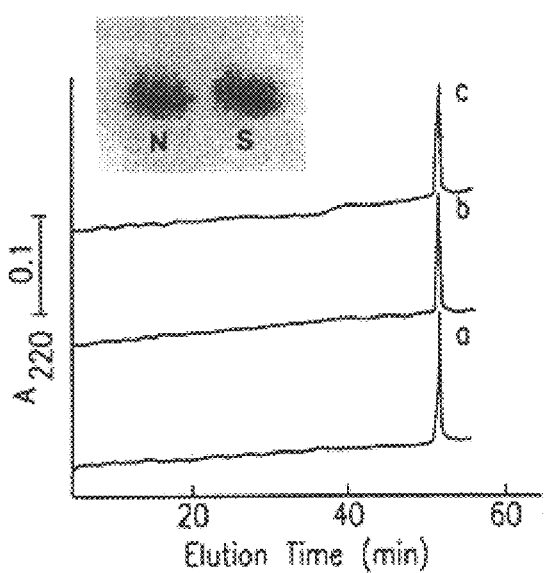
Figure 6C:
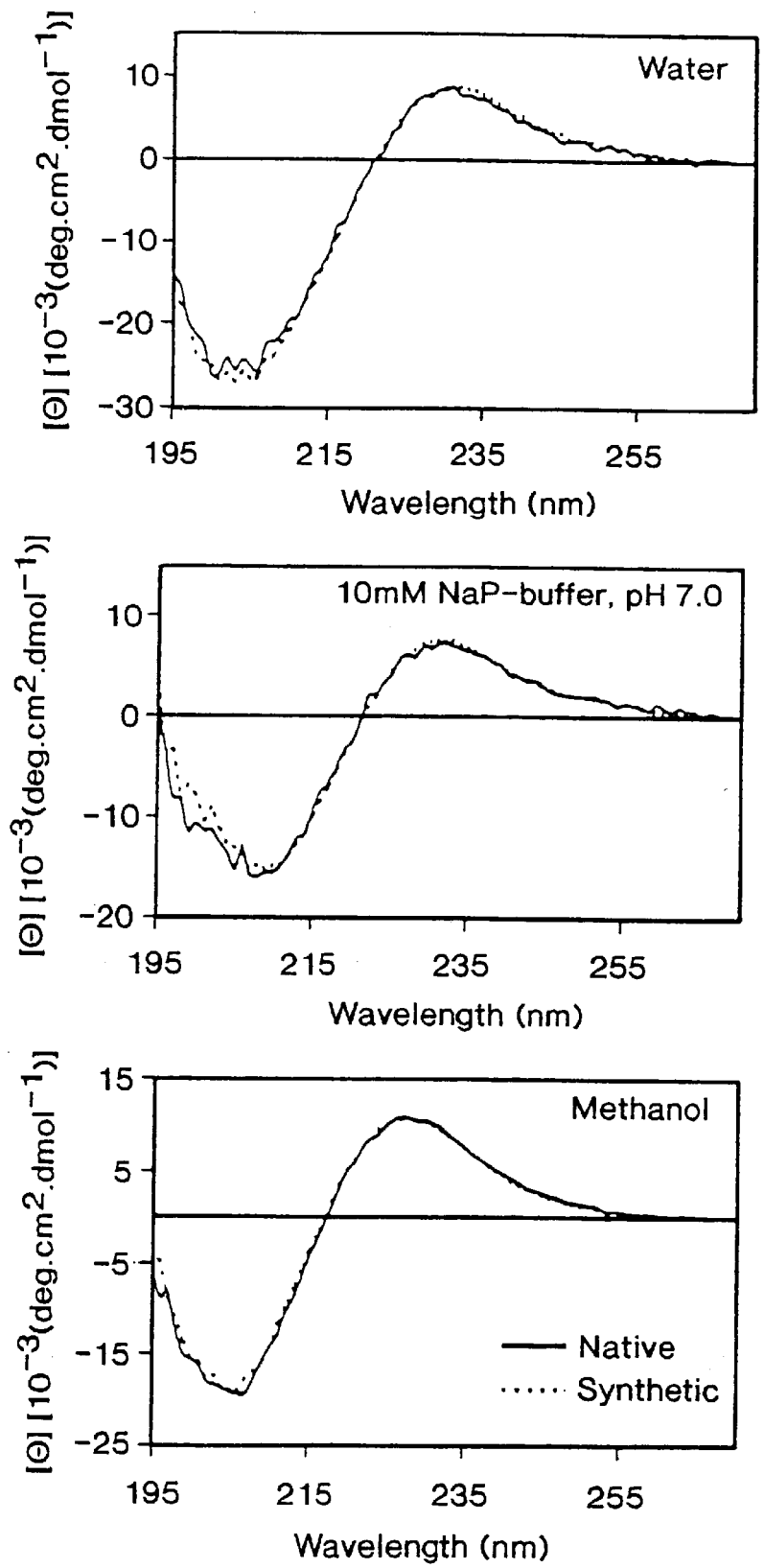

The cyclized peptide, generated by formation of a peptide bond between Gly$^1$ and Arg$^{18}$, was formed with a yield of 56%. Analysis of the disulfide pattern of cyclized synthetic RTD-1 was carried out as described for the natural peptide, and confirmed that the cysteines were correctly paired. The equivalence of natural and synthetic TD-1 was confirmed by MALDI-TOF MS, analytical RP-HPLC (FIG. 6B) and acid-urea PAGE (FIG. 6B, inset). Circular dichroism spectroscopy was also performed on synthetic and natural RTD-1 (FIG. 6C). Circular dichroic spectra of synthetic and natural RTD-1 were determined in water, 10 mM sodium phosphate buffer, and methanol at a peptide concentration of 111 µg/ml (53.3 µM). CD spectroscopy confirmed the equivalence of the synthetic and natural RTD-1.

These results indicate that theta defensin can be chemically synthesized in a form equivalent to natural RTD-1.

EXAMPLE III

Antimicrobial Activity of Theta Defensin

This example demonstrates that theta defensin exhibits broad spectrum antimicrobial activity.

Figure 7:
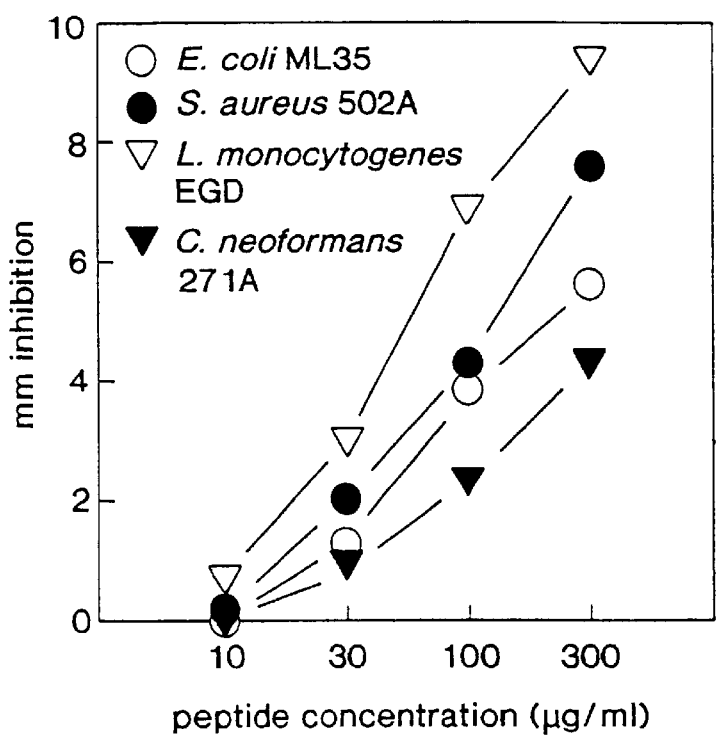
FIG. 7 shows the zone of inhibition (mm inhibition) of growth of *Staphylococcus aureus* 502A (closed circles), *Escherichia coli* ML35 (open circles), *Listeria monocytogenes* EGD (open triangles), and *Cryptococcus neoformans* 271A (closed triangles) at various concentrations of theta defensin.

Agar diffusion assays and microbicidal suspension assays were used to examine the activity of theta defensin against *Staphylococcus aureus* 502A, *Escherichia coli* ML35, *Listeria monocytogenes*, and *Cryptococcus neoformans*. For agar diffusion assays, theta defensin activity was determined at concentrations 10, 30, 100 or 300 µg/ml in agar plates seeded with 1×10$^6$ colony forming units of each microorganism. theta defensin demonstrated a dose dependent increase in the zone of inhibition for each of the microorganisms examined (see FIG. 7).

Figure 8:
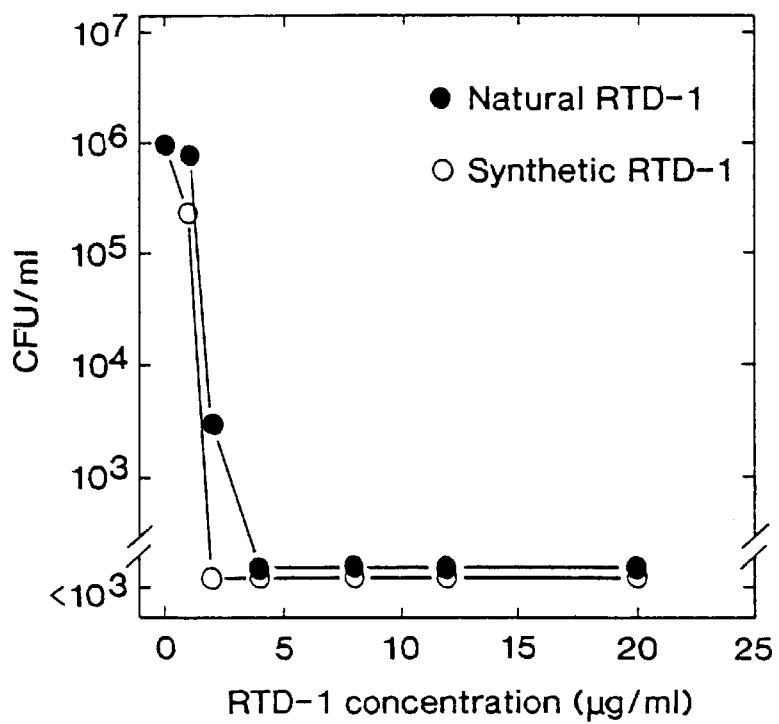
FIG. 8 shows a comparison of staphylocidal activity of natural and synthetic RTD-1. *S. aureus* 502a was incubated with increasing concentrations of natural or synthetic theta defensin peptide. Killing was quantified by colony counts.

The in vitro antimicrobial properties of RTD-1 were further evaluated in microbicidal assays against a panel of bacterial and fungal test organisms. Increasing concentrations of natural and synthetic RTD-1 were incubated with *Staphylococcus aureus* 502a for 2 h at 37° C. in 10 mM PIPES, pH 7.4 (FIG. 8). Killing was quantified by colony counts. As shown in FIG. 8, nearly complete killing (99 to 99.99%) of this organism was achieved at peptide concentrations of 2–4 µg/ml of natural and synthetic RTD-1, and both preparations reduced colony counts to below the level of detection at peptide concentrations ≧4 µg/ml.

Figure 9A:
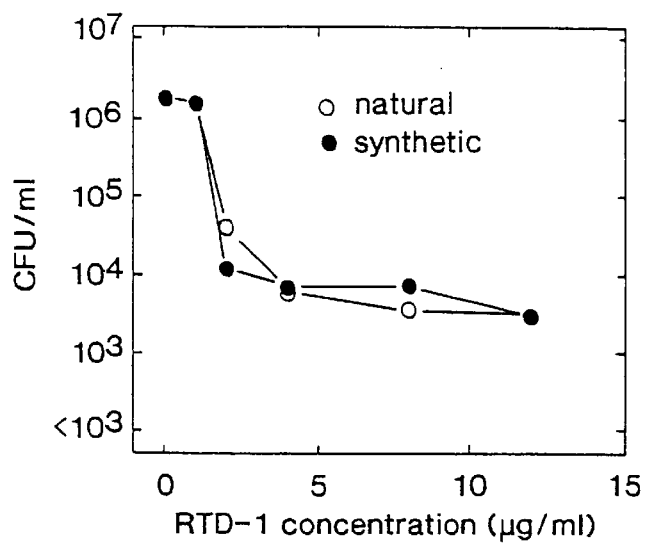
FIGS. 9A, 9B, 9C, 9D and 9E show microbicidal activity of RTD-1.
Figure 9B:
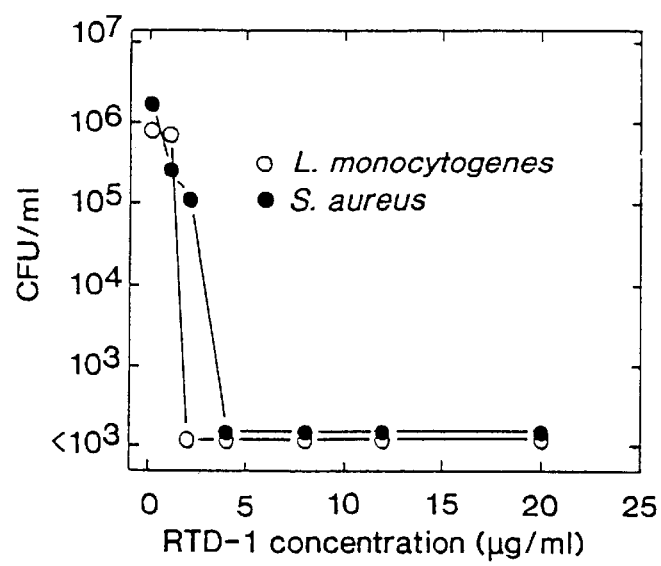
Figure 9C:
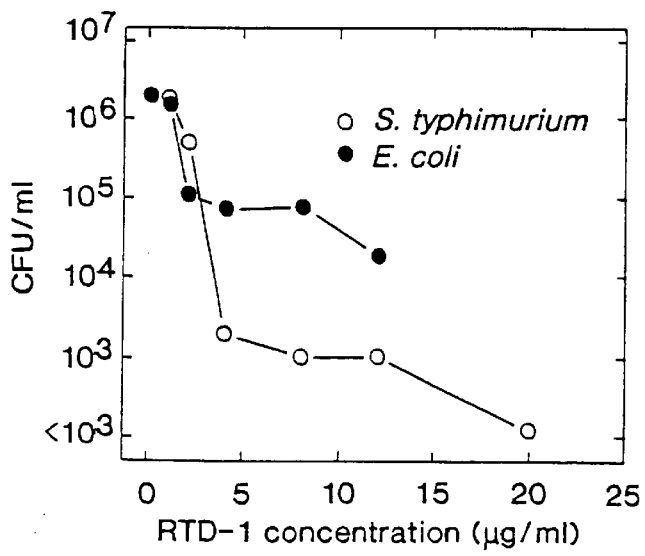
Figure 9D:
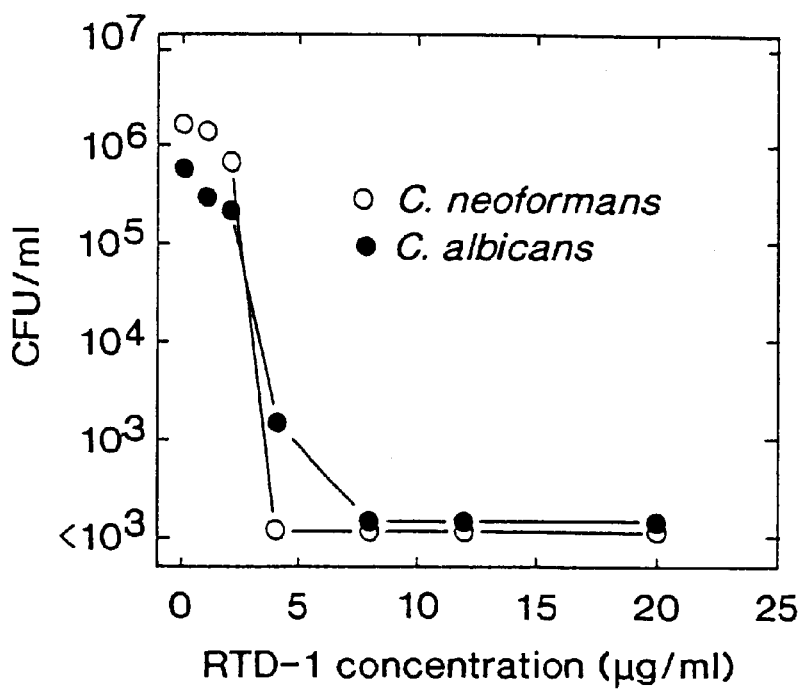

Additional antimicrobial assays were conducted on other microbial organisms. FIG. 9 shows microbicidal activity of RTD-1. In FIG. 9A, *S. aureus* 502a was incubated with increasing concentrations of natural or synthetic peptide for 30 min at 37° C. in 10 mM PIPES, pH 7.4, containing 5 mM glucose. Killing was quantified by colony counts. In FIGS. 9B to 9D, each test organism was incubated for 2 hr with RTD-1, as in FIG. 9A, at the peptide concentrations indicated. The limit of detection (1 colony per plate) was equal to 1×10$^3$ colony forming units in the incubation mixture. The results shown in FIG. 9 demonstrate that the synthetic RTD-1 killed gram positive bacteria (*S. aureus, L. monocytogenes*), gram negative bacteria (*E. coli* ML 35, *S. typhimurium*), and fungi (*C. albicans* and *C. neoformans*) at similar peptide concentrations.

Figure 9E:
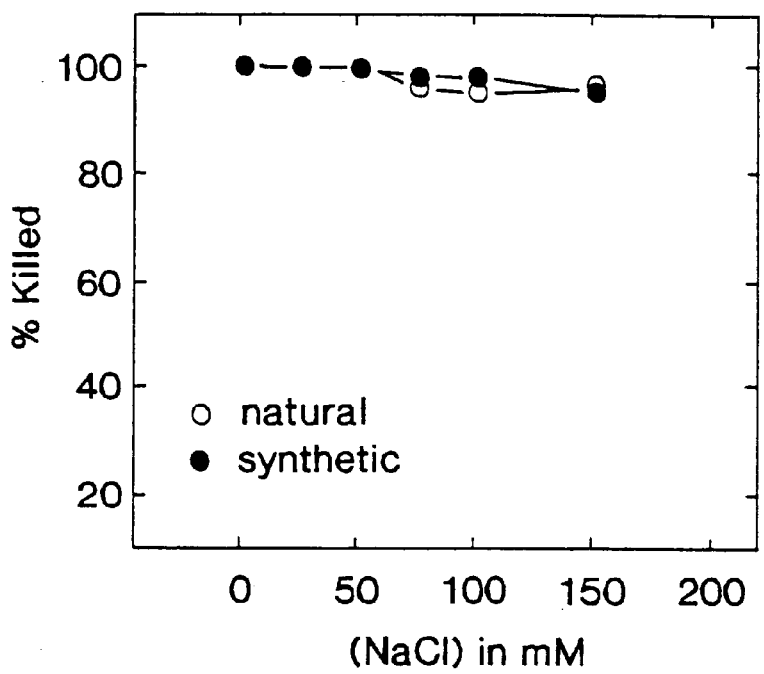

Several previous studies have demonstrated that in vitro defensin-mediated microbicidal activity is antagonized by increased ionic strength (Bals et al., *Infect. Immun.* 66:1225 (1998); Valore et al., *J. Clin. Invest.* 101:1633 (1998); Goldman et al., *Cell* 88:553 (1997); Smith et al., *Cell* 85:229 (1996)). It has been proposed that salt sensitivity of airway defensins underlies the susceptibility of cystic fibrosis patients to pulmonary infections. The effect of ionic strength on RTD-1 bactericidal activity was tested in a killing assay against *S. aureus* 502a. Killing of *S. aureus* 502a was assessed after a 2 h incubation as in FIG. 9A, with 10 µg/ml of natural or synthetic RTD-1 supplemented with increasing concentrations of NaCl (FIG. 9E). NaCl concentrations as high as 150 mM had little effect on the staphylocidal activity of natural or synthetic RTD-1 (FIG. 9E). These results indicate that RTD-1 is clearly distinguished from the salt-mediated inhibition of α or β defensins.

Figure 10:
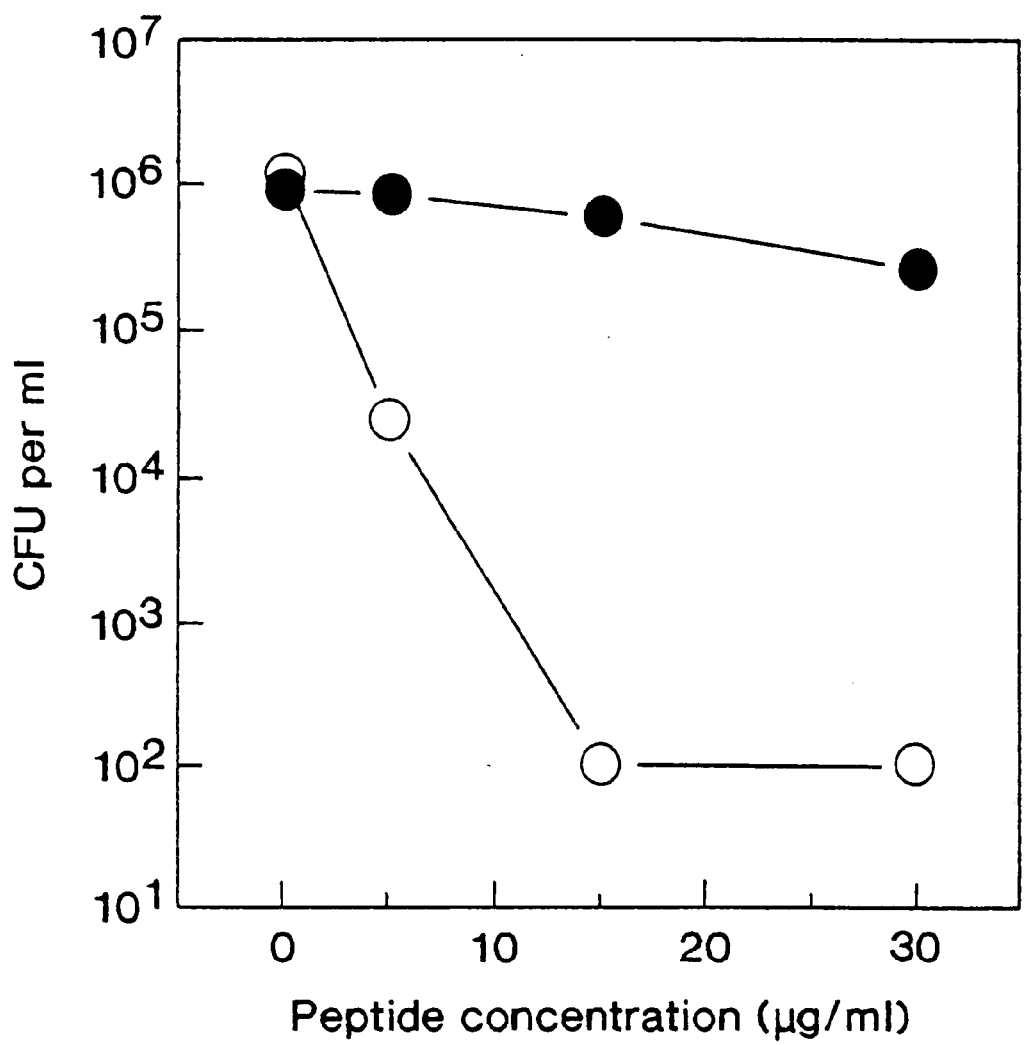
FIG. 10 shows microbicidal activity of acyclic RTD-1. *S. aureus* 502a was incubated with increasing concentrations of acyclic RTD-1 with (solid circles) or without (open circles) 130 mM NaCl. Killing activity was quantified by colony counts after 18 hrs.

An acyclic version of theta defensin was also tested for antimicrobial activity. As shown in FIG. 10, *S. aureus* was incubated with increasing concentrations of acyclic RTD-1 with (solid circles) or without (open circles) 130 mM NaCl. Killing activity was quantified by colony counts after 18 hrs. In contrast to the cyclic form of theta defensin, the acyclic form exhibits lower activity in the presence of NaCl (FIG. 10). The cyclic form is about three times more active than the acyclic form of theta defensin in both gram positive bacteria (Staphylococcus) and gram negative bacteria (*E. coli*). These results demonstrate that an acyclic form of theta defensin has antimicrobial activity.

These results demonstrate that theta defensin, both synthetic and natural, has wide antimicrobial activity against gram positive bacteria, gram negative bacteria and fungi.

EXAMPLE IV

Immunolocalization of RTD-1 in Rhesus Leukocytes

This example describes the generation of anti-RTD-1 antibody and determination of the localization of RTD-1 in rhesus leukocytes.

Anti-RTD-1 antibody was produced by immunizing New Zealand white rabbits with an immunogen composed of the oxidized, open chain version of the peptide (see FIG. 6A) conjugated to ovalbumin. Briefly, immunogen was prepared by conjugating 1.2 mg acyclic RTD-1 (FIG. 6A) with 1.2 mg ovalbumin in 2.4 ml of 0.1 M sodium phosphate, pH 7.4, containing 0.1% glutaraldehyde. The mixture was stirred for 18 h at room temperature, quenched with 0.3 M glycine and the mixture was dialyzed in 500 molecular weight cut off tubing against water and lyophilized. Two New Zealand white rabbits were immunized with the conjugate. The antisera from both rabbits had a titer of greater than 1:2500 as determined by competitive ELISA using RTD-1 conjugated to goat gamma globulin as the target antigen.

Dot blot analysis demonstrated that anti-RTD-1 antiserum reacted with natural and synthetic RTD-1, and the oxidized acyclic version of RTD-1. The anti-RTD-1 antibody did not recognize any of the previously characterized α-defensins (HNP 1–4) expressed by human leukocytes nor any of the rhesus leukocyte α-defensins.

To determine which leukocytic lineages express RTD-1, cytospin preparations of peripheral blood buffy coat cells, fixed with 4% paraformaldehyde, were incubated with 1:100 rabbit anti-RTD-1 antiserum and developed with biotinylated goat anti-rabbit IgG. The fixed cells were washed and incubated with avidin/biotin/glucose oxidase complex, which was subsequently visualized with nitroblue tetrazolium. Cells were counterstained with Nuclear Fast Red. For a negative control, buffy coat cells were incubated with anti-RTD-1 antiserum that was preabsorbed with synthetic acyclic RTD-1 (1 mg per ml antiserum).

Figure 11:
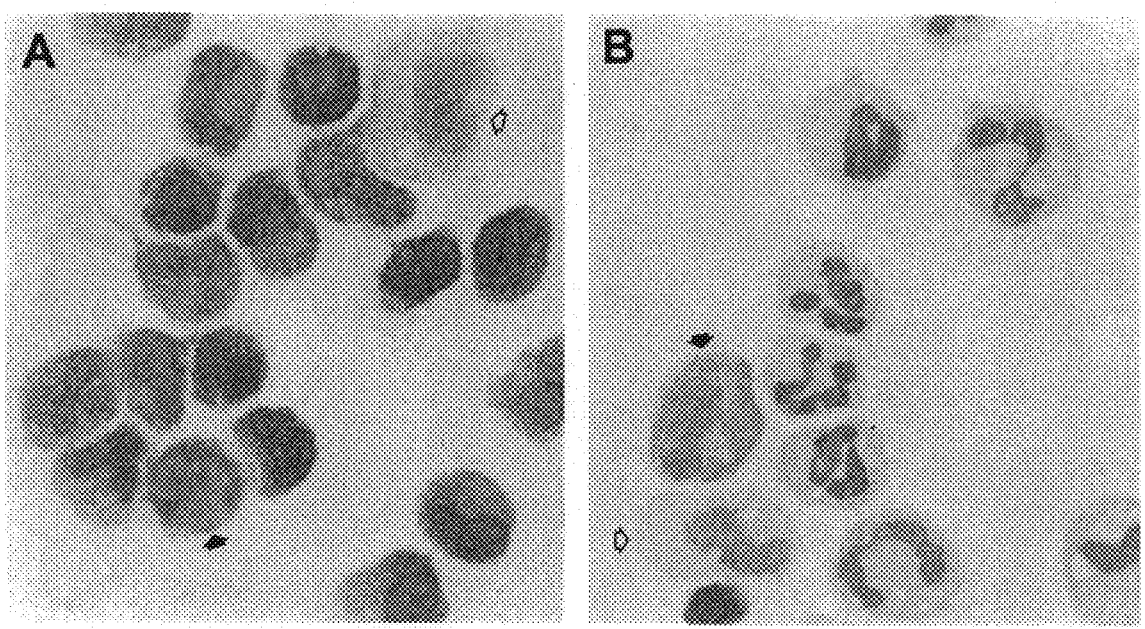
FIGS. 11A and 11B show the immunolocalization of RTD-1 in rhesus macaque leukocytes.

Immunostaining of buffy coat leukocytes demonstrated strong, punctate staining in neutrophil cytoplasm, similar to immunolocalization studies of neutrophil α-defensins, which are stored in azurophil granules (FIG. 11). Though staining less strongly than neutrophils, monocytes were also immunopositive, while lymphocytes and eosinophils were negative. These results demonstrate the presence of RTD-1 in the two major phagocytic cells of the blood.

EXAMPLE V

Theta Defensin is the Product of Two Independent Genes Encoding Distinct Portions of Theta Defensin This example describes the cloning of two distinct theta defensin genes from macaques, each gene encoding a specific portion of theta defensin.

In order to understand the transcriptional and translational pathways involved in the production of cyclic RTD-1, the corresponding cDNA was cloned. The finding that RTD-1 is expressed in myeloid cells suggested that its mRNA would be abundant in bone marrow cells. Using rhesus macaque bone marrow mRNA as template, 3' rapid amplification of cDNA ends (RACE) was carried out using degenerate primers corresponding to different 6 or 7 amino acid sequences in the RTD-1 backbone. Polymerase chain reaction (PCR) products were subcloned and sequenced, revealing that portions of the RTD-1 mature peptide sequence were amplified using the degenerate primer corresponding to GVCRCIC (SEQ ID NO:30). The 3' RACE products were then used to probe a rhesus macaque bone marrow cDNA library. Fifteen positive clones were isolated and sequenced, disclosing two very similar cDNAs termed RTD1a and RTD1b.

FIG. 12 shows the full length cDNAs of RTD1a (SEQ ID NO:13) and RTD1b (SEQ ID NO:15) and the corresponding deduced amino acid sequences (SEQ ID NOS:14 and 16, respectively). Full length cDNA sequences are shown with the deduced amino acid sequences. Underlined amino acids are found in RTD-1, and superscript numbers correspond to the residue numbering of RTD-1 shown in FIG. 2B. ATG of the initiation methionines are in bold, as are the polyadenlation sites at the 3' ends of the sequences (FIG. 12).

At the DNA level, both clones showed a high degree of identity, 90.8% and 91.2% for RTD1a and RTD1b, respectively, to regions of a human defensin-related pseudogene, GI501091, GenBank accession number U10267. One of the stop codons in this human sequence corresponds exactly to the position of the stop codon in the RTD-1 sequences (FIG. 12).

Figures 13A, 13B:
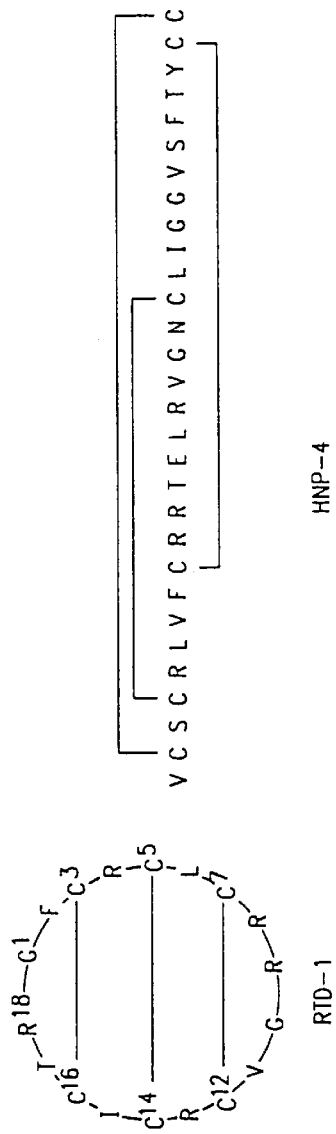
FIGS. 13A and 13B show the amino acid sequences of RTD1a, RTD1b, and human neutrophil defensin HNP-4.

At the amino acid level, the RTD-1 precursors were most similar to HNP-4, one of the four known human myeloid α-defensins (FIG. 13). α-defensins are antimicrobial peptides expressed at high levels in neutrophils, in Paneth cells of the small intestine, and in a number of other specialized epithelia. Although the RTD-1 and α-defensin sequences and disulfide structures are quite different (FIG. 13), the RTD1a and RTD1b mRNAs encode polypeptides that are very similar in sequence to myeloid α-defensin precursors (43% identity). However, RTD 1a and 1b appear to be truncated α-defensins, as stop codons are present in the coding sequences about half way through the open reading frame corresponding to the mature α-defensin peptides (FIG. 13).

Inspection of the RTD1a and RTD1b cDNAs revealed that they each encode 76 amino acid prepropeptides in which are contained 9 of the 18 residues in the mature RTD-1 peptide. From RTD1a, amino acids 65 to 73 correspond to RTD-1 residues 13 to 18 and 1 to 3. In RTD1b, the same residues 65 to 73 in the precursor correspond to RTD-1 amino acids 4 to 12 (FIGS. 12 and 13). A tripeptide at the carboxyl end of each precursor is removed prior to a pair of ligation events necessary for peptide cyclization.

The RTD1.1 and RTD1.2 genomic sequences were determined, confirming that the corresponding cDNAs derive from distinct transcriptional units (FIG. 14). The 3 exon, 2 intron gene structure and organization are very similar to that of the myeloid α-defensins characterized in humans, rabbits, and guinea pigs.

Expression of RTD-1 mRNA was analyzed by northern blotting of RNA from selected rhesus tissues using a random prime labeled PCR product containing nucleotides 200 to 231 in RTD1a and 195 to 326 in RTD1b. The DNA probe for specific hybridization to RTD1a and RTD1b is shown in FIG. 15. Hybridization was performed at 42° C. overnight in 5×SSPE (20×SSPE is 3M NaCl, 0.2M phosphate, pH 7.4, 0.025M ethylenediaminetetraacetic acid (EDTA); 4×Denhardt's (50×Denhardt's is 1% Ficoll 1% polyvinylpyrrolidone, 1% bovine serum albumin (BSA)); 4.8% sodium dodecyl sulfate (SDS); and 40% formamide. The blots were washed at 42° C., followed by washing at 50° C. with 0.5×SSC (20×SSC is 3M NaCl, 0.3M sodium citrate, pH 7.0) and 2% SDS. These probes were shown to be specific for RTD-1 by Southern slot blot analysis, as they did not hybridize to plasmids containing known rhesus myeloid defensin cDNAs in Southern Blots, but they hybridized strongly to plasmids containing the RTD1a and RTD1b cDNAs.

Various tissues were analyzed for expression of RTD-1 mRNA, including lymph node, stomach, thyroid, jejunum, liver, adrenal, thymus, kidney, lung, pancreas, ovary, colonic mucosa, trachea, spleen, bone marrow, skeletal muscle, brain, and testis. RTD-1 mRNA was detected only in bone marrow. The hybridizing signal was 0.54 kb, consistent with the size of the cDNA.

Human theta defensin cDNA was also isolated. The human theta defensin cDNA was amplified from human bone marrow cDNA using primers deduced from RTD1a and RTD1b. FIG. 16 shows the human theta defensin cDNA sequence (SEQ ID NO:28) and the deduced amino acid sequence (SEQ ID NO:29). The human theta defensin peptide region corresponds to amino acid residues 65 to 73 in the precursor (SEQ ID NO:18).

To confirm that RTD-1 is in fact produced by the ligation of RTD-1a and RTD-1b gene products, transfection experiments were conducted using the human promyelocytic cell line HL-60. Since synthesis of azurophil granule contents occurs through the promyelocyte stage, it was likely that the cellular machinery for synthesis and processing RTD-1 would exist in this cell line.

Figure 17:
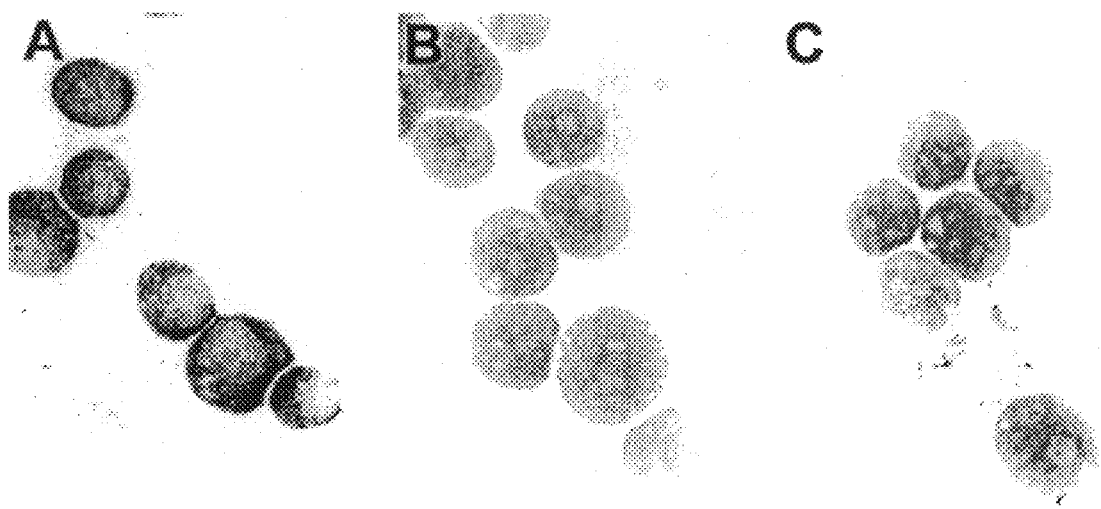
FIGS. 17A, 17B and 17C show immunostaining of HL-60 cells transfected with pcDNA3.1 containing RTD1a and RTD1b cDNAs.

Cells were transfected with pcDNA3.1 (Invitrogen; San Diego Calif.) constructs containing the RTD1a and RTD1b coding sequences downstream of the CMV immediate early promoter. Stable transfectants and control HL-60 cells were immunostained with anti-RTD-1 antibody (see Example IV). As shown in FIG. 17, cells transfected with vectors containing the RTD1a and RTD1b cDNAs were strongly immunopositive (FIG. 17A). Non-transfected cells (FIG. 17B) stained with anti-RTD-1 anti-serum were immunonegative, as were transfected cells stained with preimmune serum (FIG. 17C). These data confirm the relationship between RTD-1 peptide and the two cDNAs, and indicate that transfected HL-60 cells may be useful for studying the processing pathway leading to the final cyclic structure.

These results demonstrate that RTD-1 peptide is the product of two genes, RTD-1a and RTD-1b, which are expressed and processed to form the RTD-1 theta defensin.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. An isolated nucleic acid molecule encoding a theta defensin, or a functional fragment thereof, wherein said theta defensin or functional fragment is a cationic, arginine-rich cyclic peptide having each amino acid linked by a peptide bond and having one or more intrachain crosslinks, said intrachain crosslink formed between two amino acids, said theta defensin peptide or functional fragment having antimicrobial activity.

2. An isolated nucleic acid molecule ending a theta defensin peptide comprising the amino acid sequence:
Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8,
wherein:
Xaa1 independently is Gly, Ile, Leu, Val or Ala;
Xaa2 is Phe, Trp or Tyr;
Xaa3 is Cys or Trp;
Xaa4 independently is Arg or Lys;
Xaa5 is Cys or Trp;
Xaa6 is Cys or Trp;
Xaa7 is Thr or Ser; and
Xaa8 is Arg or Lys,
or a nucleic acid molecule complementary thereto.

3. The nucleic acid molecule of claim 2, wherein said theta defensin peptide has the amino acid sequence:
Gly-Phe-Cys-Arg-Cys-Leu-Cys-Arg-Arg-Gly-Val-Cys-Arg-Cys-Ile-Cys-Thr-Arg (SEQ ID NO:1).

4. The nucleic acid molecule of claim 1, said nucleic acid molecule comprising the RTD1a nucleotide sequence referenced as SEQ ID NO:17.

5. The nucleic acid molecule of claim 1, said nucleic acid molecule comprising the RTD1b nucleotide sequence referenced as SEQ ID NO:19.

6. The nucleic acid molecule of claim 1, said nucleic acid molecule comprising the RTD1a nucleotide sequence referenced as SEQ ID NO:13.

7. The nucleic acid molecule of claim 1, said nucleic acid molecule comprising the RTD1b nucleotide sequence referenced as SEQ ID NO:15.

8. The nucleic acid molecule of claim 1, said nucleic acid molecule consisting of the RTD1a nucleotide sequence referenced as SEQ ID NO: 24.

9. The nucleic acid molecule of claim 1, said nucleic acid molecule consisting of the RTD1b nucleotide sequence referenced as SEQ ID NO: 25.

10. The nucleic acid molecule of claim 1, said nucleic acid molecule comprising the human theta defensin nucleotide sequence referenced as SEQ ID NO:28.

11. A vector encoding a theta defensin, said vector comprising an expression element operationally linked to a nucleotide sequence encoding a theta defensin peptide, said nucleotide sequence comprising the nucleic acid molecule of any of claims 1 to 10.

12. A method of expressing a theta defensin, comprising
(a) administering the vector of claim 11 to a cell; and
(b) expressing said encoded theta defensin peptides, wherein said peptides form a theta defensin.

13. The method of claim 12, wherein said vector encodes two theta defensin peptides.

14. The method of claim 12, wherein a second vector encoding a second theta defensin peptide is administered to said cell.

15. An isolated nucleic acid molecule encoding a theta defensin peptide comprising the amino acid sequence:
Xaa1-Xaa2-Xaa9-Xaa4-Xaa10-Xaa1-Xaa11-Xaa4-Xaa4-Xaa1-Xaa1-Xaa12-Xaa4-Xaa13-Xaa1-Xaa14-Xaa7-Xaa8,
wherein:
Xaa1 independently is an aliphatic amino acid;
Xaa2 is an aromatic amino acid;
Xaa4 independently is Arg or Lys;
Xaa7 is Thr or Ser;
Xaa8 is Arg or Lys;
Xaa9 is Glu, Asp, Lys or Ser;
Xaa10 is Glu, Asp, Lys or Ser;
Xaa11 is Glu, Asp, Lys or Ser;
Xaa12 is Glu, Asp, Lys or Ser;
Xaa13 is Glu, Asp, Lys or Ser;
Xaa14 is Glu, Asp, Lys or Ser.

16. An isolated nucleic acid molecule encoding a theta defensin peptide comprising the amino acid sequence:

Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8, wherein:
- Xaa1 independently is an aliphatic amino acid;
- Xaa2 is an aromatic amino acid;
- Xaa3 is Cys or Trp;
- Xaa4 independently is Arg or Lys;
- Xaa5 is Cys or Trp;
- Xaa6 is Cys or Trp;
- Xaa7 is Thr or Ser; and
- Xaa8 is Arg or Lys, said theta defensin having an intrachain crosslink formed between two amino acids selected from the group consisting of:
  - Xaa3 at position 3 and Xaa3 at position 16;
  - Xaa5 at position 5 and Xaa5 at position 14; and
  - Xaa6 at position 7 and Xaa6 at position 12.

17. The nucleic acid molecule of claim 16 having the amino acid sequence:

Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8, wherein:
- Xaa1 independently is Gly, le, Leu, Val or Ala;
- Xaa2 is Phe, Trp, or Tyr;
- Xaa3 is Cys or Trp;
- Xaa4 independently is Arg or Lys;
- Xaa5 is Cys or Trp;
- Xaa6 is Cys or Trp;
- Xaa7 is Thr or Ser; and
- Xaa8 is Arg or Lys, said theta defensin having an intrachain crosslink formed between two amino acids selected from the group consisting of:
  - Xaa3 at position 3 and Xaa3 at position 16;
  - Xaa5 at position 5 and Xaa5 at position 14; and
  - Xaa6 at position 7 and Xaa6 at position 12.

18. An isolated nucleic acid encoding a theta defensin peptide having the amino acid sequence:

Xaa1-Xaa2-Xaa9-Xaa4-Xaa10-Xaa1-Xaa11-Xaa4-Xaa4-Xaa1-Xaa1-Xaa12-Xaa4-Xaa13-Xaa1-Xaa14-Xaa7-Xaa8, wherein:
- Xaa1 independently is an aliphatic amino acid:
- Xaa2 is an aromatic amino acid;
- Xaa4 independently is Arg or Lys;
- Xaa7 is Thr or Ser;
- Xaa8 is Arg or Lys;
- Xaa9 is Glu, Asp, Lys or Ser;
- Xaa10 is Glu, Asp, Lys or Ser;
- Xaa11 is Glu, Asp, Lys or Ser;
- Xaa12 is Glu, Asp, Lys or Ser;
- Xaa13 is Glu, Asp, Lys or Ser;
- Xaa14 is Glu, Asp, Lys or Ser, wherein an intrachain crosslink is formed between two amino acids selected from the group consisting of:
  - Xaa9 and Xaa14;
  - Xaa10 and Xaa13; and
  - Xaa11 and Xaa12.

19. An isolated nucleic acid encoding a theta defensin peptide comprising the amino acid sequence of SEQ ID NO: 18, said peptide having antimicrobial activity.

20. An isolated nucleic acid encoding a theta defensin peptide comprising the amino acid sequence of SEQ ID NO: 20, said peptide having antimicrobial activity.

* * * * *

```
                         SEQUENCE LISTING

<160> NUMBER OF SEQ ID NOS: 31

<210> SEQ ID NO 1
    <211> LENGTH: 18
    <212> TYPE: PRT
    <213> ORGANISM: Macaca mulatta

<400> SEQUENCE: 1

Gly Phe Cys Arg Cys Leu Cys Arg Arg Gly Val Cys Arg Cys Ile Cys
     1               5                  10                  15

Thr Arg

<210> SEQ ID NO 2
    <211> LENGTH: 4
    <212> TYPE: PRT
    <213> ORGANISM: Macaca mulatta

<400> SEQUENCE: 2

Gly Phe Cys Arg
     1

<210> SEQ ID NO 3
    <211> LENGTH: 4
    <212> TYPE: PRT
    <213> ORGANISM: Macaca mulatta

<400> SEQUENCE: 3

Cys Arg Cys Leu
     1

<210> SEQ ID NO 4
    <211> LENGTH: 4
    <212> TYPE: PRT
    <213> ORGANISM: Macaca mulatta

<400> SEQUENCE: 4

Cys Leu Cys Arg
     1

<210> SEQ ID NO 5
    <211> LENGTH: 6
    <212> TYPE: PRT
    <213> ORGANISM: Macaca mulatta

<400> SEQUENCE: 5

Cys Arg Arg Gly Val Cys
     1               5

<210> SEQ ID NO 6
    <211> LENGTH: 5
    <212> TYPE: PRT
```

<213> ORGANISM: Macaca mulatta

<400> SEQUENCE: 6

Arg Gly Val Cys Arg
 1               5

<210> SEQ ID NO 7
<211> LENGTH: 8
<212> TYPE: PRT
<213> ORGANISM: Macaca mulatta

<400> SEQUENCE: 7

Arg Cys Ile Cys Thr Arg Gly Phe
 1               5

<210> SEQ ID NO 8
<211> LENGTH: 5
<212> TYPE: PRT
<213> ORGANISM: Macaca mulatta

<400> SEQUENCE: 8

Cys Ile Cys Thr Arg
 1               5

<210> SEQ ID NO 9
<211> LENGTH: 18
<212> TYPE: PRT
<213> ORGANISM: Macaca mulatta

<400> SEQUENCE: 9

Thr Arg Gly Phe Cys Arg Cys Leu Cys Arg Arg Gly Val Cys Arg Cys
 1               5                  10                  15

Ile Cys

<210> SEQ ID NO 10
<211> LENGTH: 30
<212> TYPE: PRT
<213> ORGANISM: Chassalia parviflora

<400> SEQUENCE: 10

Asn Lys Val Cys Tyr Arg Asn Gly Ile Pro Cys Gly Glu Ser Cys Val
 1               5                  10                  15

Trp Ile Pro Cys Ile Ser Ala Ala Leu Gly Cys Ser Cys Lys
             20                  25                  30

<210> SEQ ID NO 11
<211> LENGTH: 18
<212> TYPE: PRT
<213> ORGANISM: Sus scrofa

<400> SEQUENCE: 11

Arg Gly Gly Arg Leu Cys Tyr Cys Arg Arg Arg Phe Cys Val Cys Val
 1               5                  10                  15

Gly Arg

<210> SEQ ID NO 12
<211> LENGTH: 30
<212> TYPE: PRT
<213> ORGANISM: Homo sapiens

<400> SEQUENCE: 12

Val Cys Ser Cys Arg Leu Val Phe Cys Arg Arg Thr Glu Leu Arg Val
 1               5                  10                  15

```
Gly Asn Cys Leu Ile Gly Gly Val Ser Phe Thr Tyr Cys Cys
            20                  25                  30

<210> SEQ ID NO 13
<211> LENGTH: 500
<212> TYPE: DNA
<213> ORGANISM: Macaca mulatta
<220> FEATURE:
<221> NAME/KEY: CDS
<222> LOCATION: (95)..(325)

<400> SEQUENCE: 13
gacggctgct gttgctacag gagacccagg acagaggact gctgtctgca ctctctcttc      60
actctgccta acttgaggat ctgtcactcc agcc atg agg acc ttc gcc ctc ctc     115
                                     Met Arg Thr Phe Ala Leu Leu
                                       1               5 acc gcc atg ctt ctc ctg gtg gcc ctg cac gct cag gca gag gca cgt       163
Thr Ala Met Leu Leu Leu Val Ala Leu His Ala Gln Ala Glu Ala Arg
         10                  15                  20 cag gca aga gct gat gaa gct gcc gcc cag cag cag cct gga aca gat       211
Gln Ala Arg Ala Asp Glu Ala Ala Ala Gln Gln Gln Pro Gly Thr Asp
     25                  30                  35 gat cag gga atg gct cat tcc ttt aca tgg cct gaa aac gcc gct ctt       259
Asp Gln Gly Met Ala His Ser Phe Thr Trp Pro Glu Asn Ala Ala Leu
 40                  45                  50                  55 cca ctt tca gag tca gcg aaa ggc ttg agg tgc att tgc aca cga gga       307
Pro Leu Ser Glu Ser Ala Lys Gly Leu Arg Cys Ile Cys Thr Arg Gly
                 60                  65                  70 ttc tgc cgt ttg tta taa tgtcaccttg ggtcctgcgc ttttcgtggt              355
Phe Cys Arg Leu Leu
             75 tgactccacc ggatctgctg ccgctgagct tccagaatca agaaaaatat gctcagaagt     415 tactttgaga gttaaaagaa attcttgcta ctgctgtacc ttctcctcag tttccttttc     475 tcatcccaaa taaataccct atcgc                                           500

<210> SEQ ID NO 14
<211> LENGTH: 76
<212> TYPE: PRT
<213> ORGANISM: Macaca mulatta

<400> SEQUENCE: 14

Met Arg Thr Phe Ala Leu Leu Thr Ala Met Leu Leu Leu Val Ala Leu
  1               5                  10                  15

His Ala Gln Ala Glu Ala Arg Gln Ala Arg Ala Asp Glu Ala Ala Ala
             20                  25                  30

Gln Gln Gln Pro Gly Thr Asp Asp Gln Gly Met Ala His Ser Phe Thr
         35                  40                  45

Trp Pro Glu Asn Ala Ala Leu Pro Leu Ser Glu Ser Ala Lys Gly Leu
     50                  55                  60

Arg Cys Ile Cys Thr Arg Gly Phe Cys Arg Leu Leu
 65                  70                  75

<210> SEQ ID NO 15
<211> LENGTH: 495
<212> TYPE: DNA
<213> ORGANISM: Macaca mulatta
<220> FEATURE:
<221> NAME/KEY: CDS
<222> LOCATION: (90)..(320)
```

<400> SEQUENCE: 15

```
gaccgctgct cttgctacag gagacccggg acagaggact gctgtctgcc ctctctcttc      60
actctgccta acttgaggat ctgccagcc atg agg acc ttc gcc ctc ctc acc       113
                                 Met Arg Thr Phe Ala Leu Leu Thr
                                  1               5 gcc atg ctt ctc ctg gtg gcc ctg cac gct cag gca gag gca cgt cag       161
Ala Met Leu Leu Leu Val Ala Leu His Ala Gln Ala Glu Ala Arg Gln
     10              15                  20 gca aga gct gat gaa gct gcc gcc cag cag cag cct gga gca gat gat       209
Ala Arg Ala Asp Glu Ala Ala Ala Gln Gln Gln Pro Gly Ala Asp Asp
 25              30                  35                  40 cag gga atg gct cat tcc ttt aca cgg cct gaa aac gcc gct ctt ccg       257
Gln Gly Met Ala His Ser Phe Thr Arg Pro Glu Asn Ala Ala Leu Pro
                 45                  50                  55 ctt tca gag tca gcg aga ggc ttg agg tgc ctt tgc aga cga gga gtt       305
Leu Ser Glu Ser Ala Arg Gly Leu Arg Cys Leu Cys Arg Arg Gly Val
                 60                  65                  70 tgc caa ctg tta taa aggcgtttgg ggtcctgcgc ttttcgtggt tgactctgcc      360
Cys Gln Leu Leu
         75 ggatctgctg ccgctgagct tccagaatca agaaaaatac gctcagaagt tactttgaga    420 gttgaaagaa attcctgtta ctcctgtacc ttgtcctcaa tttccttttc tcatcccaaa    480 taaatacctt ctcgc                                                      495
```

<210> SEQ ID NO 16
<211> LENGTH: 76
<212> TYPE: PRT
<213> ORGANISM: Macaca mulatta

<400> SEQUENCE: 16

```
Met Arg Thr Phe Ala Leu Leu Thr Ala Met Leu Leu Leu Val Ala Leu
 1               5                  10                  15

His Ala Gln Ala Glu Ala Arg Gln Ala Arg Ala Asp Glu Ala Ala Ala
             20                  25                  30

Gln Gln Gln Pro Gly Ala Asp Asp Gln Gly Met Ala His Ser Phe Thr
         35                  40                  45

Arg Pro Glu Asn Ala Ala Leu Pro Leu Ser Glu Ser Ala Arg Gly Leu
     50                  55                  60

Arg Cys Leu Cys Arg Arg Gly Val Cys Gln Leu Leu
 65                  70                  75
```

<210> SEQ ID NO 17
<211> LENGTH: 27
<212> TYPE: DNA
<213> ORGANISM: Macaca mulatta
<220> FEATURE:
<221> NAME/KEY: CDS
<222> LOCATION: (1)..(27)

<400> SEQUENCE: 17

```
agg tgc att tgc aca cga gga ttc tgc                                   27
Arg Cys Ile Cys Thr Arg Gly Phe Cys
 1               5
```

<210> SEQ ID NO 18
<211> LENGTH: 9
<212> TYPE: PRT
<213> ORGANISM: Macaca mulatta

<400> SEQUENCE: 18

```
Arg Cys Ile Cys Thr Arg Gly Phe Cys
 1               5
```

<210> SEQ ID NO 19
<211> LENGTH: 27
<212> TYPE: DNA
<213> ORGANISM: Macaca mulatta
<220> FEATURE:
<221> NAME/KEY: CDS
<222> LOCATION: (1)..(27)

<400> SEQUENCE: 19

```
agg tgc ctt tgc aga cga gga gtt tgc                              27
Arg Cys Leu Cys Arg Arg Gly Val Cys
 1               5
```

<210> SEQ ID NO 20
<211> LENGTH: 9
<212> TYPE: PRT
<213> ORGANISM: Macaca mulatta

<400> SEQUENCE: 20

```
Arg Cys Leu Cys Arg Arg Gly Val Cys
 1               5
```

<210> SEQ ID NO 21
<211> LENGTH: 92
<212> TYPE: PRT
<213> ORGANISM: Macaca mulatta

<400> SEQUENCE: 21

```
Met Arg Thr Phe Ala Leu Leu Thr Ala Met Leu Leu Val Ala Leu
 1               5                  10                  15

His Ala Gln Ala Glu Ala Arg Gln Ala Arg Ala Asp Glu Ala Ala Ala
                 20                  25                  30

Gln Gln Gln Pro Gly Thr Asp Asp Gln Gly Met Ala His Ser Phe Thr
         35                  40                  45

Trp Pro Glu Asn Ala Ala Leu Pro Leu Ser Glu Ser Ala Lys Gly Leu
     50                  55                  60

Arg Cys Ile Cys Thr Arg Gly Phe Cys Arg Leu Leu Cys His Leu Gly
 65                  70                  75                  80

Ser Cys Ala Phe Arg Gly Leu His Arg Ile Cys Cys
                 85                  90
```

<210> SEQ ID NO 22
<211> LENGTH: 92
<212> TYPE: PRT
<213> ORGANISM: Macaca mulatta

<400> SEQUENCE: 22

```
Met Arg Thr Phe Ala Leu Leu Thr Ala Met Leu Leu Val Ala Leu
 1               5                  10                  15

His Ala Gln Ala Glu Gln Arg Gln Ala Arg Ala Asp Glu Ala Ala Ala
                 20                  25                  30

Gln Gln Gln Pro Gly Ala Asp Asp Gln Gly Met Ala His Ser Phe Thr
         35                  40                  45

Arg Pro Glu Asn Ala Ala Leu Pro Leu Ser Glu Ser Ala Arg Gly Leu
     50                  55                  60

Arg Cys Leu Cys Arg Arg Gly Val Cys Gln Leu Leu Arg Arg Leu Gly
 65                  70                  75                  80
```

Ser Cys Ala Phe Arg Gly Leu Cys Arg Ile Cys Cys
            85                  90

<210> SEQ ID NO 23
<211> LENGTH: 97
<212> TYPE: PRT
<213> ORGANISM: Macaca mulatta

<400> SEQUENCE: 23

Met Arg Ile Ile Ala Leu Leu Ala Ala Ile Leu Leu Val Ala Leu Gln
 1               5                  10                  15

Val Arg Ala Gly Pro Leu Gln Ala Arg Gly Asp Glu Ala Pro Gly Gln
            20                  25                  30

Glu Gln Arg Gly Pro Glu Asp Gln Asp Ile Ser Ile Ser Phe Ala Trp
        35                  40                  45

Asp Lys Ser Ser Ala Leu Gln Val Ser Gly Ser Thr Arg Gly Met Val
    50                  55                  60

Cys Ser Cys Arg Leu Val Phe Cys Arg Arg Thr Glu Leu Arg Val Gly
65                  70                  75                  80

Asn Cys Leu Ile Gly Gly Val Ser Phe Thr Tyr Cys Cys Thr Arg Val
                85                  90                  95

Asp

<210> SEQ ID NO 24
<211> LENGTH: 2525
<212> TYPE: DNA
<213> ORGANISM: Macaca mulatta

<400> SEQUENCE: 24

| | | | | | |
|---|---|---|---|---|---|
| gacggctgct | gttgctacag | gagacccagg | acagaggact | gctgtctgca | ctctctcttc | 60 |
| actctgccta | acttgaggat | ctgtaagtaa | cacaaaactt | aaactttcct | gtcgaggttt | 120 |
| gaacattgaa | gctgtgcccc | taatctgacc | tgtgactcct | gggccacccc | agagagacct | 180 |
| agtgggtgaa | tcccctgctg | tgcatttctg | tctgaacctc | tgggggctgc | tgggagcatt | 240 |
| ggctaccagc | tcaattaata | gagaaactca | aggaatttcc | ttctaattac | atgtgtccta | 300 |
| cttgacacat | ccaacagaga | caacaatagc | tccttaaaac | acccttttgt | ttggagagaa | 360 |
| gccaatccag | atcctcggcc | tgttttttcaa | tcaggttatt | tgttatttac | tattgagttg | 420 |
| tttgactgcc | ttatgtattt | agatatttac | cccttctacc | acttaggatt | tgcaactatc | 480 |
| gtctttcatt | ttctgggttg | cttttttcact | cagttgatta | tttgtttgtt | ggttttttga | 540 |
| cgtgcagatg | ctttagaggt | cagtgcagcc | ccacttgcct | cttttcccat | ttattgcctg | 600 |
| tgtctttggt | gtcatagcaa | agatatcatt | accaacatca | atgtcaaagc | gtcatcttca | 660 |
| tatattcctc | tcgtcgtttt | atggtttcag | gtctatgttt | gggtcttcaa | tccattttga | 720 |
| gttgatttgt | gaaatagata | tgataaggcc | acatgtatca | aacatcaaat | cctaaggtgc | 780 |
| agacagtaga | tatataccat | tttnattctt | attcacatct | ctatagagct | ggaaacaaat | 840 |
| ttttggctgt | agatgaactt | tttacctcga | tatgtcagtg | ttcatttcac | ctatcatatg | 900 |
| atagggtcat | tgttctcttc | acactggccc | ctacaggagg | ctactcaccc | catgccttcg | 960 |
| ggagtgtggt | caagcccttg | atgcctccaa | taaatgactc | tttacttgat | aggaaatcat | 1020 |
| acctgctgcc | agagtgtaga | cctacagaga | gtagtagggc | catctgcagg | aagagacatt | 1080 |
| tgtcgcctga | cctcattgaa | taaatcact | gctgttatcc | tttgctagaa | gagttaaaag | 1140 |
| taaatatttc | gtaaagtgag | aaacaggaat | cctcatcatc | atcctcatca | aaccagcaca | 1200 |

| | |
|---|---|
| gacactaaac atagagattc aaactagagt gaaagctggg agaccaaaag aagaaaacat | 1260 |
| ggacattgag accaatggga tcccacacaa tctccagtga aatgcacacc tcctctctct | 1320 |
| gagaaggttc aaggtttcct gtctctgagc ctcctctctg cagacataga aatccagact | 1380 |
| aactcctctc tcccgacttg tccgctcctg ctctgcctct tccaggtcac tccagccatg | 1440 |
| aggaccttcg ccctcctcac cgccatgctt ctcctggtgg ccctgcacgc tcaggcagag | 1500 |
| gcacgtcagg caagagctga tgaagctgcc gcccagcagc agcctggaac agatgatcag | 1560 |
| ggaatggctc attcctttac atggcctgaa acgccgctc ttccactttc aggtgagaca | 1620 |
| ggccggcatg cagagctgca gggtctagag ggatggatgg gagacagagt cgggaatcga | 1680 |
| gtctcagtgg tccttgtcac ctagatggct tcatttagca tctctgggcc ttggttttct | 1740 |
| catctataaa ttgaatacag aaccaaataa atctagcagg tttctgtcta taaagacttg | 1800 |
| aggcagctct gcctggagag taaccattct tttattcctt tacttcctta acgatccttt | 1860 |
| cactttagaa aatcaataaa attaaaaaat aagacttgaa atcaacatat gtctgtgaaa | 1920 |
| ttcagtaggt ttaagatatg aagaaacagt ctgctagttc tttctggatt caaacaagtc | 1980 |
| atcttcatta catggataat atttgactgt atctatacaa ccgtttctaa gagtagagac | 2040 |
| aagcctaaga gtgcgttcag gtgtgtgtct gatgggcaga agcacaaaaa atgaaagcaa | 2100 |
| atgagaataa gtctcaaatc ctgtatgacc agcactgctc tgtgtattta ttcttaatga | 2160 |
| ctgaagttgt tcatgctacc ggccctaatg cagccgacat cactcattag ctagcacatg | 2220 |
| acttctccag gattcccttt gccacccact gctgaccttc tgatccattt acgatgctct | 2280 |
| ctctgtgttc ccagagtcag cgaaaggctt gaggtgcatt tgcacacgag gattctgccg | 2340 |
| tttgttataa tgtcaccttg ggtcctgcgc ttttcgtggt tgactccacc ggatctgctg | 2400 |
| ccgctgagct tccagaatca agaaaaatat gctcagaagt tactttgaga gttaaaagaa | 2460 |
| attcttgcta ctgctgtacc ttctcctcag tttccttttc tcatcccaaa taaataccttt | 2520 |
| ctcgc | 2525 |

<210> SEQ ID NO 25
<211> LENGTH: 2553
<212> TYPE: DNA
<213> ORGANISM: Macaca mulatta

<400> SEQUENCE: 25

| | |
|---|---|
| gaccgctgct cttgctacag gagacccggg acagaggact gctgtctgcc ctctctcttc | 60 |
| actctgccta acttgaggat ctgtaagtaa cacaaaactt aaactttcct gtcgaggttt | 120 |
| gaacattgaa gctgtgcacc caatctgacc tgtgactcct ggggccacccc agagggacct | 180 |
| agtgggtgaa tcccctgctg tgcatttctg tctgaacctc tgggggctgc tgggagcatt | 240 |
| ggctaccagc tcaattaata gagaaactca agaaatttcc ttctacttac acgtgtccta | 300 |
| cttgacacgt ccaacagaga caacaatagc tccttaaaac accctttat ttggagagaa | 360 |
| gccgatcctg ctcctcggcc tattttttcaa tcaggttatt tcttatttgc tactgagttg | 420 |
| tttgattgcc ttatgcattt agatgttcac cctttctacc acttagggtt tgcaactatt | 480 |
| gtctttcatt ttctgagttg cttttttcact cagttgatta tttatttgtt ggtttggttt | 540 |
| tttgacgtgc atttgcttta gaggtcagtg cagccccact tgtctctttt cccgtttatt | 600 |
| gcctgtgtct tggtgtcat agcaaagata tcattaccaa catcaatgtc aaagcattat | 660 |
| cttcatatgt tcctctcgtc gtttacggtt tcaggactat gtttgggtct tcaatccatt | 720 |
| ttgagttggt ttgtgaaata gatatgataa agaccacatg tatcaaacat caaatcctaa | 780 |

```
ggtggagtac agtagatata taccattttt cattcttatt catatctcta tagagctgga      840
aatgaatttt tcagtgtaga tgaaattttg accttgatat cactgtgttc atttcaccta      900
tcgcatgata gggtcattgt cctcttcaca ttggcccta caggaggcta cacacctcat       960
gccttcatga gagtgatcat gcctatgatg cctgcaacaa atcactcttc acttgacagg     1020
aaattcatgc ctgctgccag agtgtagacc catagagagt cgtggggcca tctgaaggaa     1080
aggagacatt tgtatcctga acttactgaa caaagcactg ctgttatcct ttggtagaac     1140
agtaaaaagt aaatatgtaa tgaagtgaga acaggagaa agatgccagg ttcctcatct      1200
tcaccatcct ctccatcagc acagacacta aacatagaga ttcaaactag agtgaaagct     1260
gggagagcaa aagaagaaaa catggacatt gagaccaatg ggatcccata caatctccag     1320
tgaaatgcac agctcctctc tctgagaagg ttcaagattt cctgtctctg agccttctct     1380
ctgcagacat agaaatccag actaactcct ctctcccgac ttgtctgctc ctgctcttcc     1440
tcctccaggt cactccagcc atgaggacct cgccctcct caccgccatg cttctcctgg      1500
tggccctgca cgctcaggca gaggcacgtc aggcaagagc tgatgaagct gccgcccagc     1560
agcagcctgg agcagatgat cagggaatgg ctcattcctt tacacggcct gaaaacgccg     1620
ctcttccgct tcaggtgag acaggccggc atgcagagct cagggtcta gagggatgga      1680 tgggagacag agtcgggaat cgagtctcag tggtccatgt cacctagatg gcttcattta     1740
gcatctctgg gccttggttt tctcatctat aaattgaata gagagccaaa gaagtctaac     1800
aggttttctg tctataaaga tttgaggcag ctctgcctgg agagtaacca ttcttttatt     1860
cccttacttc cttaatgatc ctttcacttt agagaatcaa taaaattaaa aaataaaact     1920
tgaaatcaag atatgtctgt gaaattcaag taggtttaag acatgaagag acagtctgac     1980
tagttctttc tggattcaaa caagtcatct tcattacacg gagaatattt gactgtatct     2040
atacaaccgt ttctaagagt agagacaagc ctaagagtgc attcaggtgt ttgtgtttga     2100
tggggcacag gcacaaaaat gagagcaaat gagaataagt ctcaaatcct gtgtgaccag     2160
cactactctg tgtatttatt cctactgact gaggttgttc atgctaccgg cccgaatgca     2220
gctgacatcc ctcattagct agcacatgac ttctccagga ttccctttgt cactcactgc     2280
agaccttctg atccatttat gatgctttct ctgtgtcccc agagtcagcg agaggcttga     2340
ggtgcctttg cagacgagga gtttgccaac tgttataaag gcgtttgggg tcctgcgctt     2400
ttcgtggttg actctgccgg atctgctgcc gctgagcttc cagaatcaag aaaaatacgc     2460
tcagaagtta ctttgagagt tgaaagaaat tcctgttact cctgtacctt gtcctcaatt     2520
tccttttctc atcccaaata aataccttct cgc                                  2553
```

<210> SEQ ID NO 26
<211> LENGTH: 132
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 26

```
cctggaacag atgatcaggg aatggctcat tcctttacat ggcctgaaaa cgccgctctt       60
ccactttcag agtcagcgaa aggcttgagg tgcatttgca cacgaggatt ctgccgtttg      120
ttataatgtc ac                                                           132
```

-continued

```
<210> SEQ ID NO 27
<211> LENGTH: 132
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 27
cctggagcag atgatcaggg aatggctcat tcctttacac ggcctgaaaa cgccgctctt      60
ccgctttcag agtcagcgag aggcttgagg tgcctttgca gacgaggagt ttgccaactg     120
ttataaaggc gt                                                         132

<210> SEQ ID NO 28
<211> LENGTH: 243
<212> TYPE: DNA
<213> ORGANISM: Homo sapiens
<220> FEATURE:
<221> NAME/KEY: CDS
<222> LOCATION: (7)..(237)

<400> SEQUENCE: 28 ccagcc atg agg acc ttc gcc ctc ctc acc gcc atg ctt ctc ctg gtg         48
       Met Arg Thr Phe Ala Leu Leu Thr Ala Met Leu Leu Leu Val
        1               5                  10 gcc ctg cac gct cag gca gag gca cgt cag gca aga gct gat gaa gct        96
Ala Leu His Ala Gln Ala Glu Ala Arg Gln Ala Arg Ala Asp Glu Ala
 15                  20                  25                  30 gcc gcc cag cag cag cct gga gca gat gat cag gga atg gct cat tcc       144
Ala Ala Gln Gln Gln Pro Gly Ala Asp Asp Gln Gly Met Ala His Ser
                 35                  40                  45 ttt aca tgg cct gaa aac gcc gct ctt cca ctt tca gag tca gcg aaa       192
Phe Thr Trp Pro Glu Asn Ala Ala Leu Pro Leu Ser Glu Ser Ala Lys
         50                  55                  60 ggc ttg agg tgc att tgc aca cga gga ttc tgc cgt atg tta taa           237
Gly Leu Arg Cys Ile Cys Thr Arg Gly Phe Cys Arg Met Leu
 65                  70                  75 cgtcgc                                                                243

<210> SEQ ID NO 29
<211> LENGTH: 76
<212> TYPE: PRT
<213> ORGANISM: Homo sapiens

<400> SEQUENCE: 29

Met Arg Thr Phe Ala Leu Leu Thr Ala Met Leu Leu Leu Val Ala Leu
 1               5                  10                  15

His Ala Gln Ala Glu Ala Arg Gln Ala Arg Ala Asp Glu Ala Ala Ala
                 20                  25                  30

Gln Gln Gln Pro Gly Ala Asp Asp Gln Gly Met Ala His Ser Phe Thr
             35                  40                  45

Trp Pro Glu Asn Ala Ala Leu Pro Leu Ser Glu Ser Ala Lys Gly Leu
         50                  55                  60

Arg Cys Ile Cys Thr Arg Gly Phe Cys Arg Met Leu
 65                  70                  75

<210> SEQ ID NO 30
<211> LENGTH: 132
<212> TYPE: DNA
<213> ORGANISM: Artificial Sequence
<220> FEATURE:
<223> OTHER INFORMATION: Description of Artificial Sequence: Synthetic
```

-continued

```
Construct

<400> SEQUENCE: 30
ggaccttgtc tactagtccc ttaccgagta aggaaatgta ccggactttt gcggcgagaa         60
ggtgaaagtc tcagtcgctt tccgaactcc acgtaaacgt gtgctcctaa gacggcaaac        120
aatattacag tg                                                            132

<210> SEQ ID NO 31
<211> LENGTH: 132
<212> TYPE: DNA
<213> ORGANISM: Artificial Sequence
<220> FEATURE:
<223> OTHER INFORMATION: Description of Artificial Sequence: Synthetic
      Construct

<400> SEQUENCE: 31
ggacctcgtc tactagtccc ttaccgagta aggaaatgtg ccggactttt gcggcgagaa         60
ggcgaaagtc tcagtcgctc tccgaactcc acggaaacgt ctgctcctca aacggttgac        120
aatatttccg ca                                                            132
```